(12) United States Patent
Grant et al.

(10) Patent No.: US 11,478,235 B2
(45) Date of Patent: Oct. 25, 2022

(54) CLOSURE APPARATUS WITH FLEXIBLE SEALABLE MEMBER AND FLEXIBLE SUPPORT MEMBER

(71) Applicant: Vivasure Medical Limited, Galway (IE)

(72) Inventors: Peter Grant, Dangan (IE); Mark McGoldrick, Athlone (IE); Bartosz Pawlikowski, Moycullen (IE); Noelle Barrett, Knocknacarra (IE); Gerard Brett, Claregalway (IE); Christopher Martin, Oughterard (IE)

(73) Assignee: Vivasure Medical Limited, Galway (IE)

( * ) Notice: Subject to any disclaimer, the term of this patent is extended or adjusted under 35 U.S.C. 154(b) by 335 days.

(21) Appl. No.: 16/592,232

(22) Filed: Oct. 3, 2019

(65) Prior Publication Data
US 2020/0138421 A1 May 7, 2020

Related U.S. Application Data

(63) Continuation of application No. 14/970,335, filed on Dec. 15, 2015, now Pat. No. 10,433,826.
(Continued)

(51) Int. Cl.
*A61B 17/00* (2006.01)
*A61B 17/12* (2006.01)

(52) U.S. Cl.
CPC ............ *A61B 17/0057* (2013.01); *A61B 2017/00477* (2013.01); *A61B 2017/00575* (2013.01);
(Continued)

(58) Field of Classification Search
CPC ...... A61B 17/0057; A61B 2017/00477; A61B 2017/00575; A61B 2017/00597;
(Continued)

(56) References Cited

U.S. PATENT DOCUMENTS

| 321,721 A | 7/1885 | Hassan |
| 2,001,638 A | 5/1935 | Gustaf |

(Continued)

FOREIGN PATENT DOCUMENTS

| CN | 101400308 A | 4/2009 |
| CN | 104287803 A | 1/2015 |

(Continued)

OTHER PUBLICATIONS

U.S. Appl. No. 62/092,212, filed Dec. 15, 2014, McGoldrick et al..
(Continued)

*Primary Examiner* — Kathleen S Holwerda
(74) *Attorney, Agent, or Firm* — Choate, Hall & Stewart LLP; William R. Haulbrook; Peter A. Flynn

(57) ABSTRACT

The disclosed technology provides a device for sealing an aperture in a tissue of a body lumen. The device comprises a flexible support member having a base having (i) a central portion and (ii) one or more lateral support portions, to engage and/or hold a sealable member of the device against an interior surface of the tissue when the device is in the sealing position. The lateral support portions provide additional support surfaces to engage peripheral portions of the sealable member against the interior surface of the tissue.

3 Claims, 68 Drawing Sheets

Related U.S. Application Data

(60) Provisional application No. 62/092,235, filed on Dec. 15, 2014, provisional application No. 62/092,240, filed on Dec. 15, 2014.

(52) U.S. Cl.
CPC ............ *A61B 2017/00597* (2013.01); *A61B 2017/00623* (2013.01); *A61B 2017/00637* (2013.01); *A61B 2017/00654* (2013.01); *A61B 2017/00659* (2013.01)

(58) Field of Classification Search
CPC ........... A61B 2017/00623; A61B 2017/00637; A61B 2017/00654; A61B 2017/00659
See application file for complete search history.

(56) References Cited

U.S. PATENT DOCUMENTS

| | | |
|---|---|---|
| 2,560,162 A | 7/1951 | Ferguson |
| 2,778,254 A | 1/1957 | Carapellotti |
| 3,874,388 A | 4/1975 | King et al. |
| 4,299,230 A | 11/1981 | Kubota |
| 4,583,540 A | 4/1986 | Malmin |
| 4,650,472 A | 3/1987 | Bates |
| 4,705,040 A | 11/1987 | Mueller et al. |
| 4,744,364 A | 5/1988 | Kensey |
| 4,852,568 A | 8/1989 | Kensey |
| 4,890,612 A | 1/1990 | Kensey |
| 4,896,668 A | 1/1990 | Popoff et al. |
| 5,021,059 A | 6/1991 | Kensey et al. |
| 5,037,433 A | 8/1991 | Wilk et al. |
| 5,053,046 A | 10/1991 | Janese |
| 5,085,661 A | 2/1992 | Moss |
| 5,127,412 A | 7/1992 | Cosmetto et al. |
| 5,171,258 A | 12/1992 | Bales et al. |
| 5,192,301 A | 3/1993 | Kamiya et al. |
| 5,269,804 A | 12/1993 | Bales et al. |
| 5,282,827 A | 2/1994 | Kensey et al. |
| 5,320,461 A | 6/1994 | Stanesic |
| 5,330,488 A | 7/1994 | Rath |
| 5,336,231 A | 8/1994 | Adair |
| 5,342,393 A | 8/1994 | Stack |
| 5,350,399 A | 9/1994 | Erlebacher et al. |
| 5,366,480 A | 11/1994 | Corriveau et al. |
| 5,391,182 A | 2/1995 | Chin |
| 5,431,639 A | 7/1995 | Shaw |
| 5,462,560 A | 10/1995 | Stevens |
| 5,470,337 A | 11/1995 | Moss |
| 5,501,691 A | 3/1996 | Goldrath |
| 5,501,700 A | 3/1996 | Hirata |
| 5,507,755 A | 4/1996 | Gresl et al. |
| 5,527,322 A | 6/1996 | Klein et al. |
| 5,531,759 A | 7/1996 | Kensey et al. |
| 5,545,178 A | 8/1996 | Kensey et al. |
| 5,549,633 A | 8/1996 | Evans et al. |
| 5,593,422 A | 1/1997 | Muijs Van de Moer et al. |
| 5,601,557 A | 2/1997 | Hayhurst |
| 5,601,571 A | 2/1997 | Moss |
| 5,620,461 A | 4/1997 | Muijs Van De Moer et al. |
| 5,653,716 A | 8/1997 | Malo et al. |
| 5,662,681 A | 9/1997 | Nash et al. |
| 5,665,096 A | 9/1997 | Yoon |
| 5,676,689 A | 10/1997 | Kensey et al. |
| 5,690,674 A | 11/1997 | Diaz |
| 5,700,273 A | 12/1997 | Buelna et al. |
| 5,700,277 A | 12/1997 | Nash et al. |
| 5,707,393 A | 1/1998 | Kensey et al. |
| 5,722,981 A | 3/1998 | Stevens |
| 5,755,727 A | 5/1998 | Kontos |
| 5,782,861 A | 7/1998 | Cragg et al. |
| 5,797,939 A | 8/1998 | Yoon |
| 5,814,065 A | 9/1998 | Diaz |
| 5,817,074 A | 10/1998 | Racz |
| 5,827,281 A | 10/1998 | Levin |
| 5,860,990 A | 1/1999 | Nobles et al. |
| 5,861,003 A | 1/1999 | Latson et al. |
| 5,868,762 A | 2/1999 | Cragg et al. |
| 5,916,236 A | 6/1999 | Muijs Van de Moer et al. |
| 5,935,147 A | 8/1999 | Kensey et al. |
| 5,941,899 A | 8/1999 | Granger et al. |
| 5,954,732 A | 9/1999 | Hart et al. |
| 5,997,515 A | 12/1999 | de la Torre et al. |
| 6,007,563 A | 12/1999 | Nash et al. |
| 6,033,427 A | 3/2000 | Lee |
| 6,056,768 A | 5/2000 | Cates et al. |
| 6,080,183 A | 6/2000 | Tsugita et al. |
| 6,126,675 A | 10/2000 | Shchervinsky et al. |
| 6,136,010 A | 10/2000 | Modesitt et al. |
| 6,179,863 B1 | 1/2001 | Kensey et al. |
| 6,190,400 B1 | 2/2001 | Van De Moer et al. |
| 6,200,328 B1 | 3/2001 | Cragg et al. |
| 6,206,895 B1 | 3/2001 | Levinson |
| 6,241,768 B1 | 6/2001 | Agarwal et al. |
| 6,245,080 B1 | 6/2001 | Levinson |
| 6,296,658 B1 | 10/2001 | Gershony et al. |
| 6,319,263 B1 | 11/2001 | Levinson |
| 6,350,274 B1 | 2/2002 | Li |
| 6,375,671 B1 | 4/2002 | Kobayashi et al. |
| 6,383,208 B1 | 5/2002 | Sancoff et al. |
| 6,395,015 B1 | 5/2002 | Borst et al. |
| 6,398,796 B2 | 6/2002 | Levinson |
| 6,425,911 B1 | 7/2002 | Akerfeldt et al. |
| 6,461,364 B1 | 10/2002 | Ginn et al. |
| 6,485,481 B1 | 11/2002 | Pfeiffer |
| 6,500,184 B1 | 12/2002 | Chan et al. |
| 6,508,828 B1 | 1/2003 | Akerfeldt et al. |
| 6,520,951 B1 | 2/2003 | Carrillo, Jr. et al. |
| 6,596,012 B2 | 7/2003 | Akerfeldt et al. |
| 6,596,014 B2 | 7/2003 | Levinson et al. |
| 6,638,286 B1 | 10/2003 | Burbank et al. |
| 6,669,707 B1 | 12/2003 | Swanstrom et al. |
| 6,669,735 B1 | 12/2003 | Pelissier |
| 6,702,835 B2 | 3/2004 | Ginn |
| 6,730,112 B2 | 5/2004 | Levinson |
| 6,764,500 B1 | 7/2004 | Muijs Van De Moer et al. |
| 6,770,070 B1 | 8/2004 | Balbierz |
| 6,779,701 B2 | 8/2004 | Bailly et al. |
| 6,786,915 B2 | 9/2004 | Akerfeldt et al. |
| 6,860,895 B1 | 3/2005 | Akerfeldt et al. |
| 6,890,342 B2 | 5/2005 | Zhu et al. |
| 6,932,824 B1 | 8/2005 | Roop et al. |
| 6,939,363 B2 | 9/2005 | Akerfeldt |
| 6,942,674 B2 | 9/2005 | Belef et al. |
| 6,949,107 B2 | 9/2005 | McGuckin, Jr. et al. |
| 6,949,114 B2 | 9/2005 | Milo et al. |
| 6,964,668 B2 | 11/2005 | Modesitt et al. |
| 6,969,397 B2 | 11/2005 | Ginn |
| 6,984,219 B2 | 1/2006 | Ashby et al. |
| 6,989,022 B2 | 1/2006 | Nowakowski |
| 6,997,940 B2 | 2/2006 | Bonutti |
| 7,001,398 B2 | 2/2006 | Carley et al. |
| 7,001,400 B1 | 2/2006 | Modesitt et al. |
| 7,008,440 B2 | 3/2006 | Sing et al. |
| 7,008,441 B2 | 3/2006 | Zucker |
| 7,008,442 B2 | 3/2006 | Brightbill |
| 7,094,248 B2 | 8/2006 | Bachinski et al. |
| 7,169,168 B2 | 1/2007 | Muijs Van De Moer et al. |
| 7,326,221 B2 | 2/2008 | Sakamoto et al. |
| 7,462,188 B2 | 12/2008 | McIntosh |
| 7,534,248 B2 | 5/2009 | Mikkaichi et al. |
| 7,569,063 B2 | 8/2009 | Bailly et al. |
| 7,662,161 B2 | 2/2010 | Briganti et al. |
| 7,678,133 B2 | 3/2010 | Modesitt |
| 7,753,935 B2 | 7/2010 | Brett et al. |
| 7,846,180 B2 | 12/2010 | Cerier |
| 7,918,868 B2 | 4/2011 | Marshall et al. |
| 7,998,169 B2 | 8/2011 | Modesitt |
| 8,002,791 B2 | 8/2011 | Modesitt |
| 8,002,792 B2 | 8/2011 | Modesitt |
| 8,002,793 B2 | 8/2011 | Modesitt |
| 8,012,168 B2 | 9/2011 | Modesitt |
| 8,083,767 B2 | 12/2011 | Modesitt |
| 8,137,380 B2 | 3/2012 | Green et al. |

(56) References Cited

U.S. PATENT DOCUMENTS

| | | | |
|---|---|---|---|
| 8,177,795 B2 | 5/2012 | Niese et al. | |
| 8,241,325 B2 | 8/2012 | Modesitt | |
| 8,267,942 B2 | 9/2012 | Szabo et al. | |
| 8,361,092 B1 * | 1/2013 | Asfora | A61B 17/08 606/153 |
| 8,529,431 B2 | 9/2013 | Baker et al. | |
| 8,597,324 B2 | 12/2013 | Briganti et al. | |
| 8,652,166 B2 | 2/2014 | Åkerfeldt | |
| 8,821,507 B2 | 9/2014 | Axelson, Jr. et al. | |
| 8,906,050 B2 | 12/2014 | Brett et al. | |
| 9,060,751 B2 | 6/2015 | Martin et al. | |
| 9,610,070 B2 | 4/2017 | Martin | |
| 9,850,013 B2 | 12/2017 | Grant et al. | |
| 10,206,668 B2 | 2/2019 | McGoldrick et al. | |
| 10,314,727 B2 | 6/2019 | Liu et al. | |
| 10,433,826 B2 * | 10/2019 | Grant | A61B 17/0057 |
| 11,141,142 B2 | 10/2021 | McGoldrick et al. | |
| 2001/0044631 A1 | 11/2001 | Akin et al. | |
| 2002/0019648 A1 | 2/2002 | Akerfeldt et al. | |
| 2002/0019649 A1 | 2/2002 | Sikora et al. | |
| 2002/0055767 A1 | 5/2002 | Forde et al. | |
| 2002/0107506 A1 | 8/2002 | McGuckin et al. | |
| 2002/0169377 A1 | 11/2002 | Khairkhahan et al. | |
| 2002/0177864 A1 | 11/2002 | Camrud | |
| 2002/0198562 A1 | 12/2002 | Akerfeldt et al. | |
| 2003/0050665 A1 | 3/2003 | Ginn | |
| 2003/0060846 A1 | 3/2003 | Egnelov et al. | |
| 2003/0078598 A1 | 4/2003 | Ginn et al. | |
| 2003/0093093 A1 | 5/2003 | Modesitt et al. | |
| 2003/0120305 A1 | 6/2003 | Jud et al. | |
| 2003/0144695 A1 | 7/2003 | McGuckin et al. | |
| 2003/0216756 A1 | 11/2003 | Klein et al. | |
| 2004/0082906 A1 | 4/2004 | Tallarida et al. | |
| 2004/0092964 A1 | 5/2004 | Modesitt et al. | |
| 2004/0092969 A1 | 5/2004 | Kumar | |
| 2004/0093025 A1 | 5/2004 | Egnelov | |
| 2004/0098044 A1 | 5/2004 | Van de Moer et al. | |
| 2004/0133238 A1 | 7/2004 | Cerier | |
| 2004/0176798 A1 | 9/2004 | Epstein et al. | |
| 2004/0243122 A1 | 12/2004 | Auth et al. | |
| 2005/0021055 A1 | 1/2005 | Toubia et al. | |
| 2005/0021059 A1 | 1/2005 | Cole et al. | |
| 2005/0033326 A1 | 2/2005 | Briganti et al. | |
| 2005/0070957 A1 | 3/2005 | Das | |
| 2005/0143817 A1 | 6/2005 | Hunter et al. | |
| 2005/0149065 A1 | 7/2005 | Modesitt | |
| 2005/0181008 A1 | 8/2005 | Hunter et al. | |
| 2005/0209613 A1 | 9/2005 | Roop et al. | |
| 2005/0251201 A1 | 11/2005 | Roue et al. | |
| 2005/0267520 A1 | 12/2005 | Modesitt | |
| 2005/0273135 A1 | 12/2005 | Chanduszko et al. | |
| 2005/0288706 A1 | 12/2005 | Widomski et al. | |
| 2006/0100665 A1 | 5/2006 | Von Oepen et al. | |
| 2006/0106418 A1 | 5/2006 | Seibold et al. | |
| 2006/0142784 A1 | 6/2006 | Kontos | |
| 2006/0142797 A1 | 6/2006 | Egnelov | |
| 2006/0265008 A1 | 11/2006 | Maruyama et al. | |
| 2006/0287673 A1 | 12/2006 | Brett et al. | |
| 2007/0112385 A1 | 5/2007 | Conlon | |
| 2007/0135826 A1 | 6/2007 | Zaver et al. | |
| 2007/0179509 A1 | 8/2007 | Nagata et al. | |
| 2007/0179527 A1 | 8/2007 | Eskuri et al. | |
| 2007/0197858 A1 | 8/2007 | Goldfarb et al. | |
| 2007/0255313 A1 | 11/2007 | Modesitt | |
| 2007/0282351 A1 | 12/2007 | Harada et al. | |
| 2007/0282373 A1 | 12/2007 | Ashby et al. | |
| 2008/0109017 A1 | 5/2008 | Herweck et al. | |
| 2008/0228204 A1 | 9/2008 | Hamilton et al. | |
| 2008/0243148 A1 | 10/2008 | Mikkaichi et al. | |
| 2008/0312646 A9 | 12/2008 | Auth et al. | |
| 2009/0012521 A1 | 1/2009 | Axelson, Jr. et al. | |
| 2009/0018574 A1 | 1/2009 | Martin | |
| 2009/0048559 A1 | 2/2009 | Grathwohl | |
| 2009/0088723 A1 | 4/2009 | Khosravi et al. | |
| 2009/0112257 A1 | 4/2009 | Preinitz et al. | |
| 2009/0143815 A1 | 6/2009 | Eidenschink et al. | |
| 2009/0143821 A1 | 6/2009 | Stupak | |
| 2009/0312786 A1 | 12/2009 | Trask et al. | |
| 2009/0319017 A1 | 12/2009 | Berez et al. | |
| 2010/0022823 A1 | 1/2010 | Goldfarb et al. | |
| 2010/0094425 A1 | 4/2010 | Bentley et al. | |
| 2010/0114159 A1 | 5/2010 | Roorda et al. | |
| 2010/0125296 A1 | 5/2010 | Modesitt | |
| 2010/0152772 A1 | 6/2010 | Brett et al. | |
| 2010/0222796 A1 | 9/2010 | Brett et al. | |
| 2010/0228184 A1 | 9/2010 | Mavani et al. | |
| 2010/0292717 A1 | 11/2010 | Petter-Puchner et al. | |
| 2011/0077667 A1 | 3/2011 | Singhatat et al. | |
| 2011/0082495 A1 | 4/2011 | Ruiz | |
| 2011/0087270 A1 | 4/2011 | Penner et al. | |
| 2011/0224728 A1 | 9/2011 | Martin et al. | |
| 2011/0270284 A1 | 11/2011 | Beauchamp et al. | |
| 2012/0059399 A1 | 3/2012 | Hoke et al. | |
| 2012/0089166 A1 | 4/2012 | Modesitt | |
| 2012/0165957 A1 | 6/2012 | Everland et al. | |
| 2012/0226308 A1 * | 9/2012 | Martin | A61B 17/0057 606/213 |
| 2012/0226309 A1 | 9/2012 | Jonsson | |
| 2012/0296275 A1 | 11/2012 | Martin et al. | |
| 2012/0302987 A1 | 11/2012 | Jonsson | |
| 2013/0116799 A1 | 5/2013 | Derwin et al. | |
| 2013/0218125 A1 | 8/2013 | Stopek et al. | |
| 2013/0218201 A1 | 8/2013 | Obermiller et al. | |
| 2013/0274795 A1 * | 10/2013 | Grant | A61B 17/42 606/213 |
| 2014/0018846 A1 | 1/2014 | Grant et al. | |
| 2014/0018847 A1 | 1/2014 | Grant et al. | |
| 2014/0058439 A1 | 2/2014 | White | |
| 2014/0180314 A1 | 6/2014 | Asfora | |
| 2014/0194926 A1 | 7/2014 | Bailly et al. | |
| 2014/0200597 A1 | 7/2014 | Klein et al. | |
| 2014/0207183 A1 * | 7/2014 | Shipp | A61B 17/0057 606/213 |
| 2014/0277113 A1 | 9/2014 | Stanley et al. | |
| 2014/0345109 A1 | 11/2014 | Grant et al. | |
| 2015/0045818 A1 | 2/2015 | Kim et al. | |
| 2016/0051239 A1 | 2/2016 | Martin et al. | |
| 2016/0166241 A1 | 6/2016 | McGoldrick et al. | |
| 2017/0181736 A1 | 6/2017 | McGoldrick et al. | |
| 2017/0281142 A1 | 10/2017 | Martin et al. | |
| 2019/0021710 A1 | 1/2019 | McGoldrick et al. | |

FOREIGN PATENT DOCUMENTS

| | | |
|---|---|---|
| CN | 104771200 A | 7/2015 |
| CN | 105073064 A | 11/2015 |
| DE | 19711288 B4 | 11/2004 |
| DE | 102010048908 A1 | 4/2012 |
| DE | 102013101338 A1 | 8/2014 |
| EP | 0551198 A1 | 7/1993 |
| EP | 0761250 A1 | 3/1997 |
| EP | 0894475 A1 | 2/1999 |
| EP | 1 046 375 A1 | 10/2000 |
| EP | 1879505 B1 | 1/2008 |
| EP | 2260770 A2 | 12/2010 |
| EP | 2 292 147 A1 | 3/2011 |
| EP | 2 628 592 A1 | 8/2013 |
| EP | 2 777 543 A1 | 9/2014 |
| WO | WO-1994/008513 A1 | 4/1994 |
| WO | WO-00/07520 A1 | 2/2000 |
| WO | WO-2000/033744 A1 | 6/2000 |
| WO | WO-2002/102236 A2 | 12/2002 |
| WO | WO-2004/012601 A2 | 2/2004 |
| WO | WO-2004/012603 A2 | 2/2004 |
| WO | WO-2004/012627 A1 | 2/2004 |
| WO | WO-2006/117766 A2 | 11/2006 |
| WO | WO-2007/011353 A2 | 1/2007 |
| WO | WO-2007/057933 A1 | 5/2007 |
| WO | WO-2007/089603 A2 | 8/2007 |
| WO | WO-2008/042229 A2 | 4/2008 |
| WO | WO-2008/152617 A2 | 12/2008 |
| WO | WO-2009/070651 A1 | 6/2009 |
| WO | WO-2009/149455 A1 | 12/2009 |
| WO | WO-2010/027693 A2 | 3/2010 |

(56) References Cited

FOREIGN PATENT DOCUMENTS

| WO | WO-2010/123821 | A1 | 10/2010 |
|---|---|---|---|
| WO | WO-2011/080588 | A2 | 7/2011 |
| WO | WO-2012/090069 | A2 | 7/2012 |
| WO | WO-2012/156819 | A2 | 11/2012 |
| WO | WO-2013/007534 | A1 | 1/2013 |
| WO | WO-2013/128292 | A2 | 9/2013 |
| WO | WO-2013/188351 | A2 | 12/2013 |
| WO | WO-2014/140325 | A1 | 9/2014 |
| WO | WO-2014/141209 | A1 | 9/2014 |
| WO | WO-2014/149642 | A2 | 9/2014 |
| WO | WO-2016/096930 | A1 | 6/2016 |
| WO | WO-2016/096932 | A1 | 6/2016 |
| WO | WO-2017/102941 | A1 | 6/2017 |

OTHER PUBLICATIONS

U.S. Appl. No. 62/092,235, filed Dec. 15, 2014, Grant et al..
U.S. Appl. No. 62/092,240, filed Dec. 15, 2014, Grant et al..
European Patent Office Partial Supplementary Search Report. Application No. 12784868.7, dated Jan. 12, 2015, 5 pages.
Extended European Search Report, Application No. EP 11852355.4, dated Sep. 28, 2015, 7 pages.
Grant, et al., Hales' 1733 Haemastaticks, Anesthesiology, 112(1) (2010).
Hales, Stephen, Statical Essays, vol. 2 (1773).
International Preliminary Report on Patentability, PCT/IB2010/003461, dated Jul. 12, 2012, 10 pages.
International Preliminary Report on Patentability, PCT/IE2006/000043, dated Oct. 30, 2007, 10 pages.
International Search Report, PCT/EP2015/079904, 7 pages, dated Mar. 1, 2016.
International Search Report, PCT/EP2015/079906 (Closure Apparatus With Flexible Sealable Member and Flexible Support Member, filed Dec. 15, 2015), 7 pages, dated May 24, 2016.
International Search Report, PCT/EP2016/081183, 5 pages, dated Mar. 20, 2017.
International Search Report, PCT/IB2010/003461, dated Oct. 11, 2011, 6 pages.
International Search Report, PCT/IB2011/003295, dated Jun. 29, 2012, 4 pages.
International Search Report, PCT/IB2012/001101, dated Jan. 30, 2013, 3 pages.
International Search Report, PCT/IB2013/000839, dated Jan. 14, 2014, 6 pages.
International Search Report, PCT/IB2014/059848, dated Jul. 7, 2014, 5 pages.
Written Opinion, PCT/EP2015/079904, 8 pages, dated Mar. 1, 2016.
Written Opinion, PCT/EP2015/079906 (Closure Apparatus With Flexible Sealable Member and Flexible Support Member, filed Dec. 15, 2015), 11 pages, dated May 24, 2016.
Written Opinion, PCT/EP2016/081183, 12 pages, dated Mar. 20, 2017.
Written Opinion, PCT/IB2010/003461, dated Oct. 11, 2011, 9 pages.
Written Opinion, PCT/IB2011/003295, dated Jun. 29, 2012, 5 pages.
Written Opinion, PCT/IB2012/001101, dated Jan. 30, 2013, 5 pages.
Written Opinion, PCT/IB2013/000839, dated Jan. 14, 2014, 11 pages.
Written Opinion, PCT/IB2014/059848, dated Jul. 7, 2014, 8 pages.
Written Opinion, PCT/IE2006/000043, dated Oct. 29, 2007, 9 pages.

* cited by examiner

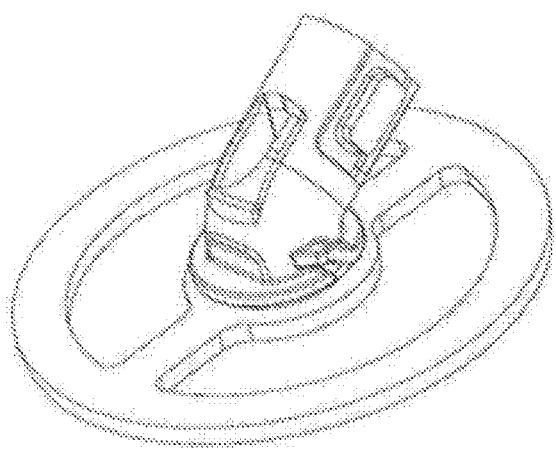
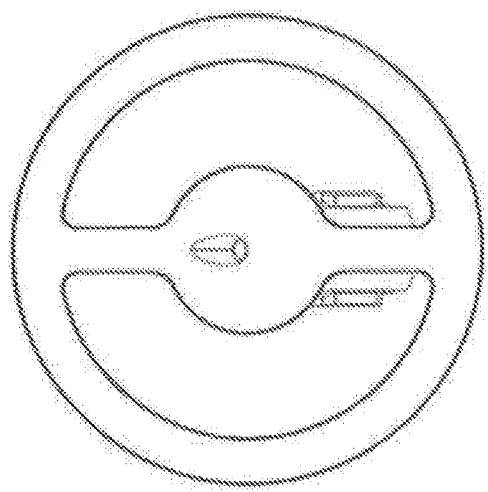
FIG. 28A
FIG. 28B
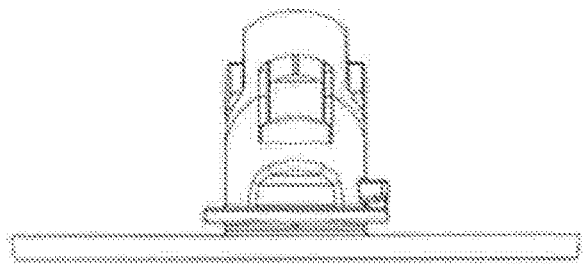
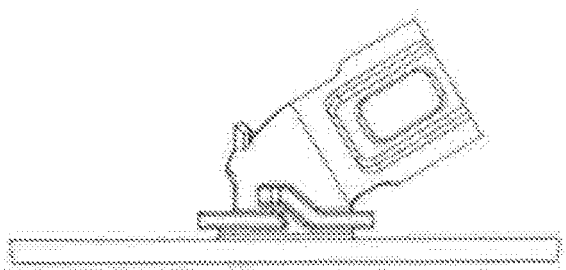
FIG. 28C
FIG. 28D

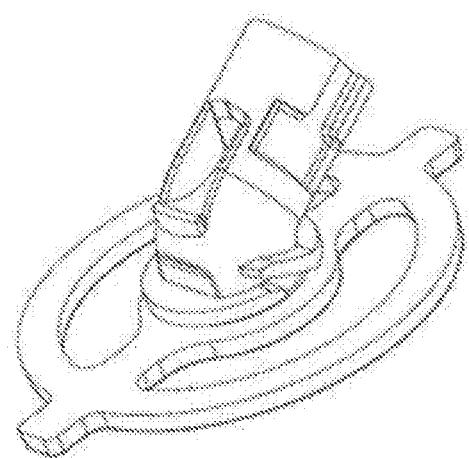 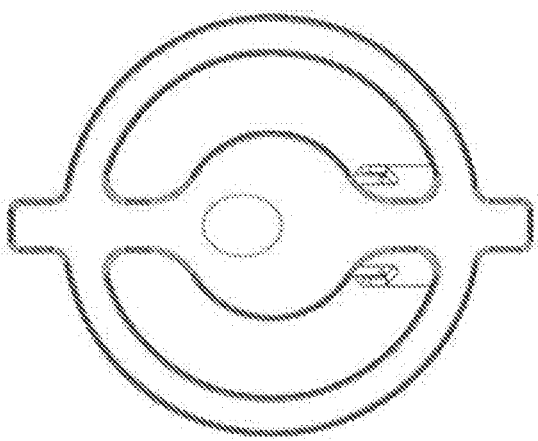
FIG. 29A    FIG. 29B
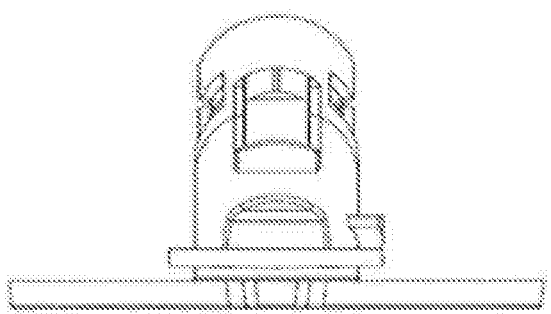 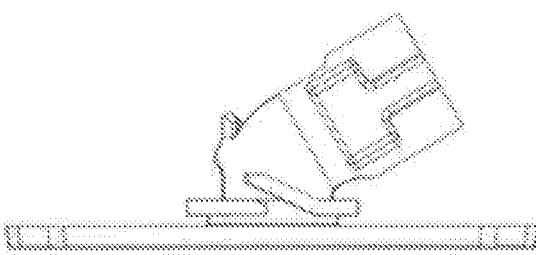
FIG. 29C    FIG. 29D

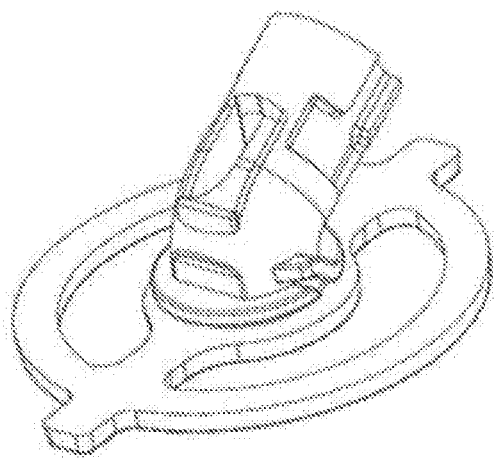 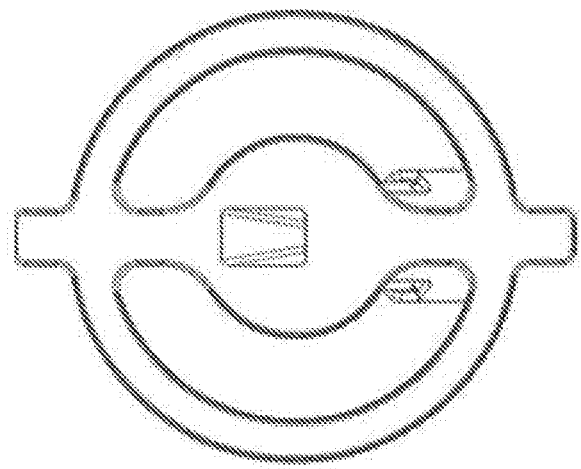
FIG. 30A  FIG. 30B
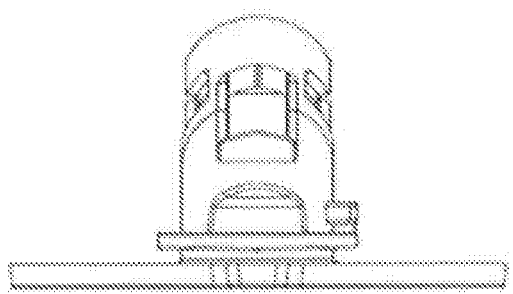 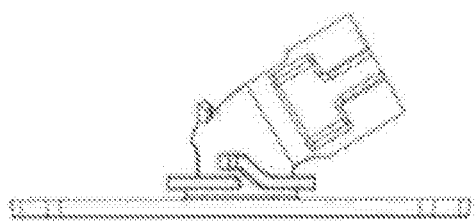
FIG. 30C  FIG. 30D

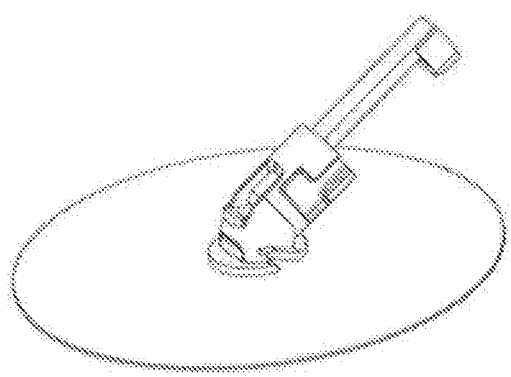
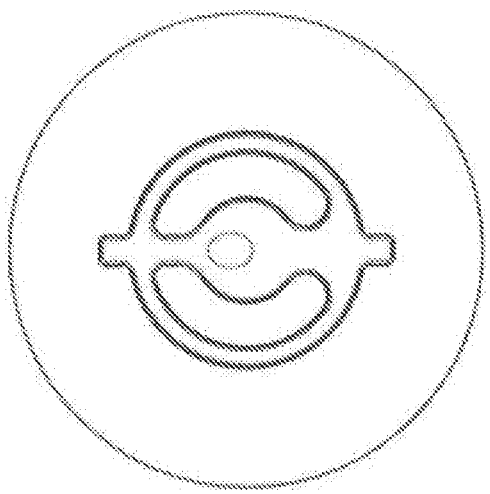
FIG. 68A
FIG. 68B
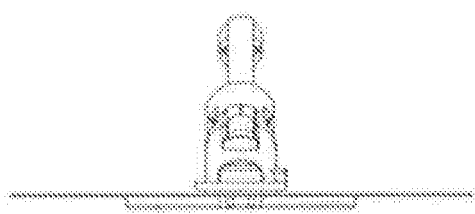
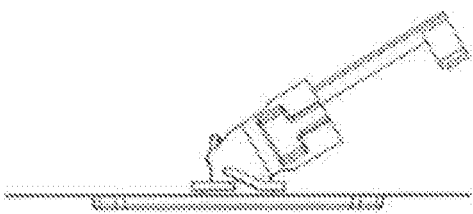
FIG. 68C
FIG. 68D

CLOSURE APPARATUS WITH FLEXIBLE SEALABLE MEMBER AND FLEXIBLE SUPPORT MEMBER

CROSS REFERENCE TO RELATED APPLICATIONS

This application is a continuation of U.S. patent application Ser. No. 14/970,335, filed on Dec. 15, 2015 (now U.S. Pat. No. 10,433,826), which claims priority to and the benefit of, U.S. Provisional Patent Application Nos. 62/092,235 and 62/092,240, filed Dec. 15, 2014, the disclosure of which are hereby incorporated by reference in their entirety.

BACKGROUND

During a surgical or endoscopic operation on a body lumen, e.g., a blood vessel, an aperture is formed (e.g., from an arteriotomy) in the tissue of the lumen. Following the procedure, the aperture has to be closed in order for the lumen to heal. One relatively new type of closure apparatus has a flexible disc that is delivered into the body lumen to seal the aperture. The disc maintains the tissue in apposition until the lumen is healed, allowing the wound to heal from the inside of the lumen. The disc may operate in conjunction with a rigid core, which prevents the disc from dislodging from the sealing position.

In certain patient groups, the area surrounding the tissue within the body lumen is diseased and/or has accumulation (e.g., plaque or calcified lesions on the tissue wall). Due to the irregular surface topology of such areas, the effectiveness of the seal made by certain closure apparatuses is reduced, as channels are formed between the disc and the tissue surface.

There are benefits of improving the seal formed by a closure apparatus when closing an aperture formed in the tissue of the body lumen.

SUMMARY

The disclosed technologies provide an implant closure device having a flexible sealable member and a flexible support member that operate in conjunction to improve a seal formed between the sealable member and the tissue surface of the body lumen during closure of an aperture in the body lumen. The support member maintains the peripheral portions of the sealable member against an interior tissue of the body lumen and/or provides greater rigidity to the peripheral regions of the flexible sealable member. The structure, in combination with the hydraulic pressure present in the body lumen (e.g., hemodynamic pressure of blood in a blood vessel), improves the tamponade formed by the device over the aperture. The structure is sufficiently flexible to bend so as to fit through the aperture during the deployment of the closure device in the body lumen.

The disclosed technologies prevent the inadvertent dislodgment of the closure device from the sealing position and reduce the risk of inadvertent pull-out of the implant device from within the lumen, e.g., during the deployment of the device or post-implantation of the device. A surgeon can assert greater force on the tissue, giving the surgeon a better tactile feedback of the positioning of the implant. As demonstrated herein, the provided technologies achieve unprecedented acute sealing time in closing a blood vessel and unprecedented loss of fluid from such vessel. In certain embodiments, the increased rigidity is directional to allow greater force to be directed to a specific area of the tissue surrounding the formed aperture.

A remarkable feature of the provided technologies is that they enable new types of interventional, surgical, and endoscopic procedures in providing a reliable and consistent closure of an aperture in a body lumen without regard to the tissue surface topography. In addition, closure of larger apertures in healthy tissue can also be performed.

In some embodiments, provided technologies allow for a thin-profile implant closure device to be deployed in the body lumen. The thin-profile implant is quicker to be encapsulated by the build-up resulting from the natural response of the body to the closure implant. In addition, the thin profile implant creates less resistance to flow in the lumen. As a result, closure of small vessels can also be performed.

In some embodiments, provided technologies improve the manufacturability of the implant closure device. The support member includes a structural feature to allow the flexible sealable member to be assembled with the support member, without distortion or deformation, thereby ameliorating the risk of the sealable member being damaged during such assembly.

In certain embodiments, the implant closure device self-guides to a sealing position due to, for example, hemostatic hydraulic pressure in the body lumen so a surgeon does not have to hold the device in a particular location when the device is being deployed.

In one aspect, the present disclosure describes a device for sealing an aperture in a tissue of a body lumen (e.g., to close a surgical or endoscopic perforation in a body cavity, such as the gastrointestinal tract, heart, peritoneal cavity, esophagus, vagina, rectum, trachea, bronchi, and blood vessel, e.g., the femoral artery, iliac artery, subclavian artery, ascending and decending aorta, auxiliary and brachial arteries, femoral vein, iliac vein, subclavian vein, and vena cava). The device comprises a sealable member and a support member. The support member (e.g., a foot with an O-ring foot-core) comprises a base and a column, the base being disposed in the body lumen to retain and/or hold the sealable member against the interior surface of the tissue of the body lumen when the device is in the sealing position. The base comprises: (i) a central portion having a support surface to engage the sealable member against the interior surface of the tissue when the device is in the sealing position; and (ii) one or more lateral support portions (e.g., a ring, cantilever, arc-protrusion, perimeter) extending from the central portion such that the one or more lateral support portions provide additional support surfaces to engage peripheral portions of the sealable member against the interior surface of the tissue when the device is in the sealing position (e.g., wherein the one or more lateral support surface provide compression exertion against the interior surface of the tissue).

In some embodiments, the closure device comprises a guard member. The column is disposed in and through the aperture and has an engagement portion to secure the guard member to the support member. In some embodiments, the support member retains the guard member near the exterior surface of the tissue when the device is in the sealing position. In some embodiments, the guard member (e.g., an insertable or engagable pin or cage) is positionable near the exterior surface of the tissue adjacent the aperture when the device is in the sealing position, the guard member being moveable to be positioned relative to the tissue such a portion of the tissue is disposed between the guard member and the sealable member when the device is in the sealing position. The sealable member (e.g., a flexible wing) is positionable against an interior surface of the tissue adjacent the aperture in the tissue when the device is in a sealing position (e.g., so as to form a tamponade at the aperture).

In some embodiments, the base has a gap between the one or more lateral support portions and the central portion, thereby allowing the base of the support member to bend to conform to the interior surface of the tissue when the device is in the sealing position.

In some embodiments, the base does not have a gap between the one or more lateral support portions and the central portion.

In some embodiments, the central portion includes an anterior support portion and a posterior support portion (e.g., wherein the posterior support portion is disposed proximally to the column, and the anterior support portion is disposed distally to the column). The one or more lateral support portions extend from at least one of the anterior support portion and the posterior support portion.

In some embodiments, the posterior support portion is disposed proximally to the column and has first maximum cross-sectional area. The anterior support portion is disposed distally to the column and has a second maximum cross-sectional area, the first maximum cross-sectional area being larger than the second maximum cross-sectional area such that the posterior support portion is more rigid than the anterior support portion (e.g., to provide more resistance and/or surface contact to the sealable member along the direction of the posterior support portion in keeping the device from being withdrawn through the aperture).

In some embodiments, the first maximum cross-sectional area is substantially similar to the second maximum cross-sectional area (e.g., wherein each of the first maximum cross-sectional area and the second maximum cross-sectional area is at least 30%, 40%, 50%, 60%, 70%, or 80% of a maximum cross-sectional area of the central portion).

In some embodiments, the column is angularly disposed, when the device is in the sealing position, in the aperture along an axis corresponding to a longitudinal axis of a delivery shaft to which the support member is releasably attached (e.g., wherein the column forms an angle, e.g., between about 10 and 70 degrees, between a plane corresponding to the sealable member in a rest configuration and the longitudinal axis of the delivery shaft). The posterior support portion is more rigid along a direction of the delivery shaft than along other directions, thereby providing more resistance to the sealable member along the direction of the delivery shaft in keeping the device from being withdrawn through the aperture.

In some embodiments, the one or more lateral support portions extend from the posterior support portion at a location between a posterior end of the posterior support portion and the central portion such that a region of the posterior support portion defines additional surface area to maintain and/or push a posterior end of the sealable member against the interior surface of the tissue when the device is in the sealing position.

In some embodiments, the one or more lateral support portions extend from the anterior support portion at a location between an anterior end of the anterior support portion and the central portion such that a region of the anterior support portion defines additional surface area to maintain and/or push an anterior end of the sealable member against the interior surface of the tissue when the device is in the sealing position.

In some embodiments, the sealable member and the support member, collectively, form a single integrated structure.

In some embodiments, the one or more lateral support portions form a ring (e.g., circle, oval, rectangular, ellipse, diamond) around the central portion.

In some embodiments, each of the one or more lateral support portion and the central portion aligns along a plane when the device is in a stowed configuration. The one or more lateral support portion and the central portion bending to form a continuous curved surface when the sealable member is positioned against the interior surface of the tissue when the device is in the sealing position.

In some embodiments, the support member and/or the sealable member comprise at least one material selected from the group consisting of Polydioxanone, Poly-L-lactide, Poly-D-lactide, Poly-DL-lactide, Polyglycolide, ε-Caprolactone, and Polyethylene glycol. In some embodiments, the material of the support member and/or sealable member is a co-polymer of, for example, but not limited to, Polydioxanone, Poly-L-lactide, Poly-D-lactide, Poly-DL-lactide, Polyglycolide, ε-Caprolactone, and Polyethylene glycol. In some embodiments, the co-polymer includes (a) monomers of Polydioxanone, Poly-L-lactide, Poly-D-lactide, Poly-DL-lactide, Polyglycolide, ε-Caprolactone, or Polyethylene glycol, and (b) one or more additional monomers. In some embodiments, the (a) and (b) monomers form a polymer that is bioabsorbable.

In some embodiments, the column comprises a threaded portion to secure the sealable member to the support member (e.g., such that the column allows the sealable member to rotatably translate onto a contact surface of the base).

In another aspect, the present disclosure describes a closure system for sealing an aperture in a tissue (e.g., to close a surgical or endoscopic perforation in a body cavity, such as the gastrointestinal tract, heart, peritoneal cavity, esophagus, vagina, rectum, trachea, bronchi, and blood vessel, e.g., the femoral artery, iliac artery, subclavian artery, ascending and descending aorta, auxiliary and brachial arteries, femoral vein, iliac vein, subclavian vein, and vena cava). The closure system comprises a delivery device; and a closure device.

The delivery device has an attachment to releasably attach the closure device for delivery to the aperture in the tissue (e.g., wherein the delivery device is structured to move the device (i) from a stowed configuration to a delivery configuration and (ii) from the delivery configuration to a deployed configuration).

The closure device comprises a sealable member and a support member. The sealable member (e.g., a flexible wing) is positionable against an interior surface of the tissue adjacent the aperture in the tissue when the device is in a sealing position (e.g., so as to form a tamponade at the aperture). The support member (e.g., a foot with an O-ring foot-core) comprises a base and a column, the base being disposed in the body lumen to retain the sealable member against the interior surface of the tissue of the body lumen when the device is in the sealing position. The base comprises: a central portion having a support surface to engage the sealable member against the interior surface of the tissue when the device is in the sealing position; and one or more lateral support portions (e.g., a ring, cantilever, arc-protrusion, perimeter) extended from the central portion such that the one or more lateral support portions provide additional support surfaces to engage peripheral portions of the sealable member against the interior surface of the tissue when the device is in the sealing position.

In some embodiments, the closure device comprises a guard member. In some embodiments, the column is disposed in and through the aperture and has an engagement portion to secure the guard member to the support member. In some embodiments, the guard member (e.g., an insertable or engagable pin or cage) is positionable near the exterior surface of the tissue adjacent the aperture when the device is in the sealing position. In some embodiments, the guard member is moveable relative to the tissue, e.g., to engage an engagement portion on the support member such that a portion of the tissue is disposed between the guard member and the sealable member when the device is in the sealing position.

In some embodiments, the base has a gap between the lateral support portions and the central portion, thereby allowing the base to flexibly bend to conform to the interior surface of the tissue when the device is in the sealing position.

In some embodiments, the base does not have a gap between the lateral support portions and the central portion.

In some embodiments, the central portion comprises an anterior support portion and a posterior support portion (e.g., wherein the posterior support portion is disposed proximally to the column and the anterior support portion is disposed distally to the column). The lateral support portions extend from at least one of the anterior support portion and the posterior support portion.

In some embodiments, the posterior support portion is disposed proximally to the column and has first maximum cross-sectional area, and the anterior support portion is disposed distally to the column and has a second maximum cross-sectional area. The first maximum cross-sectional area is larger than the second maximum cross-sectional area such that the posterior support portion is more rigid than the anterior support portion (e.g., to provide more resistance and/or surface contact to the sealable member along the direction of the posterior support portion in keeping the device from being withdrawn through the aperture).

In some embodiments, the first maximum cross-sectional area is substantially similar to the second maximum cross-sectional area (e.g., wherein each of the first maximum cross-sectional area and the second maximum cross-sectional area is at least 30%, 40%, 50%, 60%, 70%, or 80% of a maximum cross-sectional area of the central portion).

In some embodiments, the column is angularly disposed, when the device is in the sealing position, in the aperture along an axis corresponding to a longitudinal axis of a delivery shaft to which the support member is releasably attached (e.g., wherein the column forms an angle, e.g., between about 10 and 70 degrees, between a plane corresponding to a sealable member in a rest configuration and the longitudinal axis of the delivery shaft). In some embodiments, the posterior support portion is more rigid along a direction of the delivery shaft than along other directions, thereby providing more resistance to the sealable member along the direction of the delivery shaft in keeping the device from being withdrawn through the aperture.

In some embodiments, the lateral support portions extend from the posterior support portion at a location between a posterior end of the posterior support portion and the central portion such that a region of the posterior support portion defines additional surface area to maintain and/or push a posterior end of the sealable member against the interior surface of the tissue when the device is in the sealing position.

In some embodiments, the one or more lateral support portions extend from the anterior support portion at a location between an anterior end of the anterior support portion and the central portion such that a portion of the anterior support portion defines additional surface area to maintain and/or push an anterior end of the sealable member against the interior surface of the tissue when the device is in the sealing position.

In some embodiments, the one or more lateral support portions form a ring (e.g., circle, oval, rectangular, ellipse, diamond) around the central portion.

In some embodiments, each of the one or more lateral support portion and the central portion aligns along a plane when the device is in a stowed configuration, the one or more lateral support portion and the central portion bending to form a continuous curved surface when the sealable member is positioned against the interior surface of the tissue when the device is in the sealing position.

In some embodiments, the sealable member and the support member, collectively, form a single integrated structure.

In some embodiments, the support member and/or sealable member comprises at least one material selected from the group consisting of Polydioxanone, Poly-L-lactide, Poly-D-lactide, Poly-DL-lactide, Polyglycolide, ε-Caprolactone, and Polyethylene glycol. In some embodiments, the material of the support member and/or sealable member is a co-polymer of, for example, but not limited to, Polydioxanone, Poly-L-lactide, Poly-D-lactide, Poly-DL-lactide, Polyglycolide, ε-Caprolactone, and Polyethylene glycol. In some embodiments, the co-polymer includes (a) monomers of Polydioxanone, Poly-L-lactide, Poly-D-lactide, Poly-DL-lactide, Polyglycolide, ε-Caprolactone, or Polyethylene glycol, and (b) one or more additional monomers. In some embodiments, the (a) and (b) monomers form a polymer that is bioabsorbable and/or biodegradable.

In some embodiments, the column comprises a threaded portion to secure the sealable member to the support member (e.g., such that the column allows the sealable member to rotatably translate onto a contact surface of the base).

In another aspect, the present disclosure describes a device for sealing an aperture in a tissue of a body lumen (e.g., to close a surgical or endoscopic perforation in a body cavity, such as the gastrointestinal tract, heart, peritoneal cavity, esophagus, vagina, rectum, trachea, bronchi, and blood vessel, e.g., the femoral artery, iliac artery, subclavian artery, ascending and decending aorta, and auxiliary and brachial arteries, femoral vein, iliac vein, subclavian vein, vena cava). The device comprises a sealable member (e.g., a flexible wing) positionable against an interior surface of the tissue adjacent the aperture in the tissue when the device is in a sealing position (e.g., so as to form a tamponade at the aperture); and a support member (e.g., a foot with an O-ring foot-core) comprising a base and a column. The base is disposed in the body lumen to retain the sealable member against the interior surface of the tissue of the body lumen when the device is in the sealing position.

In some embodiments, the device comprises a guard member (e.g., an insertable or engagable pin or cage) positionable near an exterior surface of the tissue adjacent the aperture when the device is in the sealing position, the guard member being moveable to be positioned relative to the tissue such that a portion of the tissue is disposed between the guard member and the sealable member when the device is in the sealing position. In some embodiments, the column is disposed in and through the aperture and has (i) an engagement portion (e.g., a hole to retain a guard pin or a recess/tab on the column of the column for a guard shoe) to secure the guard member to the support member and (ii) a threaded portion to secure the sealable member to the support member. In some embodiments, the guard member engages against the exterior surface of the tissue when the device is in the sealing position.

Further features and aspects of example embodiments of the present invention are described in more detail below with reference to the appended Figures.

BRIEF DESCRIPTION OF THE DRAWING

FIGS. 23A-72C are diagrams of views of various embodiments of the closure apparatus, according to illustrative embodiments of the invention (e.g., three or four views of each embodiments are shown—e.g., as A-C or A-D).

DETAILED DESCRIPTION

As described herein, illustrative embodiments provide surgical closure systems, devices, and methods useful for (i) bringing about alignment of the tissues surrounding a perforation in a body lumen, thereby closing the aperture in the body lumen, (ii) forming a tamponade at the aperture when bringing about the alignment of the tissues, and (iii) maintaining the tissues surrounding the perforation in alignment until the perforation is sealed. The systems, devices, and methods are used, in some embodiments, to close a surgical perforation in a body cavity, such as the gastrointestinal tract, heart, peritoneal cavity, esophagus, vagina, rectum, trachea, bronchi, and blood vessel, including for example, but not limited to the femoral artery, subclavian artery, ascending and descending aorta, auxiliary and brachial arteries femoral vein, iliac vein, subclavian vein, and vena cava.

Figure 1A:
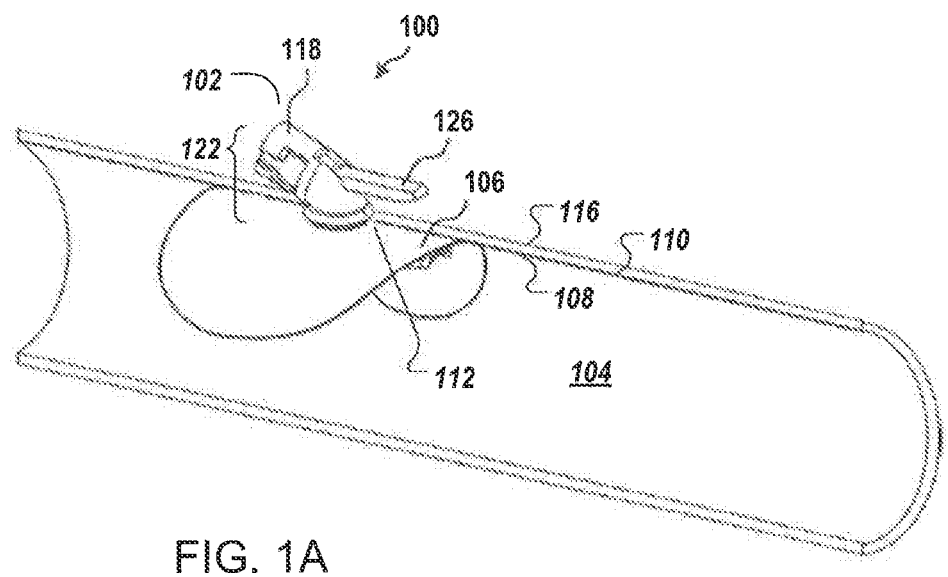
FIGS. 1A and 1B are diagrams showing a perspective view and a cross-sectional view of an exemplary closure device deployed at a sealing position in a body lumen.
Figure 1B:
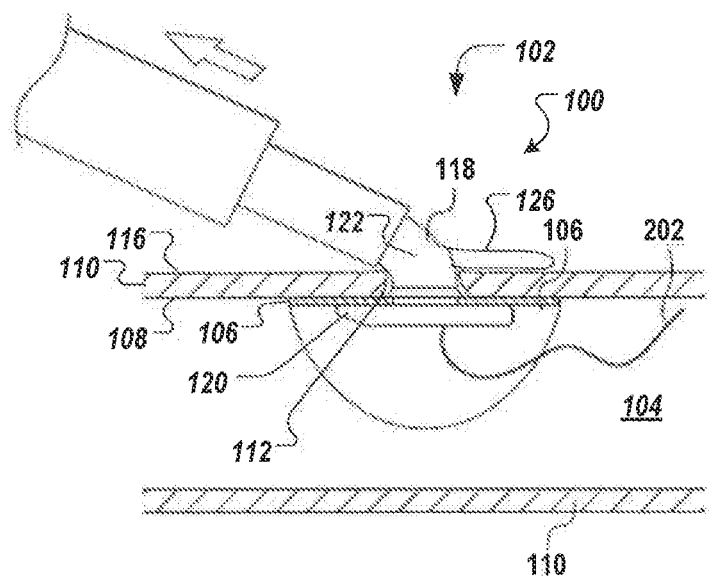

FIGS. 1A and 1B are diagrams showing a perspective view and a cross-sectional view of an exemplary closure device 100 deployed at a sealing position 102 in a body lumen 104.

The closure device 100 includes a sealable member 106 (e.g., a flexible wing) positionable against an interior surface 108 of the tissue 110 adjacent the aperture 112 in the tissue (e.g., so as to form a tamponade at the aperture 112). Although flat or slightly curved when in a relaxed state, the sealable member 106 flexibly curves to conform to the interior surface 108 of the lumen 104 to which it engages, in the deployed state.

The closure device 100 includes a support member 118 (e.g., a foot) comprising a base 120 (e.g., an O-ring footcore) and a column 122. The base 120 supports the sealable member 106 during the delivery and deployment of the sealable member 106 in the body lumen 104 by retaining and/or holding the sealable member 106 against the interior surface 108 of the tissue 110 when the closure device 100 is in the sealing position. In some embodiments, the base 120 exerts a force to bias the sealable member 106 against the tissue.

Figures 2A, 2B:
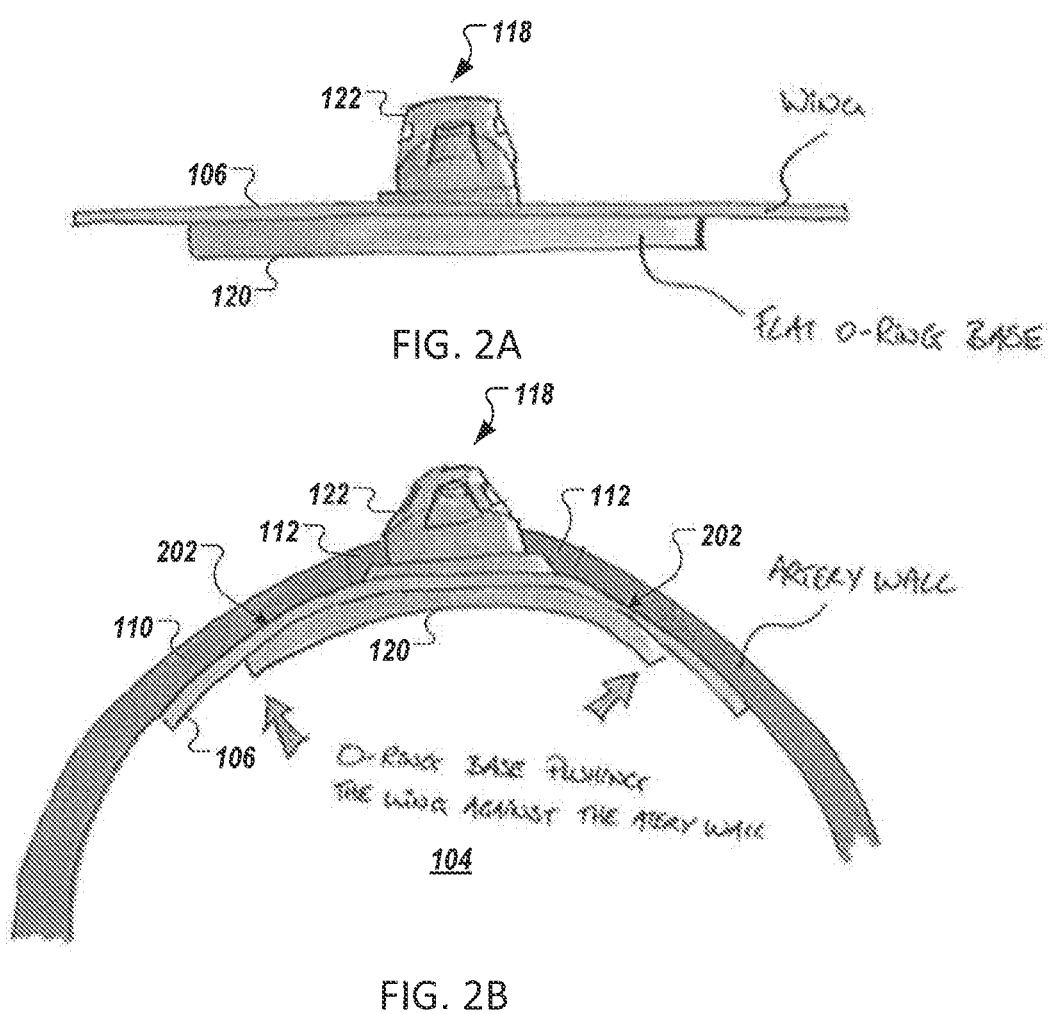
FIG. 2A is a diagram of the closure device in a stowed position, according to an illustrative embodiment.
FIG. 2B is a diagram of the closure device in a deployed state at the sealing position, according to an illustrative embodiment.

FIG. 2A is a diagram of the sealable member 106 and the base 120 of the support member 118 in a relaxed position, according to an illustrative embodiment. FIG. 2B is a diagram of the members in a deployed state at the sealing position, according to an illustrative embodiment. In certain embodiments, the base 120 slightly bends when in the relaxed position.

In some embodiments, once implanted in the body lumen, the base 120 presses against the interior shape of the lumen 104 by hydraulic pressure exerted by fluids in the body lumen 104 (e.g., by hemodynamic hydraulic forces exerted by blood in a blood vessel). In doing so, the base 120 improves the seal formed by the sealable member 106 over the aperture 112, thus, providing a faster and more secure closure of the aperture 112. The base 120 connects to the column 122, which is disposed, when the device is in the sealing position, in and through the aperture 110. In certain embodiments, a guard member 126 (see FIGS. 1A and 1B) maintains the column 122 in position at the sealing position once the device 100 is deployed, whereby the guard member 126 prevents the dislodgement of the sealable member 106 from the sealing position, e.g., due to impact near the aperture or movement of the patient.

In some embodiments, once implanted in the body lumen, the base 120 bends against the interior shape of the lumen 104 so as to compress the peripheral portions of the sealable member 106 against the interior surface 108 of the tissue 110. Hydraulic pressure, as discussed above, may contribute to the bending of the base 120 in such embodiments. The base 120, in these embodiments, also improves the seal formed by the sealable member 106 over the aperture 112, thus, providing a faster and more secure closure of the aperture 112. The support member 118 may also include a guard member 126 to prevent the dislodgement of the sealable member 106 from the sealing position, e.g., due to impact near the aperture or movement of the patient.

In some embodiments, the support member 118 may include a guard member 126 to prevent the dislodgement of the sealable member 106 from the sealing position, when hydraulic pressure of a blood vessel is relatively low. The guard member may provide a mean to compress the implant into a vessel (e.g., by an operator).

Lateral Support Portions of the Base

Figure 3A:
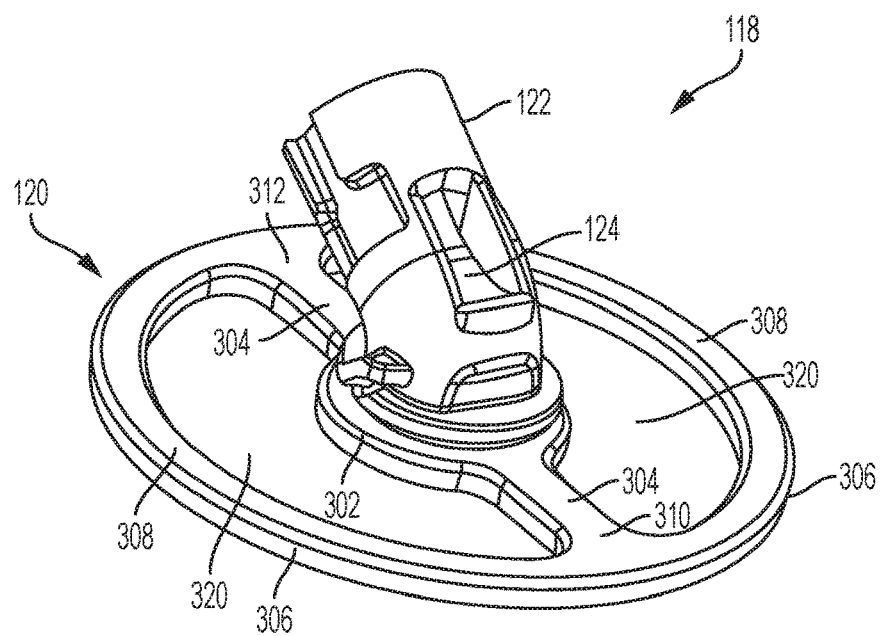
FIGS. 3A and 3B are diagrams showing a perspective view and a bottom view of a support member of the closure device, according to an illustrative embodiment.
Figure 3B:
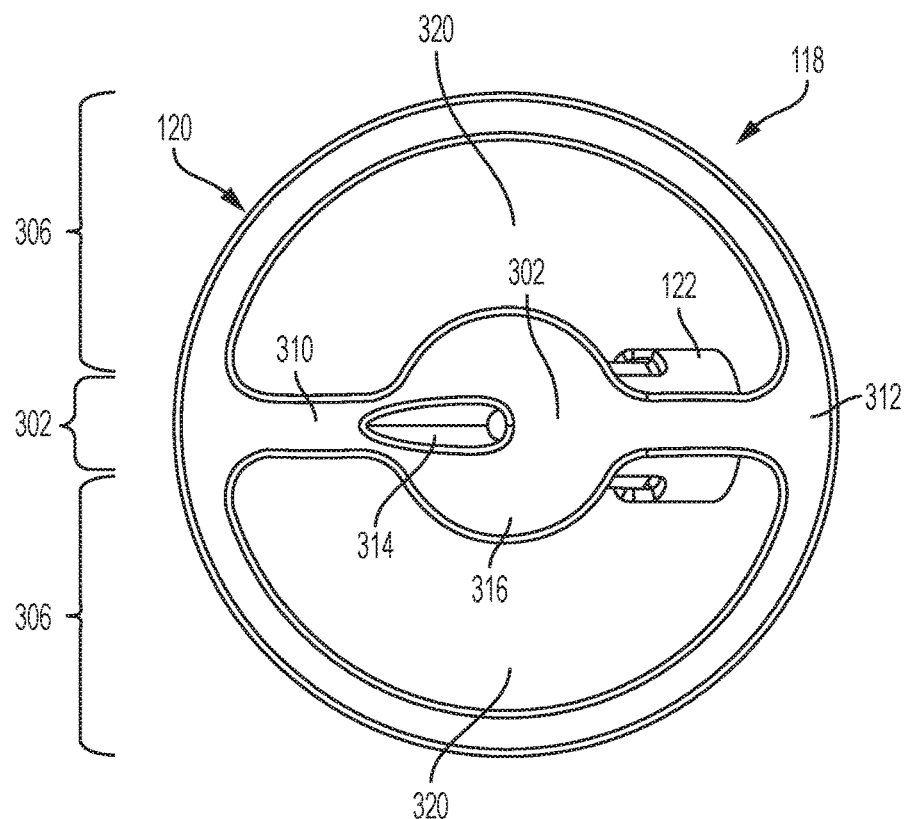

FIGS. 3A and 3B are diagrams showing a perspective view and a bottom view of a support member of the closure device, according to an illustrative embodiment. The base 120 of the support member 118 includes (i) a central portion 302 that connects to column 122 and (ii) one or more lateral support portions 306 extending from the central portion 302. The lateral support portions 306 have support surfaces 308 that retain and/or hold the peripheral portions of the sealable member 106 against the interior surface 108 of the tissue 110. In certain embodiments, the lateral support portion 306 retains and/or holds the peripheral portions and exerts a force that biases the sealable member 106 against the tissue. In certain embodiments, the force is compressive. The lateral support portions 306 in conjunction with the sealable member 106 increase the rigidity of the closure device 100 at regions of contact with the tissue 110, while allowing the closure device 100 to bend during the deployment and during the delivery. The increased rigidity reduces the risk that of inadvertent dislodgment of the closure device 100 after it has been deployed in the body lumen 104, e.g., due to an impact near the closure device or movements of the patient or of inadvertent pull-out of the device 100 (e.g., through the aperture) during its deployment into the body lumen 104.

In some embodiments, the central portion 302 forms a rigid core to which the lateral support portions 306 flexibly connect. In some embodiments, the central portion 302 and the lateral support portions 306 form a single unitary body.

In some embodiments, the lateral support portions 306 forms a gap 320 with respect to the central portion 302.

Still referring to FIGS. 3A and 3B, the central portion 302 of the base 120 includes an anterior support portion 310 and a posterior support portion 312. The contact surfaces 304 of both the anterior and posterior support portions 310, 312 contact and/or press against the anterior and posterior portions of the sealable member 106. The lateral support portions 306 extend from at least one of the anterior support portion 310 and the posterior support portion 312. As shown, the posterior support portion 312, in some embodiments, is disposed proximally to the column 122 of the support member 118, and the anterior support portion 312 is disposed distally to the column 122.

Directionally-Inducted Rigidity of the Devices

In another aspect, the flexible support member 118 may be shaped to provide more rigidity to peripheral portions of the sealable member 106 along a direction to which the sealable member is pulled during the deployment of the closure device 100. The directionally-induced rigidity ameliorates the risk of an accidental pull-out of the sealable member from the lumen 104 during deployment.

Figure 4A:
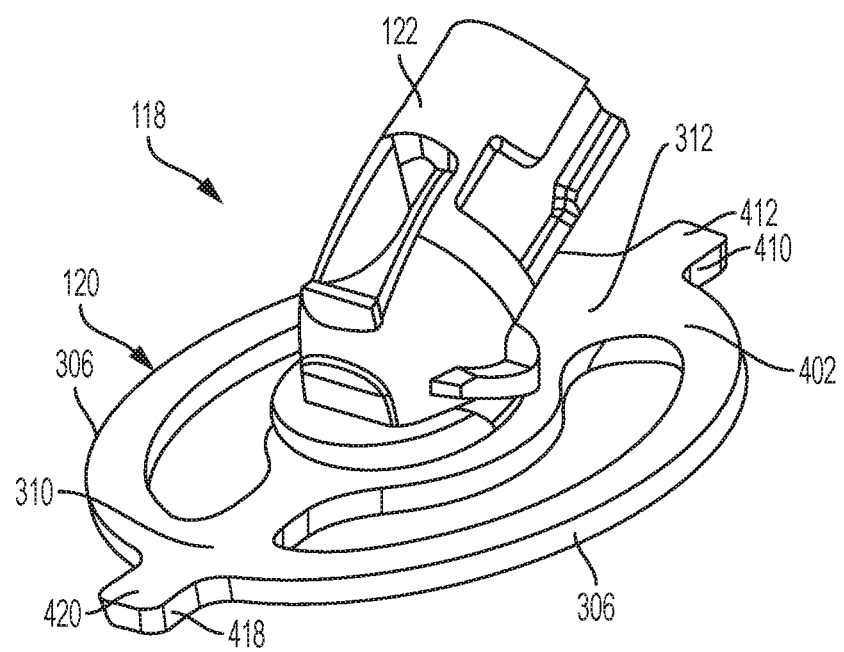
FIGS. 4A and 4B are diagrams showing a perspective view and a bottom view of a support member of the closure device with directionally-induced rigidity, according to an illustrative embodiment.
Figure 4B:
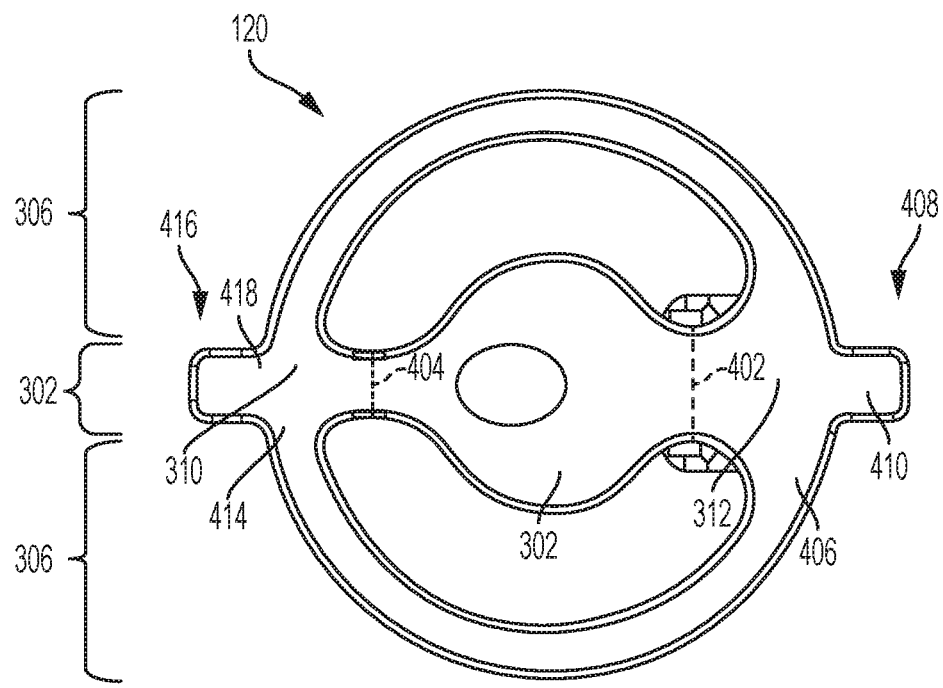

FIGS. 4A and 4B are diagrams showing a support member 118 of the closure apparatus 100 with directionally-induced rigidity. This increased rigidity is employed at a specific part of the base 120 that, preferably, corresponds to the direction of the column 122. In certain embodiments, the base 120 provides more resistance, for example, at region 312, making the portion of the sealable member 106 corresponding to such region subject to less bending. Thus, greater force may be applied to that region of the sealable member 106 before the sealable member 106 would pull through the aperture 112. This reduces the risk that the implant can dislodge from its deployed position due to, for example, movements by the patient and/or impact to the nearby area. The greater force also gives the surgeon a better tactile feel of sealable member 106 during the deployment and creates better apposition of the sealable member 106 against the inner lumen of the body lumen 104. Thus, a faster and more effective seal can be created.

As shown in FIGS. 4A and 4B, the posterior support portion 312 is disposed proximally to the column 122 of the support member 118 and has first maximum cross-sectional area 402. The anterior support portion 310 is disposed distally to the column 122 of the support member 118 and has a second maximum cross-sectional area 404. The first maximum cross-sectional area 402, in certain embodiments, is larger than the second maximum cross-sectional area 404 such that the posterior support portion 312 (and/or adjacent portions of the lateral support member) is more rigid than the anterior support portion 310.

In certain embodiments, the base 120 of the support member 118 has a varying cross-sectional thickness along the direction between the anterior support portion 310 and the posterior support portion 312. The varying thickness along this direction may provide greater rigidity at the posterior support portion 312 of the base 120 than the anterior support portion 310.

Referring still to FIG. 4B, in certain embodiments, the lateral support portions 306 extend from the posterior support portion 312 at a location 406 between (i) a posterior end 408 of the posterior support portion 312 and (ii) the central portion 302, thereby forming a region 410. The region 410 can be characterized as a tab 410 that extends from a perimeter defined by the lateral support portions 306 around the central portion 302. The tab 410 provides additional surface area 412 (see FIG. 4A) to the posterior region of the sealable member 106.

In addition, the lateral support portions 306 may extend from the anterior support portion 310 at a location 414 between an anterior end 416 of the anterior support portion 310 and the central portion 302, thereby forming a region 418. This region 418 can also be characterized as a tab 418. The tab 418 provides additional surface area 420 to the anterior region of the sealable member 106.

Figure 4C:
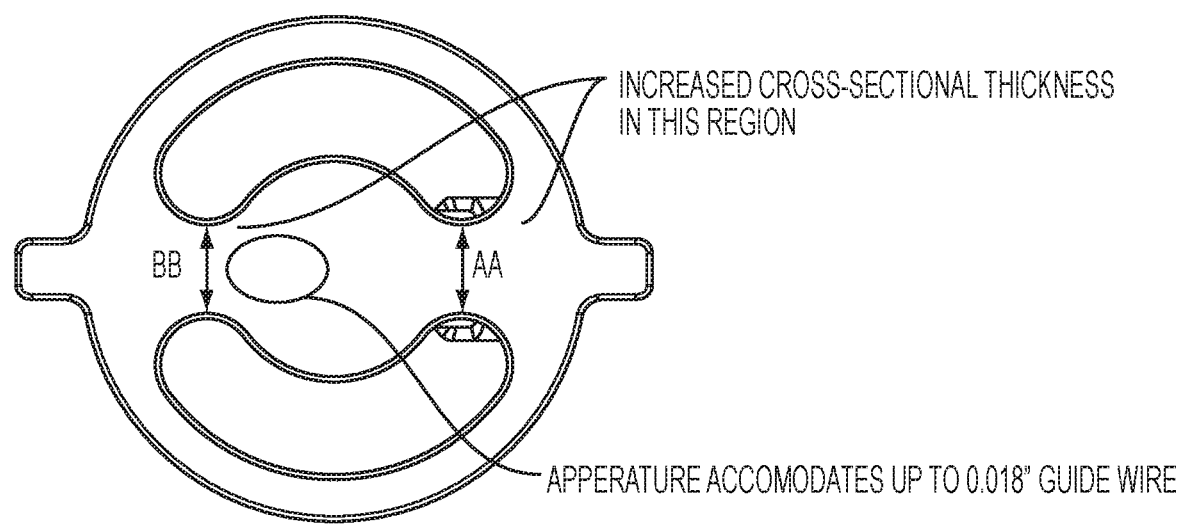
FIG. 4C is a diagram showing a bottom view of a support member of the closure device with directionally-induced rigidity, according to an illustrative embodiment.

In some embodiments, as shown in FIG. 4C, the support member has increased the first maximum cross-sectional area AA and the second maximum cross-sectional area BB. The increased cross-sectional area may provide more rigid support, so that the support member 118 has better user tactic feel. The increased cross-sectional area may reduce risk of dislocation of the supporting member from arteriotomy.

Figure 4D:
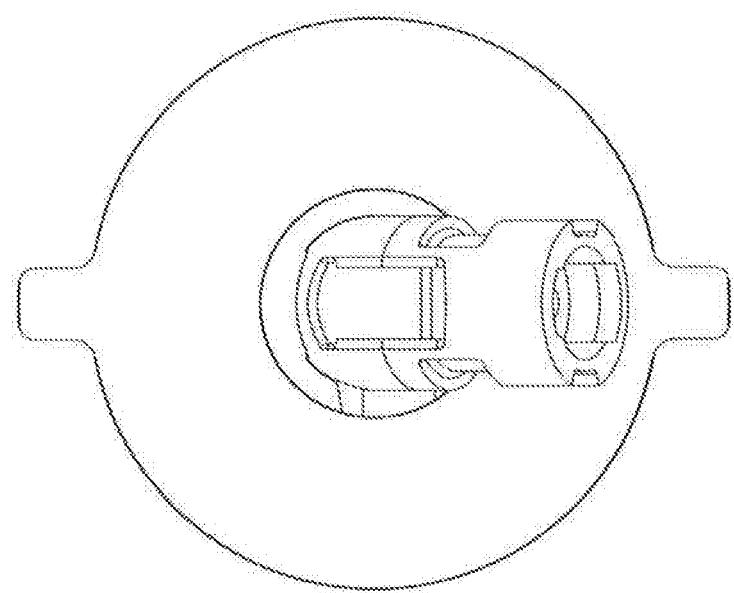
FIGS. 4D and 4E are diagrams showing a perspective view and a bottom view of a support member of the closure device with directionally-induced rigidity, according to an illustrative embodiment.
Figure 4E:
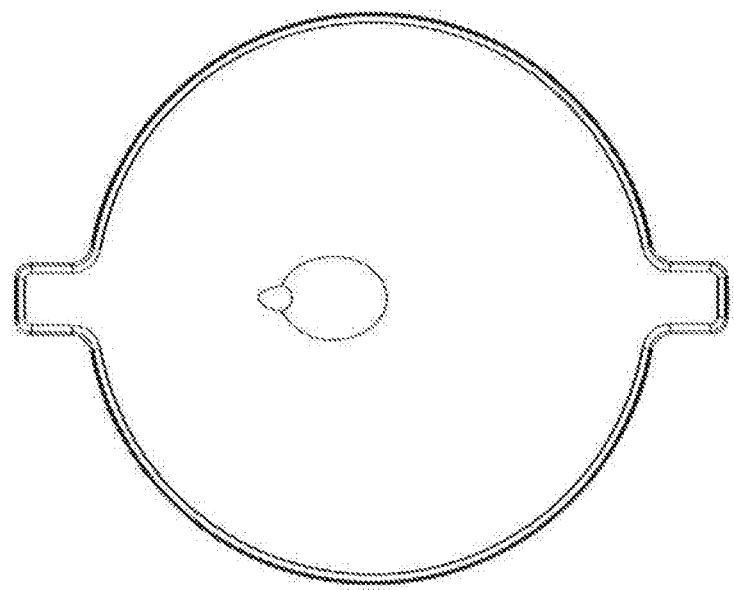

In some embodiments, as shown in FIGS. 4D and 4E, the base may not have a gap between the one or more lateral support portions and the central portion. The continuous surface may facilitate faster endothelial cell coverage and encapsulation when implanted in vivo.

Figure 5:
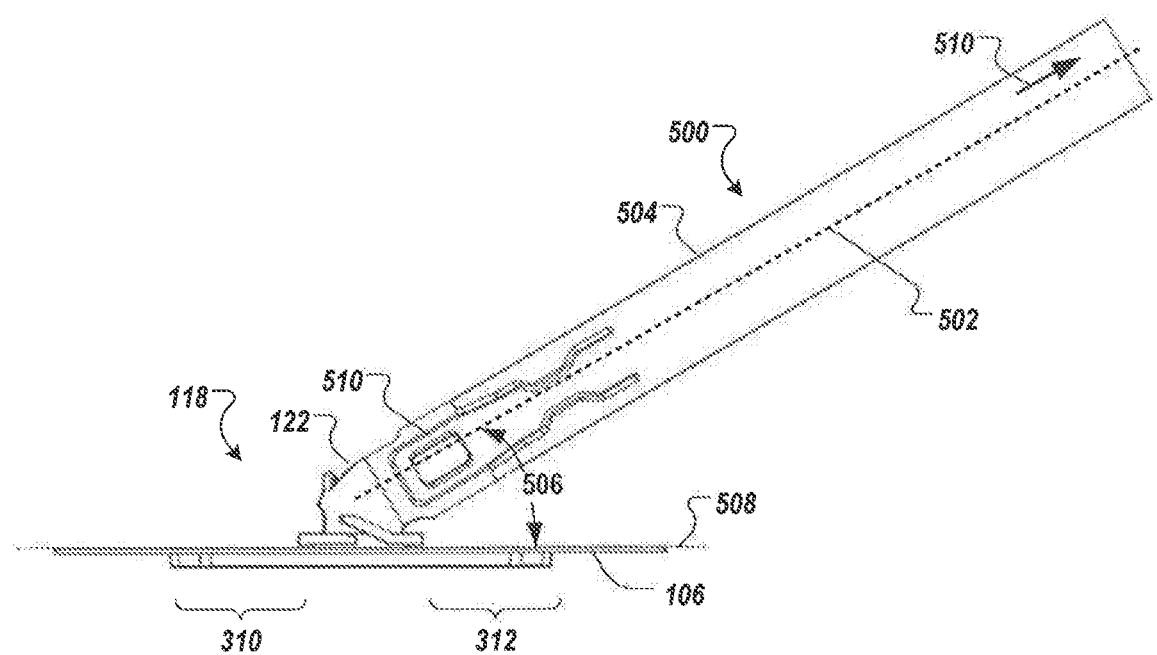
FIG. 5 is a diagram of an example closure device (e.g., of FIG. 7) secured to a delivery apparatus.

FIG. 5 is a diagram of an example closure device 100 secured to a delivery apparatus 500 of the device 100. The apparatus 500 is equipped with an appropriate docking mechanism for a given closure device 100. In certain embodiments, the docking mechanism comprises a T-shaped engagement arm that engages a corresponding recess on the closure device 100. In some embodiments, the recess and engagement arms may include a pin or protrusion, e.g., for alignment.

As shown, the column 122 of the support member 118 is angularly disposed, when secured to the apparatus 500, along an axis 502 corresponding to a longitudinal axis of a delivery shaft 504 to which the closure device 100 is releasably attached. The delivery shaft 504 may engage the column 122, in some embodiments, at two recesses 510 located on the proximal tip of the column 122. In certain embodiments, the column 122 forms an angle 506 between a plane 508 corresponding to the sealable member 106 in a rest configuration and the longitudinal axis 502 of the delivery shaft 504. In certain embodiments, the angle 506 is between about 10 degrees and about 70 degrees, including, but not limited to, 10, 15, 20, 25, 30, 35, 40, 45, 50, 55, 60, 65, and 70 degrees.

Additional examples of the delivery apparatus is found in U.S. Patent Application Publication No. US 2014/0018846, titled "Implants and Methods for Percutaneous Perforation Closure," the content of which is incorporated herein in its entirety.

Examples of the Support Member

Various embodiments of the lateral support portions are now described. In some embodiments, the lateral support portions 306 extend from the central portion 302 to form a continuous structure, for example, but not limited to, a ring (e.g., circle, oval, rectangular, ellipse, diamond) around the central portion 302 of the base 120. In other embodiments, the lateral support portions 306 form one or more cantilevers that extend from the central portion 302. FIGS. 6-16 are diagrams showing perspective views of other exemplary embodiments of the support members 118.

Figure 6:
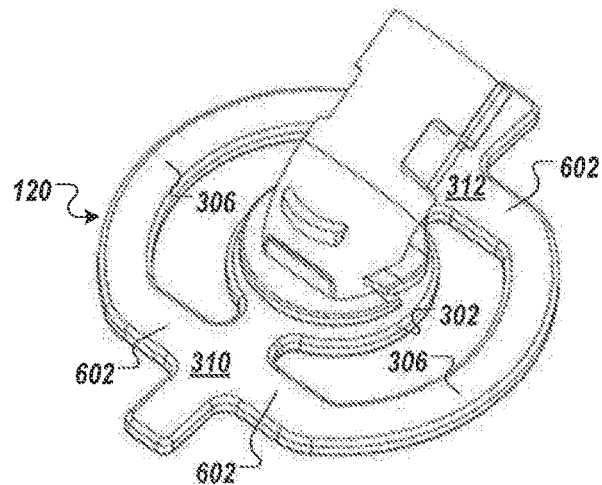
FIGS. 6-16 are diagrams showing perspective views of alternative embodiments of the support members.

As shown in FIGS. 6-9, the lateral support portions 306 form a continuous structure around the central portion 302. Specifically, as shown in FIG. 6, the lateral support member 306 forms a straight connection region 602 that extends from the anterior support portion 310 and the posterior support portion 312 of the base 120.

Figure 7:
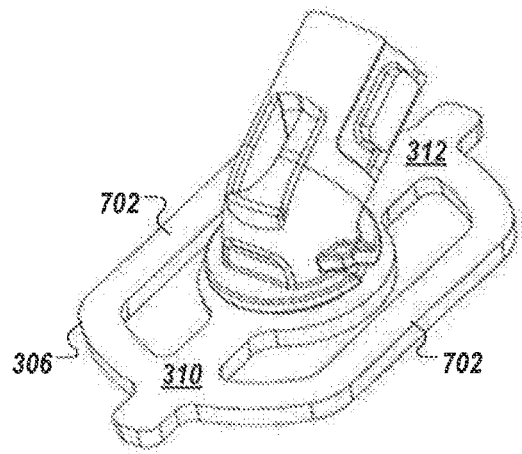

As shown in FIG. 7, each of the lateral support members 306 forms a straight support region 702. Each of the straight support regions 702 is parallel to the anterior support portion 310 and the posterior support portion 312 of the base 120.

Figure 8:
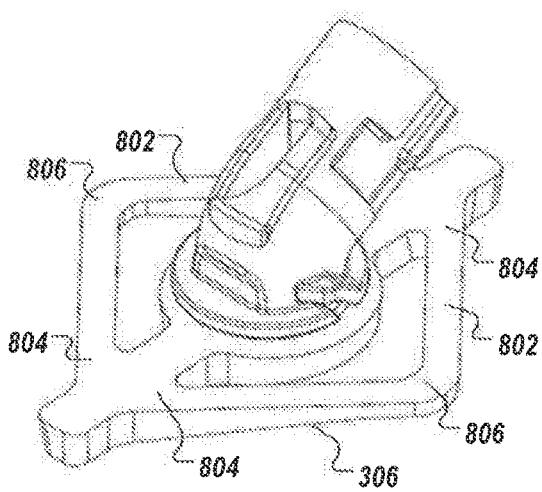

As shown in FIG. 8, the lateral support member 306 forms a diamond-shaped support region 802. In certain embodiments, the diamond-shaped support region 802 has a uniform cross-sectional thickness. In other embodiments, the diamond-shaped support region 802 has a varying cross-sectional thickness in which the thickness is greater at the point of connection 804 than at the peripheral portion 806.

Figure 9:
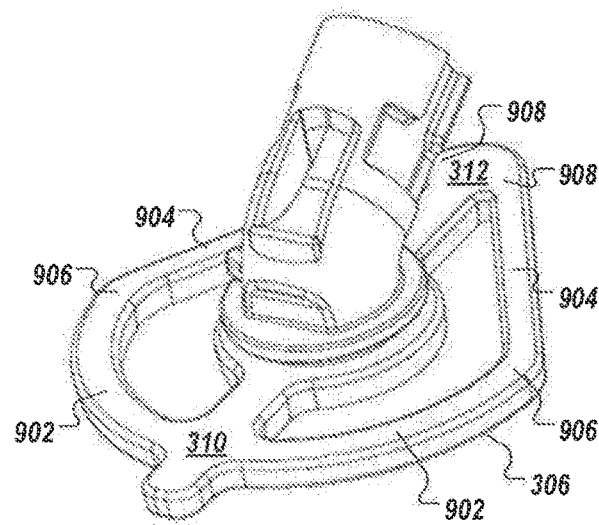

As shown in FIG. 9, the lateral support member 306 has a wide base at one region, which then tapers to a point of connection with the central portion 302. As shown, a protruded region 902 extends from the anterior support portion 310. The protruded region 902 then tapers to the point of connection 908. This shape can be characterized as a snow shoe or a leaf. Alternatively, in certain embodiments, the protruded region 902 extends from the posterior support portion 312, and the taper region 904 extends from the anterior support portion 310.

Figure 10:
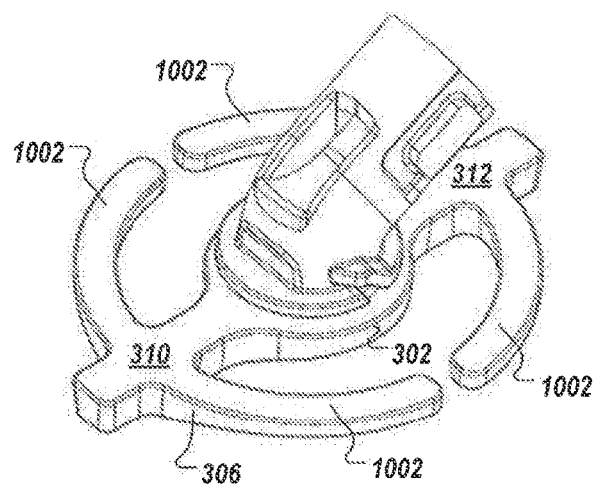
Figure 11:
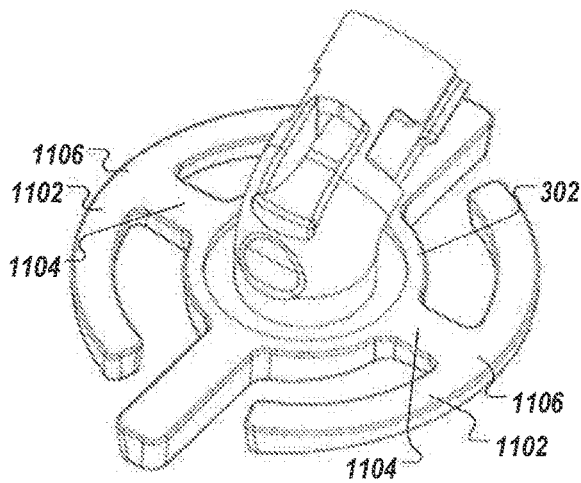
Figure 12:
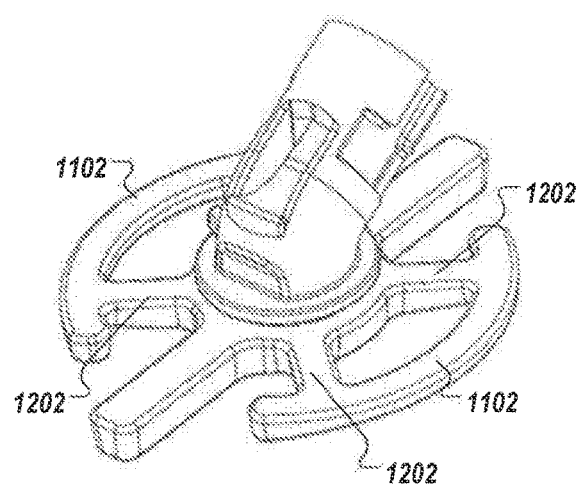

As shown in FIGS. 10 to 12, each of the lateral support portions 306 forms a non-continuous structure around the central portion 302. Specifically, in FIG. 10, the lateral support member 306 forms an arcuate structure 1002 around the central portion 302. Each of arcuate portions 1002 extends from the anterior support portion 310 and the posterior support portion 312 of the base 120 of the support member 118.

In FIGS. 11 and 12, each of the lateral support members 306 also forms an arcuate portion 1102 around the central portion 302. The arcuate portion 1102 has a connection region 1104 that extends from the central portion 302 of the base 120. In FIG. 11, each of the arcuate portions 1102 has a single connection region 1104. In FIG. 12, each of the arcuate portions 1102 has a plurality of connection regions 1202.

Referring still to FIGS. 11 and 12, in certain embodiments, the cross-sectional thickness of the base 120 is varied between the central portion 302 and the peripheral regions 1106 of the lateral support portions 306.

Figure 13:
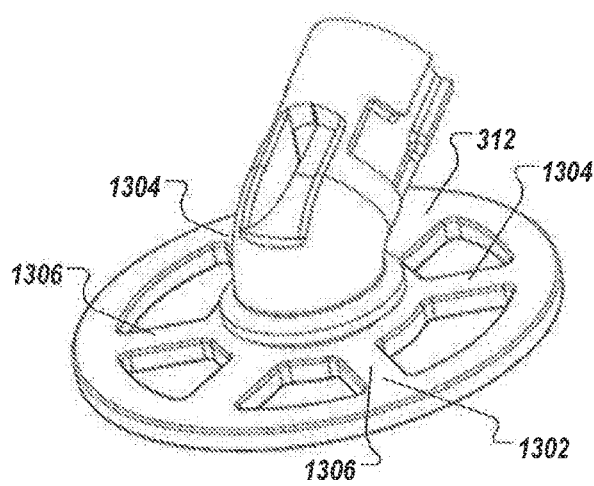

In FIG. 13, the lateral support portions 306 form a continuous structure around and connected through the central portion 302. The structure can be characterized as a wagon wheel. In such embodiments, the lateral support portion 306 have between 4 and 20 connection regions 1302. In certain embodiments, the connection regions 1302 are uniformly spaced apart from each other. In other embodiments, the spacing between the connection regions 1302 is varying. For example, the connection regions 1304 proximally located to the posterior support portion 312 may be spaced more closely to one another than connection regions 1306 distally located to the posterior support portion 312.

Figure 14:
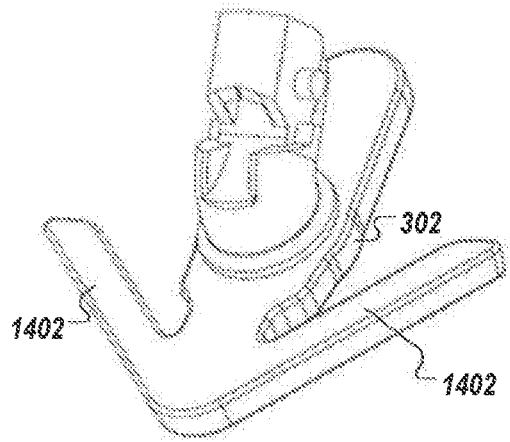
Figure 15:
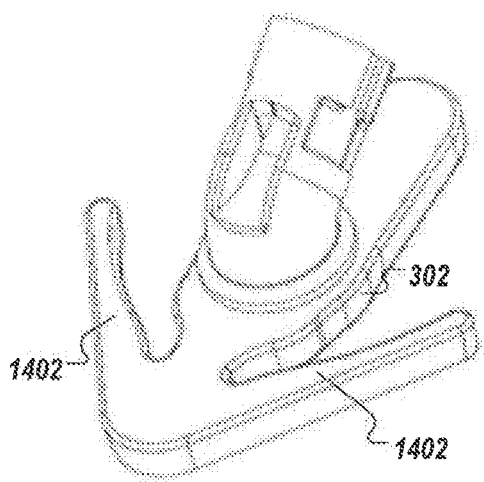

In FIGS. 14 to 15, the lateral support portions 306 form one or more cantilevers 1402 that extend from the central portion 302 (or the anterior support portion). In some embodiments, the cantilevers 1402 have a uniform cross-sectional thickness (see FIG. 14). In other embodiments, the cantilevers 1402 have a varying cross-sectional thickness (see FIG. 15).

Figure 16:
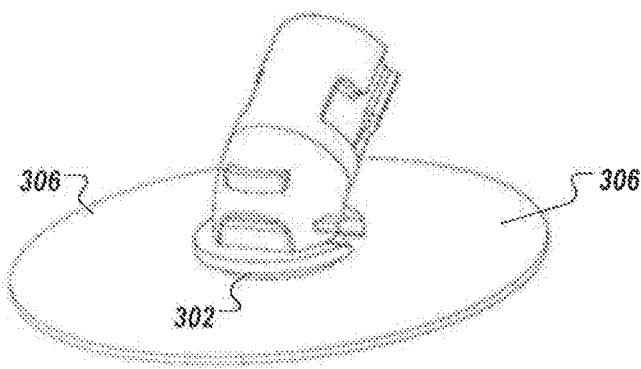

In FIG. 16, the lateral support portions 306 form a continuous surface with the central portion 302. The structure can be characterized as a disc.

Additional views of the various embodiments, as well as further examples of the closure device 100, are provided in FIGS. 23A-72C.

Other Components of the Closure Device

Referring back to FIG. 3A, the column 122 of the support member 118, in some embodiments, has an engagement portion 124 to secure the guard member 126 (e.g., an insertable or engagable pin or cage in FIG. 18A) to the support member 118. In some embodiments, the guard member 126 is maintained at a location relative to the exterior surface 116 of the tissue 110 when the closure device 100 is in the sealing position. In some embodiments, the guard member 126 compresses against the exterior surface 116 of the tissue 110 when the closure device 100 is in the sealing position. In some embodiments, the guard member 126 is moveable, from a stowed state to a deployed state, to engage exterior surface 116 of the tissue adjacent the aperture such that a portion of the tissue is disposed between the guard member 126 and the sealable member 106 when the closure device 100 is in the sealing position. In certain embodiments, and as shown in FIG. 3A, the engagement portion 124 comprises a cavity 124 in the column 122 to allow an extra-luminal pin (as the guard member 126) to be inserted therethrough.

Examples of the extra-luminal pin are described U.S. Patent Application Publication No. US 2014/0018847, titled "Percutaneous Perforation Closure Systems, Devices, and Methods." In other embodiments, the engagement portion 124 is a protrusion or a recess on the exterior surface of the column 122 to which a slotted cage or shoe (as a guard member) can engage.

In certain embodiments, the base 120 of the support member 118 has a uniform thickness between about 0.1 mm and about 1.5 mm, including 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1.0, 1.05, 1.10, 1.15, 1.20, 1.25, 1.30, 1.35, 1.40, 1.45, and 1.5 mm. In other embodiments, the thickness is varying.

The sealable member 106, in some embodiments, is sized to be larger than the diameter of the aperture (e.g., between 12 F and 30 F). In some embodiments, the sealable member 106 has a thickness preferably between about 0.05 mm and about 0.6 mm. In some embodiments, the sealable member 106 has a thickness between about 0.005 mm and 4 mm, e.g., depending on the size of the aperture and the size of the vessel/lumen.

In certain embodiments, the thickness of the sealable member and/or support member, as deployed in the vessel/lumen, is selected based on the size of the aperture to be sealed and/or the size of the blood vessel/hollow vessel. Table 1 lists exemplary ranges of thicknesses of a sealable member to close an aperture based on the aperture/incision size that is formed. Table 2 lists exemplary ranges of thicknesses of the sealable member to close an aperture based on the vessel diameter size. Table 3 lists exemplary ranges of thicknesses of sealable member to close an aperture base on the size of the hollow vessel.

TABLE 1

Example thicknesses of a sealable member for closure of a blood vessel (e.g., having an internal diameter between about 6 and 12 mm), selected based on the incision/puncture size at the blood vessel.

|  |  | Sealable Member Thickness (mm) | |
| --- | --- | --- | --- |
| French size | Hole Size (mm) | Min | Max |
| 6 | 2 | 0.04 | 0.5 |
| 9 | 3 | 0.04 | 0.75 |
| 12 | 4 | 0.04 | 1 |
| 15 | 5 | 0.04 | 1.5 |
| 18 | 6 | 0.04 | 2 |
| 21 | 7 | 0.04 | 2.5 |
| 24 | 8 | 0.04 | 3 |
| 27 | 9 | 0.04 | 4 |

TABLE 2

Example thicknesses of a sealable member for closure of a blood vessel, selected based on the size of the blood vessel.

| Vessel Size | Sealable Member Thickness (mm) | |
| --- | --- | --- |
| (Internal Diameter, mm) | Min | Max |
| 5 | 0.04 | 0.5 |
| 6 | 0.04 | 0.75 |
| 7 | 0.04 | 1 |
| 9 | 0.04 | 1.5 |
| 11 | 0.04 | 2 |
| 15 | 0.04 | 3 |
| 20 | 0.04 | 3.5 |
| 30 | 0.04 | 4 |

TABLE 3

Example thicknesses of a sealable member for closure of a non-blood carrying hollow vessel (e.g., having an internal diameter between 15 and 100+ mm), selected based on the size of the hollow vessel.

| Vessel Size | Sealable Member Thickness (mm) | |
| --- | --- | --- |
| (Internal Diameter, mm) | Min | Max |
| 15 | 0.04 | 3 |
| 40 | 0.04 | 8 |
| >100 | 0.04 | 20+ |

The sealable member 106 is preferably circular in shape. It should be understood, however, that other geometries may be provided for the hole and/or the disk portion, including, but not limited to, ovals. The sealable member 106 has a hole (e.g., located at or near the center of the member) sized to accept the column 122. In some embodiments, the sealable member 106 is free to rotate relative to the base 120 of the support member 118 about an axis concentric to the column 122. Other examples of the sealable member is described in U.S. Patent Application Publication No. US 2014/0018847, titled "Percutaneous Perforation Closure Systems, Devices, and Methods," and U.S. Provisional Application No. 62/092,212, titled "Implantable Sealable Member with Mesh Layer," the content of each of these applications is incorporated by reference herein in its entirety.

The sealable member and/or the base comprises, in some embodiments, at least one material selected from the group consisting of Polydioxanone, Poly-L-lactide, Poly-D-lactide, Poly-DL-lactide, Polyglycolide, ε-Caprolactone, Polyethylene glycol, and a copolymer thereof. In some embodiments, the material of the sealable member and/or the base is a copolymer of Polydioxanone, Poly-L-lactide, Poly-D-lactide, Poly-DL-lactide, Polyglycolide, ε-Caprolactone, and Polyethylene glycol. In some embodiments, the copolymer includes (a) monomers of Polydioxanone, Poly-L-lactide, Poly-D-lactide, Poly-DL-lactide, Polyglycolide, ε-Caprolactone, or Polyethylene glycol, and (b) one or more additional monomers. In some embodiments, the (a) and (b) monomers form a polymer that is bioabsorbable. One of ordinary skill in the art will appreciate that other suitable biodegradable material may be employed.

In certain embodiments, the thickness of the support member 118 and the sealable member 106 are selected such that the members 106, 118 are bendable to be loaded into the cannula 2202 while having sufficient rigidity to form and maintain a tamponade at the aperture when the device 100 is in the sealing position. In some embodiments, the thickness of the support member 118 and the sealable member 106 are selected such that a portion of the members 106, 118 is rigid.

Figure 21A:
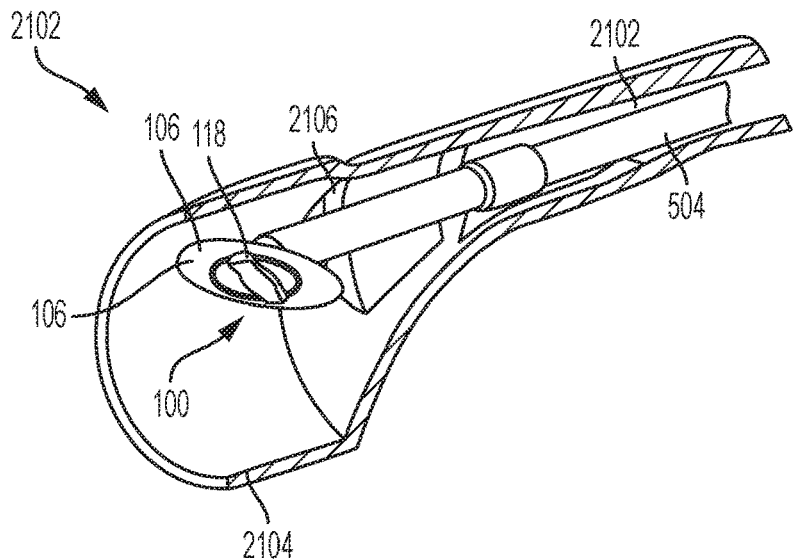
FIGS. 21A, 21B, and 21C are diagrams showing a sequence of the transition of the sealable member and the support member from a stowed state to a delivery state when the closure apparatus is loaded in a delivery cannula.
Figure 21B:
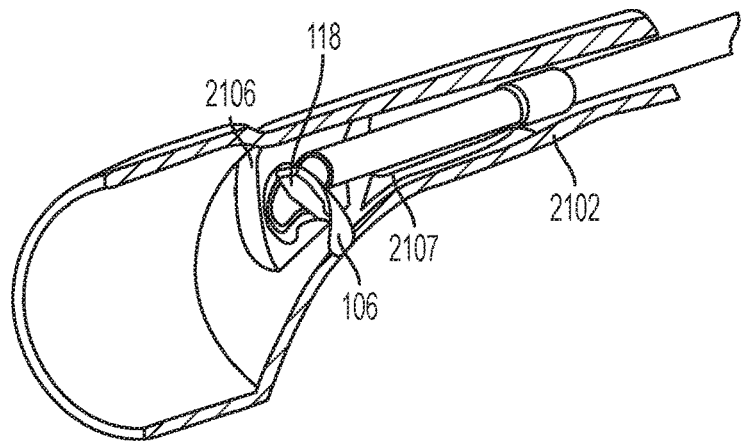
Figure 21C:
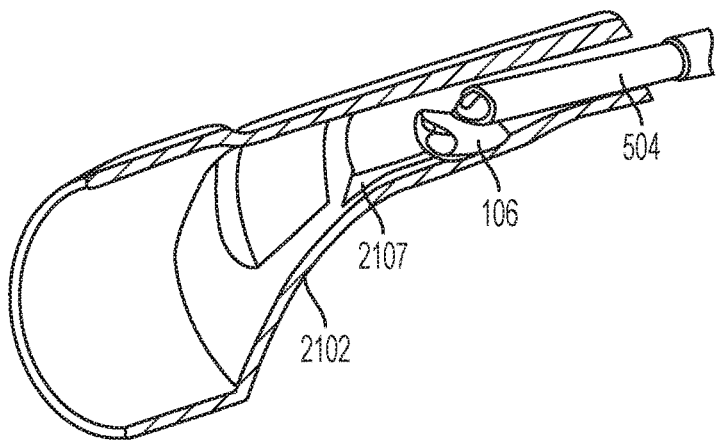

In some embodiments, the base 120 of the support member 118 is sufficiently flexible to roll into a delivery funnel used for delivering the implant into the body lumen. FIGS. 21A, 21B, and 21C are diagrams showing a sequence of the transition, in some embodiments, of the sealable member and the support member from a stowed state to a delivery state when the closure apparatus is loaded in a delivery cannula.

In some embodiments, during deployment to close a hole, e.g., in a hollow vessel, the implant 100 is loaded into a delivery cannula 2102 through a loading funnel 2102 which reduces the cross-sectional area of the implant 100 (e.g., support member 118 and sealable member 106) to make it possible to deliver the implant through an introducer catheter into a hollow vessel (such as an artery or a vein) within which there had been made an access hole to perform a minimally invasive procedure. During this delivery and deployment of the implant, the support member 118 (e.g., O-ring foot core) supports the wing.

As shown in FIG. 21A, the device 100 is in an open configuration. The sealable member 106 and the base 120 are in a resting state. It should be appreciated that in certain embodiments, the base 120 may be pre-loaded to bias the sealable member 106 when in the resting state.

FIG. 21B shows the sealable member 106 and the base 120 of the support member 118 progressively folded down as they pass proximally through a narrowing zone 2106 of the funnel 2102. In certain embodiments, the narrowing zone 2106 includes a first offset surface to initiate folding of the sealable member 106 along one of its side. A second offset surface then initiates folding of the other side as the support member 118 continues to pass through the funnel 2102. The different initiation of the folding of the base 120 and sealable member 106 ensures that they fold in an overlapping manner. In some embodiments, the funnel 2102 includes a third surface 2107.

Figure 22:
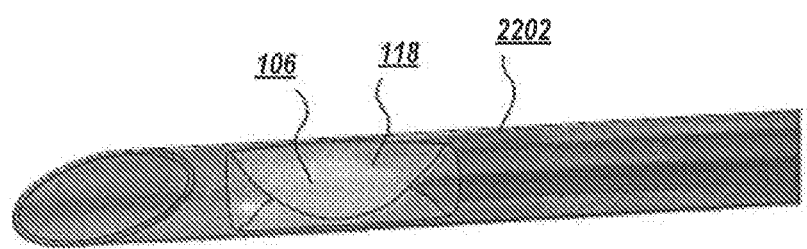
FIG. 22 is a diagram of the sealable member and the support member in the delivery configuration.
Figure 23A:
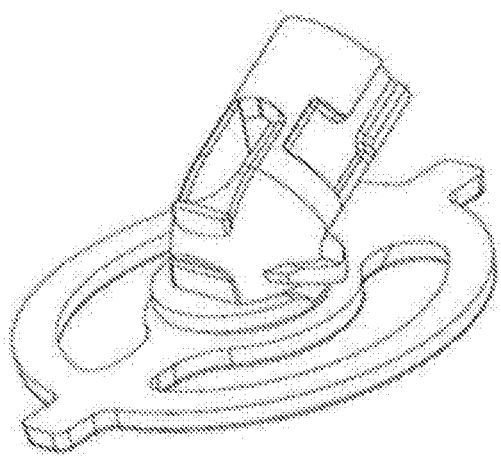
Figure 23B:
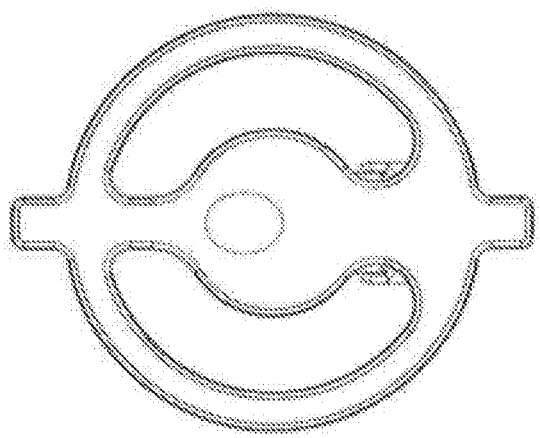
Figure 23C:
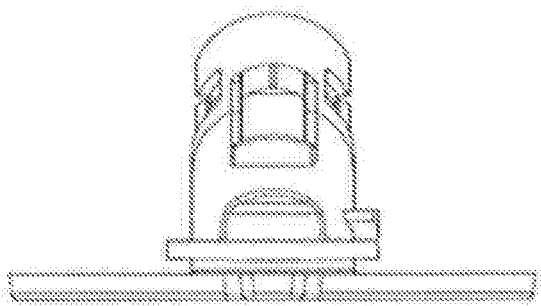
Figure 23D:
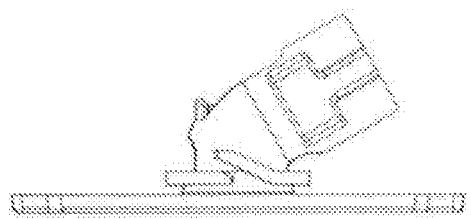
Figure 24A:
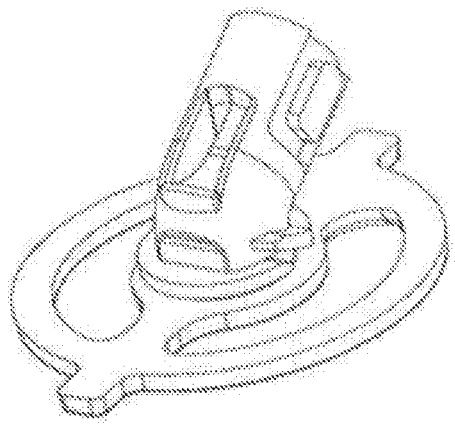
Figure 24B:
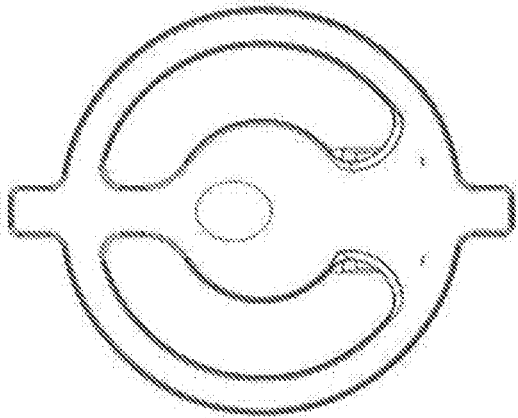
Figure 24C:
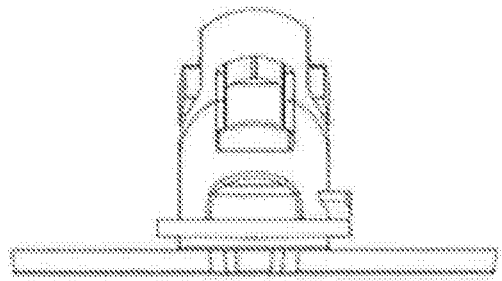
Figure 24D:
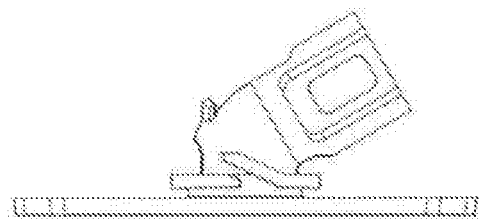
Figure 25A:
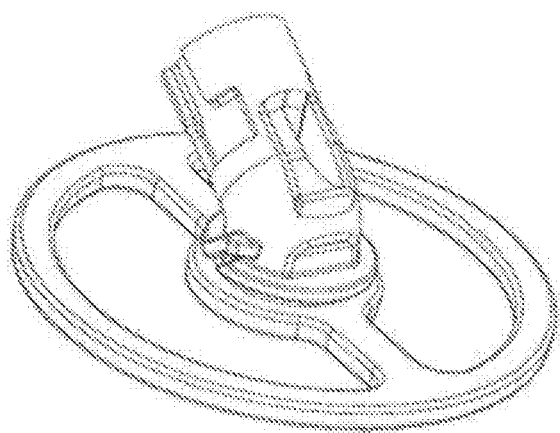
Figure 25B:
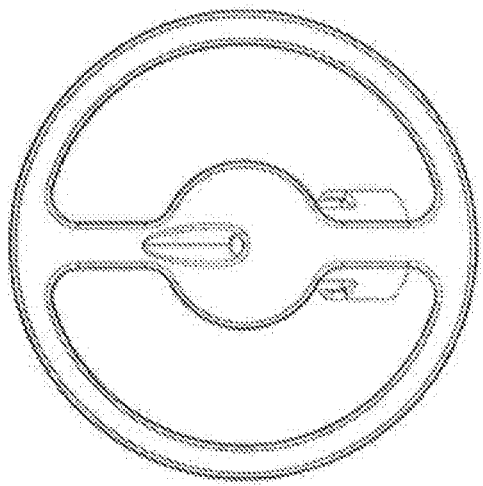
Figure 25C:
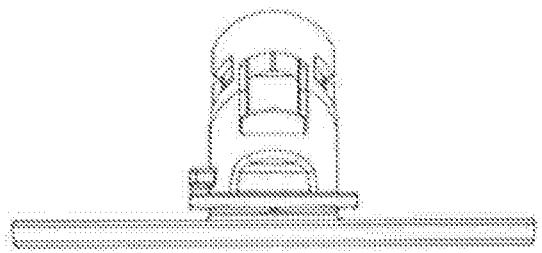
Figure 25D:
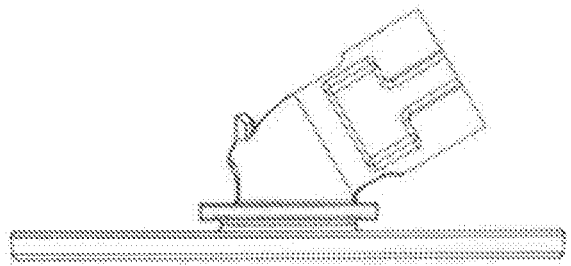
Figure 26A:
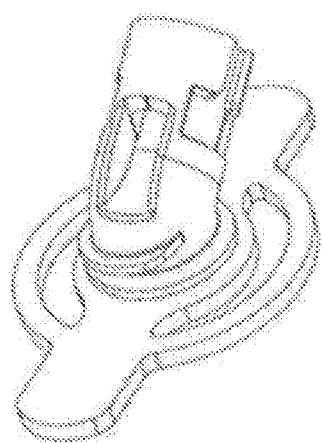
Figure 26B:
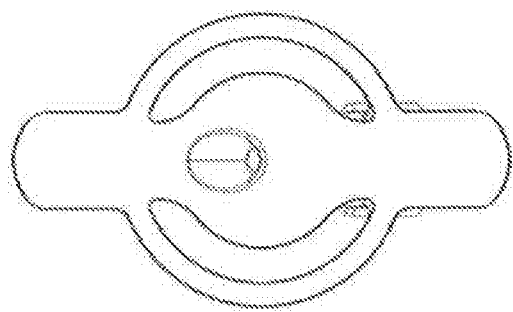
Figure 26C:
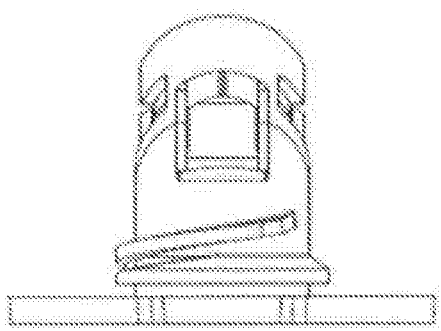
Figure 26D:
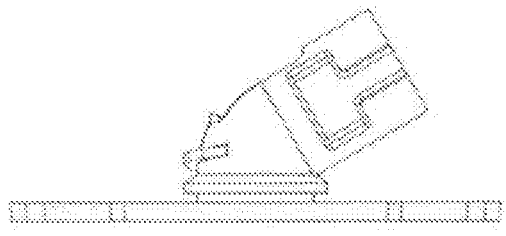
Figure 27A:
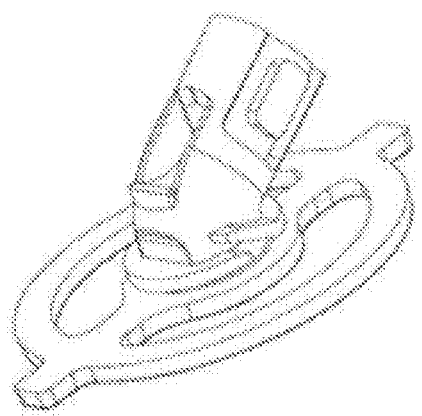
Figure 27B:
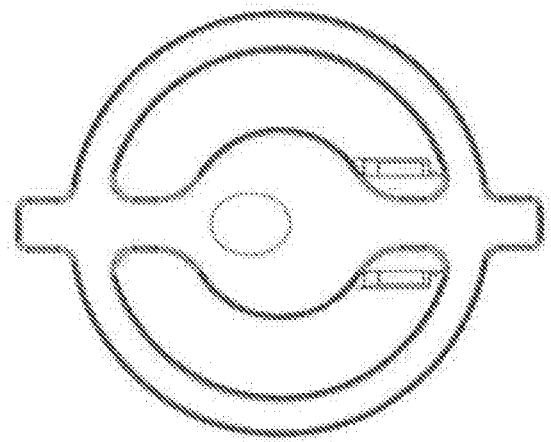
Figure 27C:
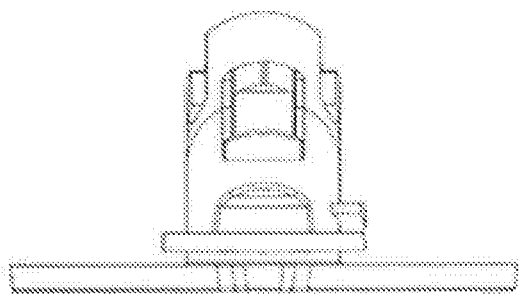
Figure 27D:
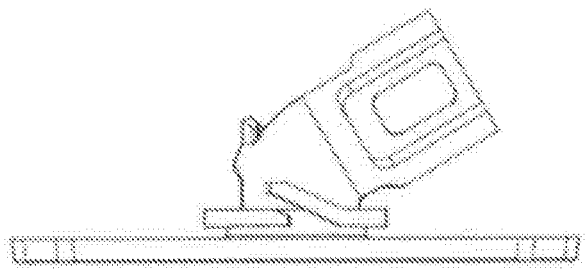
Figure 31A:
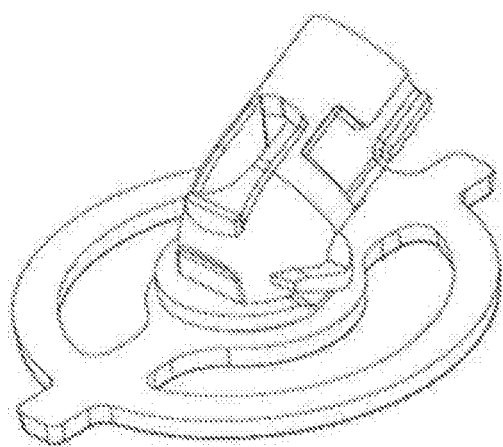
Figure 31B:
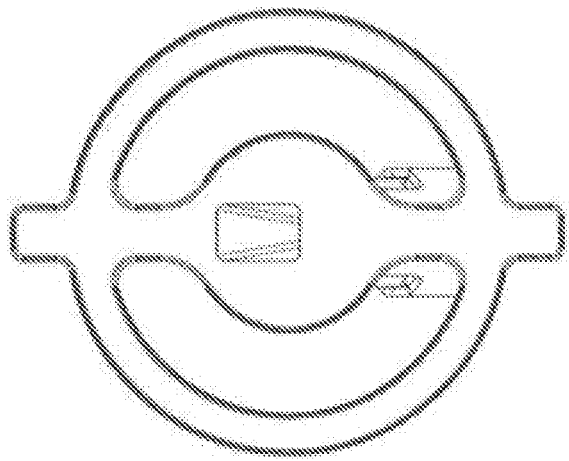
Figure 31C:
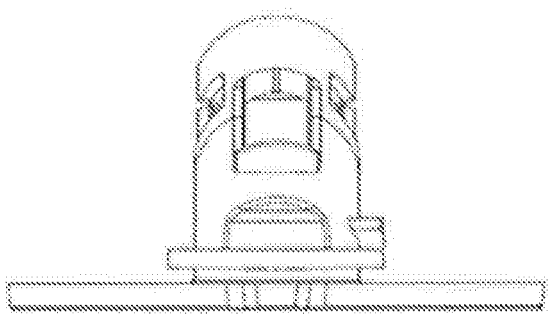
Figure 31D:
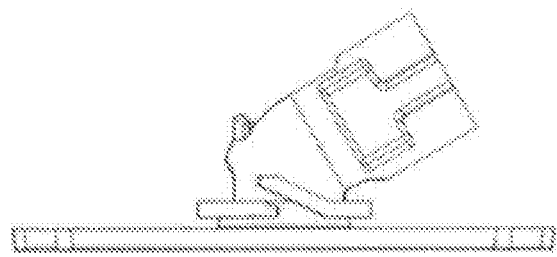
Figure 32A:
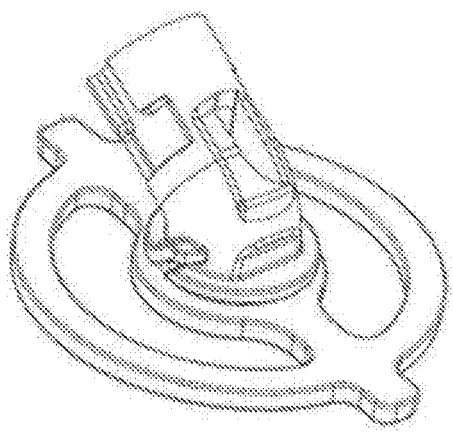
Figure 32B:
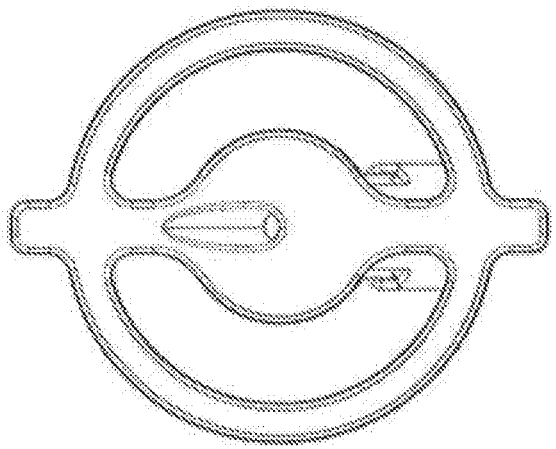
Figure 32C:
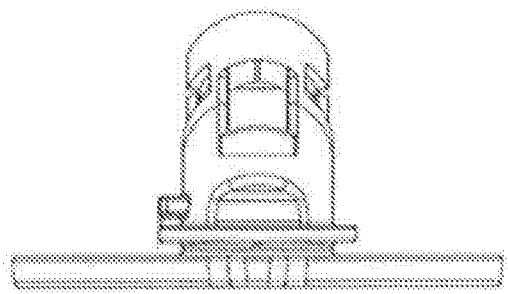
Figure 32D:
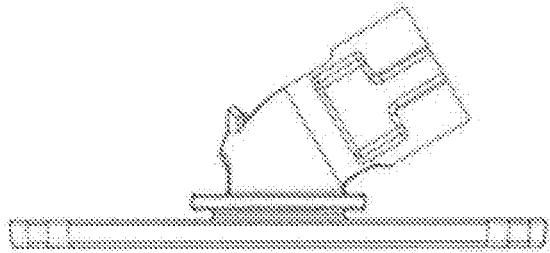
Figure 33A:
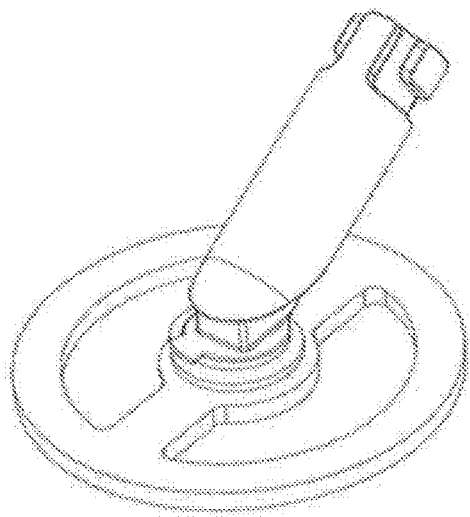
Figure 33B:
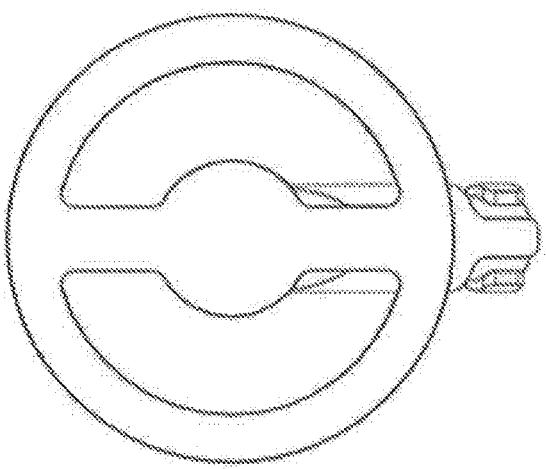
Figure 33C:
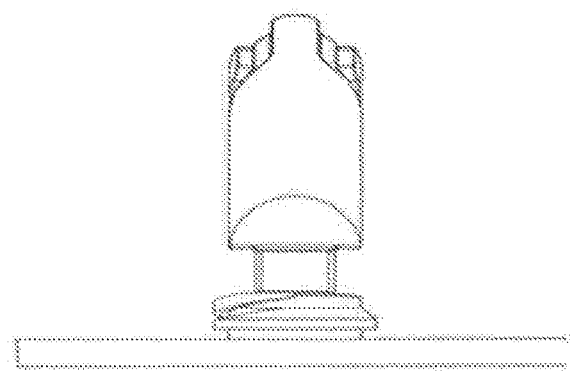
Figure 33D:
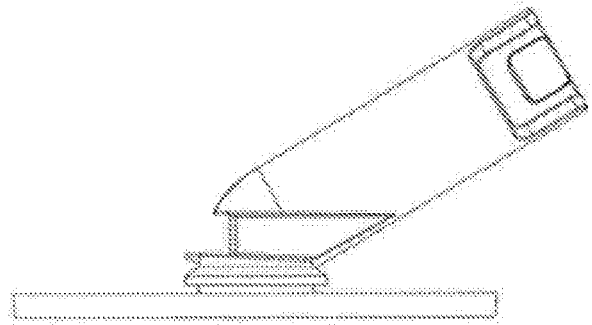
Figure 34A:
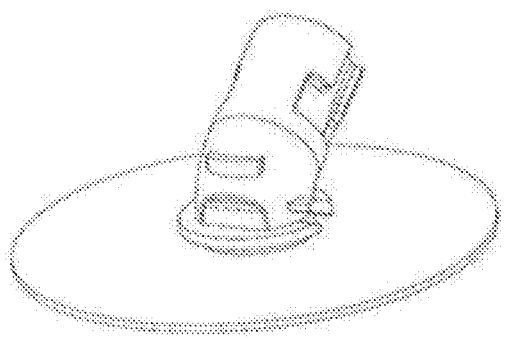
Figure 34B:
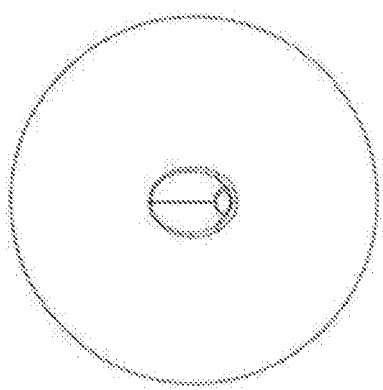
Figure 34C:
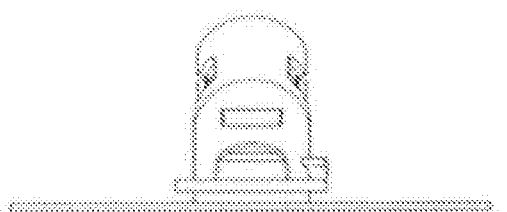
Figure 34D:
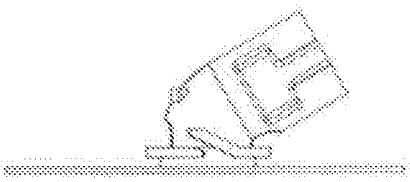
Figure 35A:
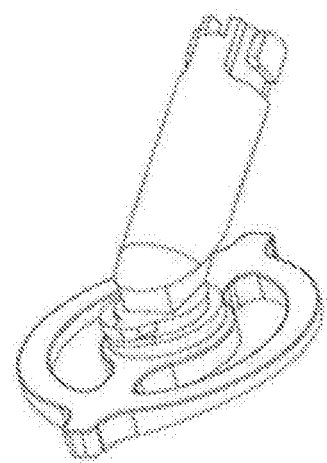
Figure 35B:
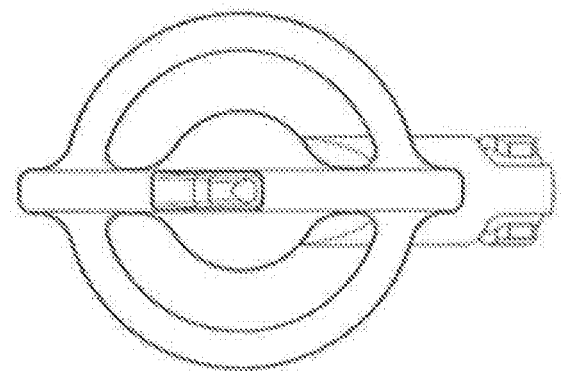
Figure 35C:
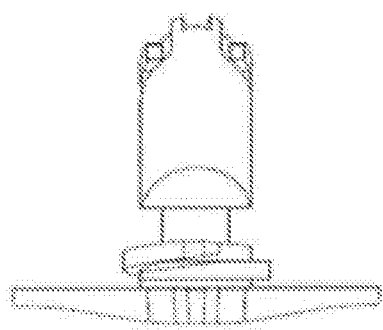
Figure 35D:
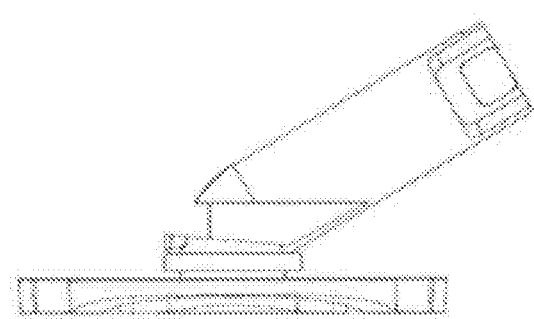
Figure 36A:
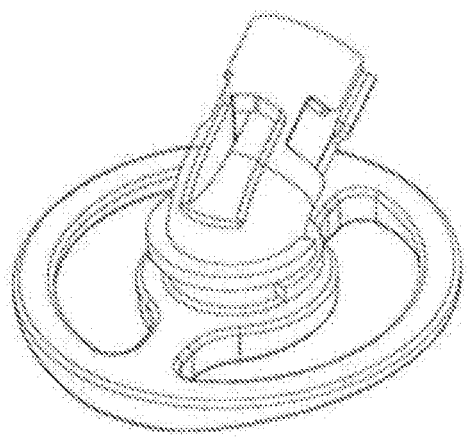
Figure 36B:
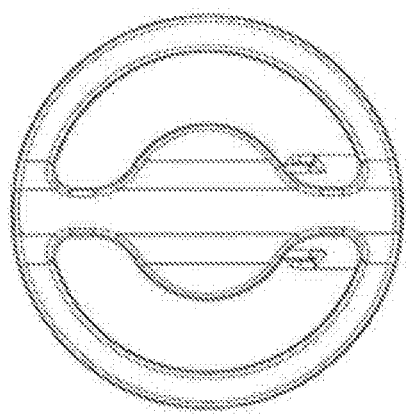
Figure 36C:
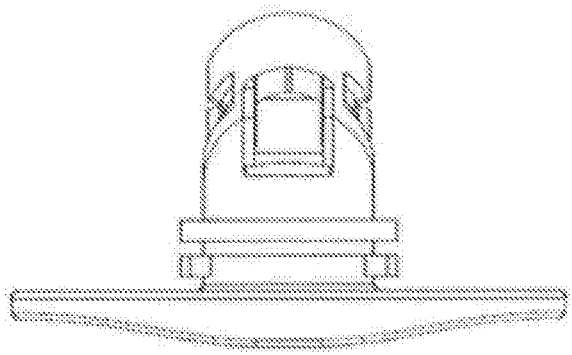
Figure 36D:
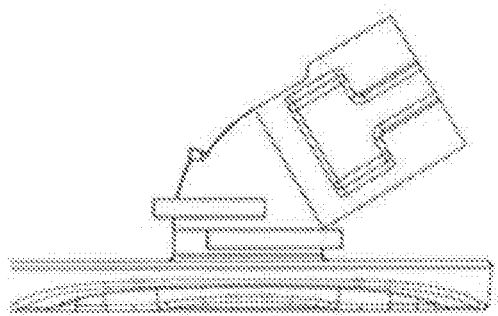
Figure 37A:
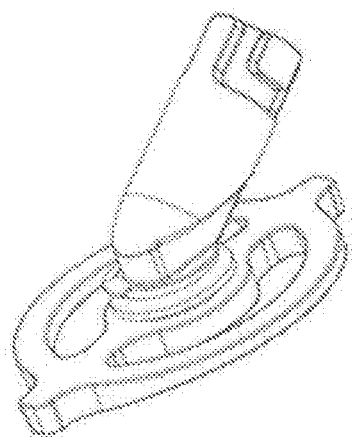
Figure 37B:
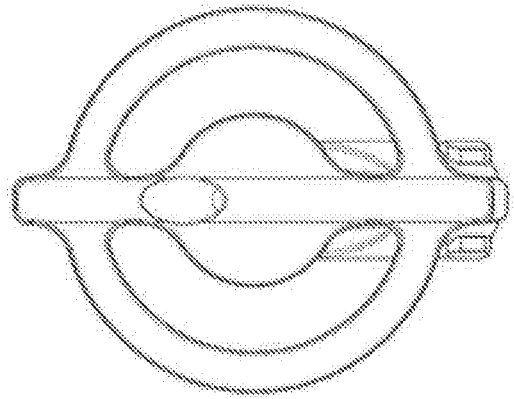
Figure 37C:
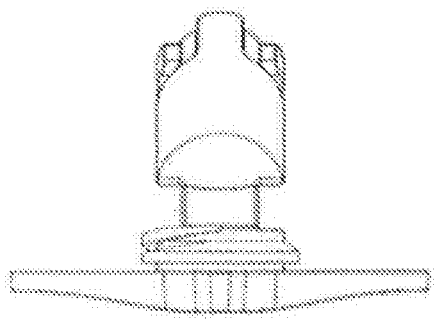
Figure 37D:
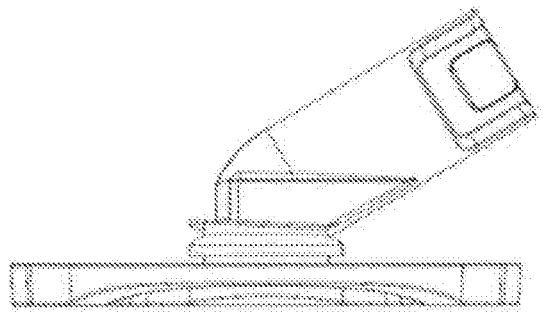
Figure 38A:
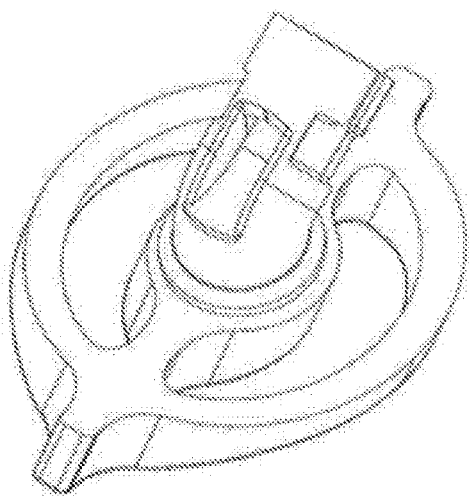
Figure 38B:
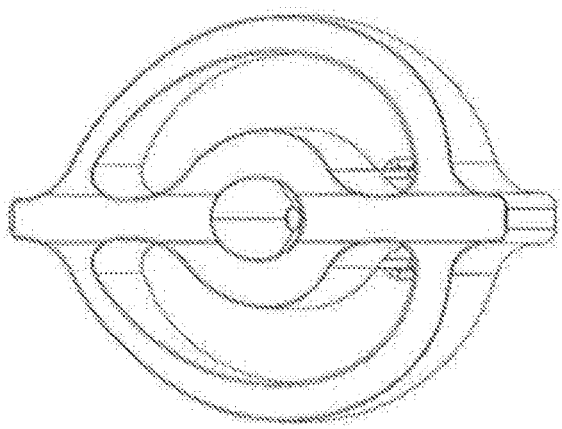
Figure 38C:
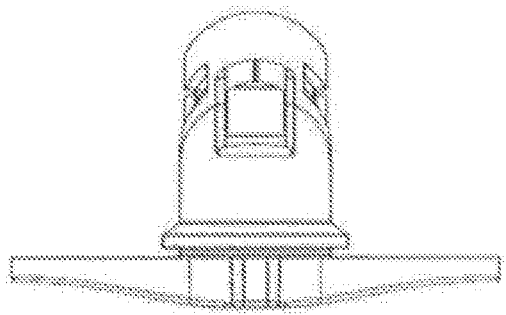
Figure 38D:
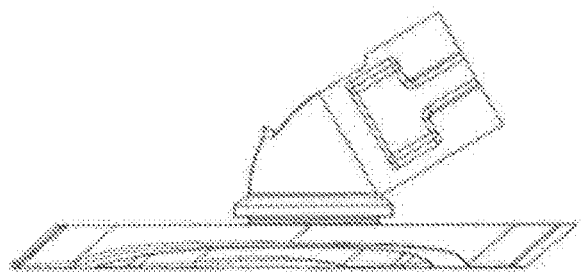
Figure 39A:
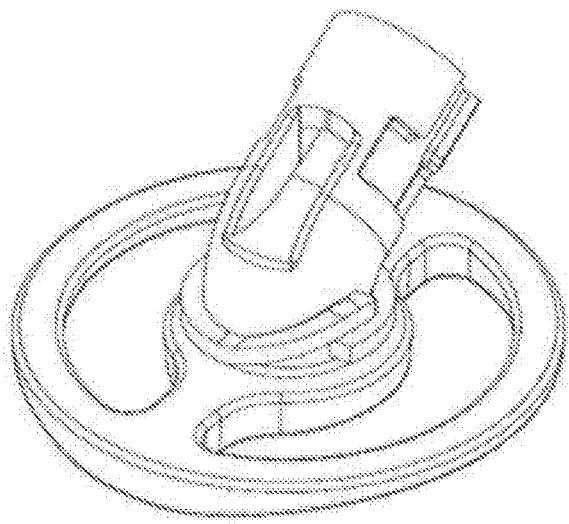
Figure 39B:
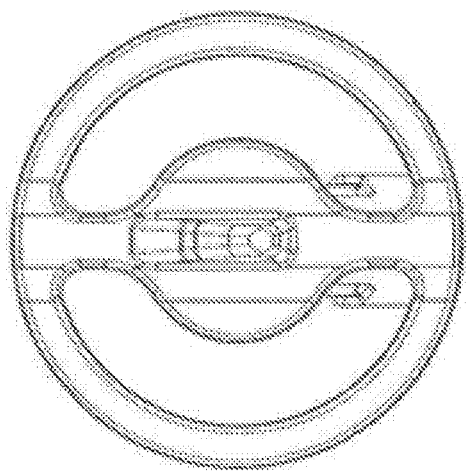
Figure 39C:
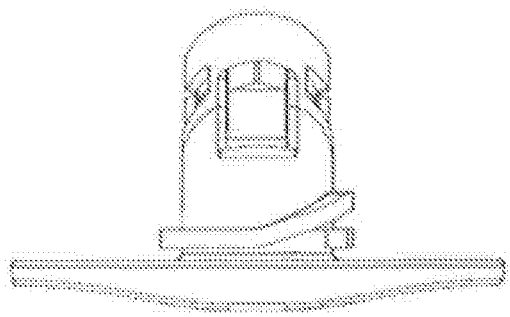
Figure 39D:
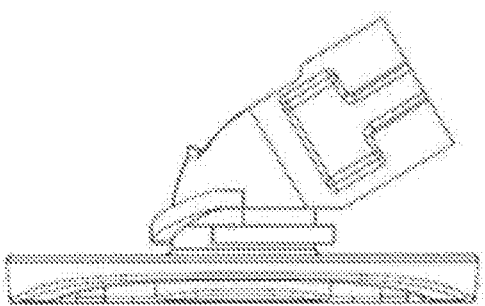
Figure 40A:
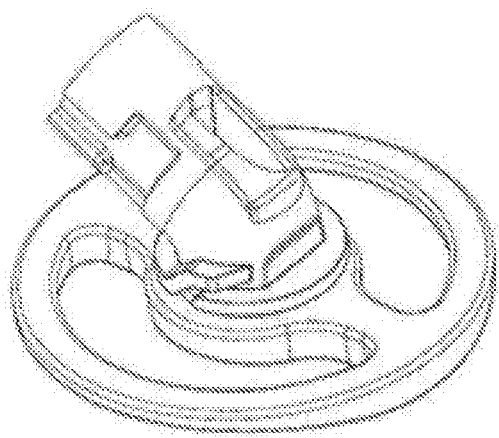
Figure 40B:
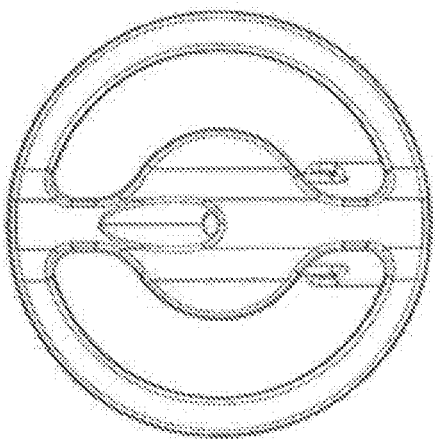
Figure 40C:
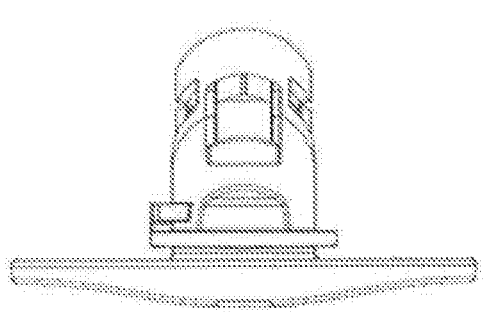
Figure 40D:
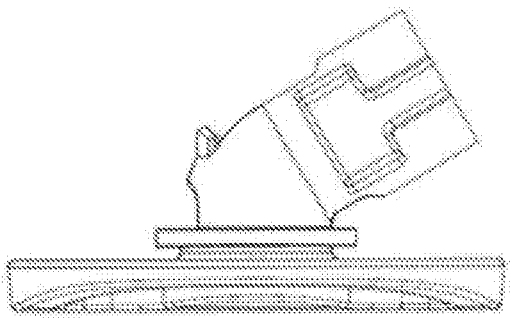
Figure 41A:
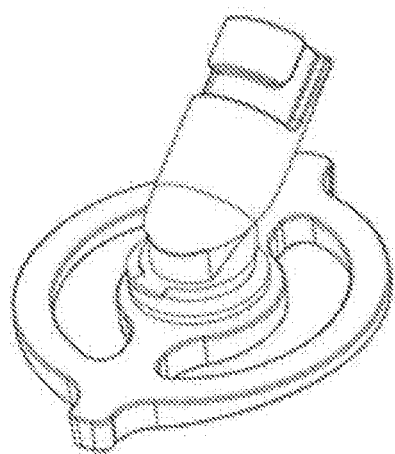
Figure 41B:
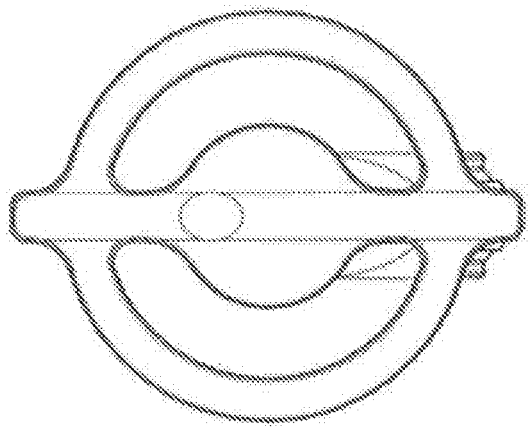
Figure 41C:
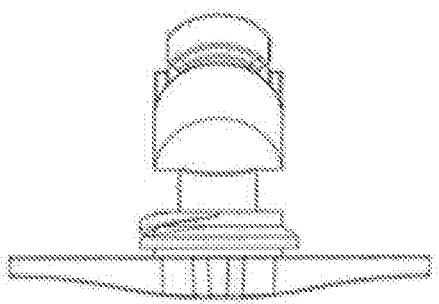
Figure 41D:
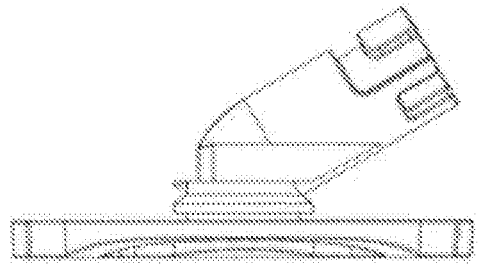
Figure 42A:
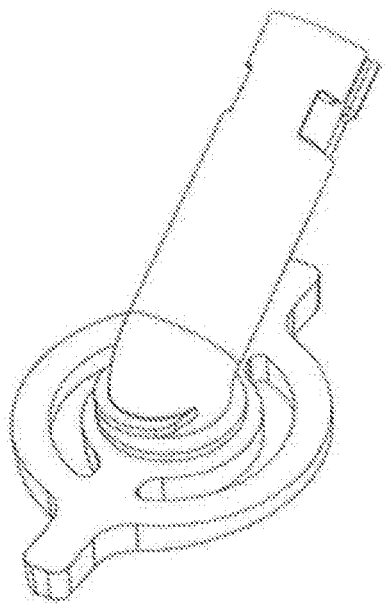
Figure 42B:
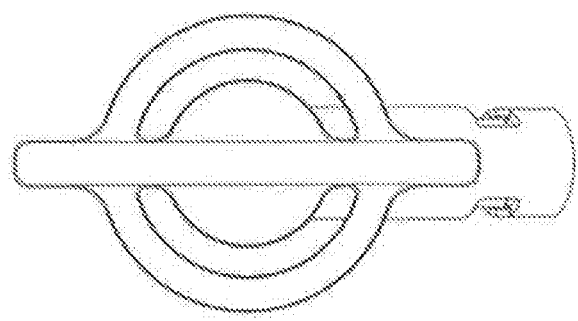
Figure 42C:
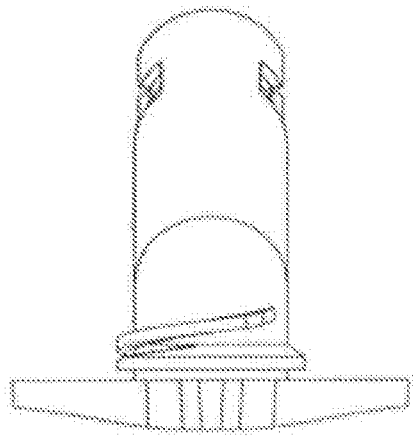
Figure 42D:
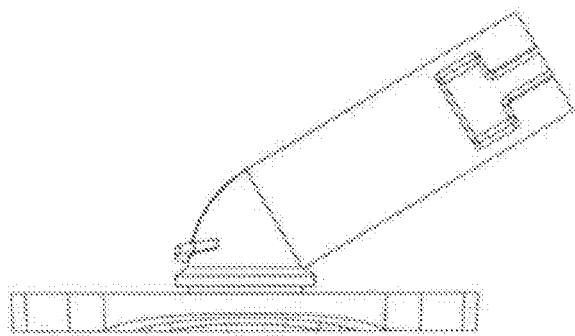
Figure 43A:
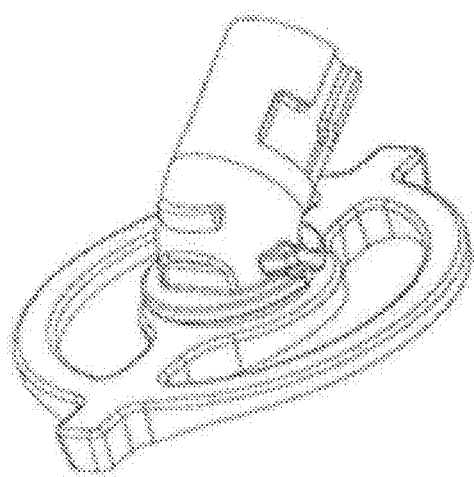
Figure 43B:
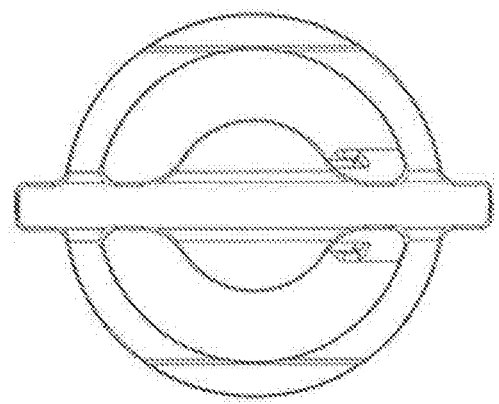
Figure 43C:
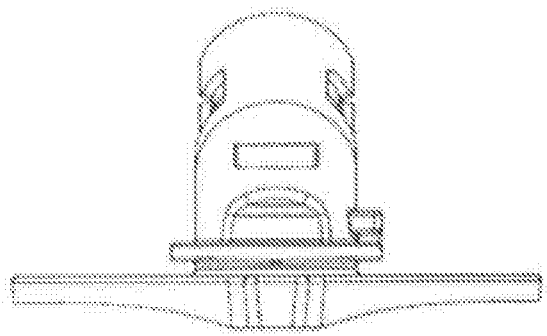
Figure 43D:
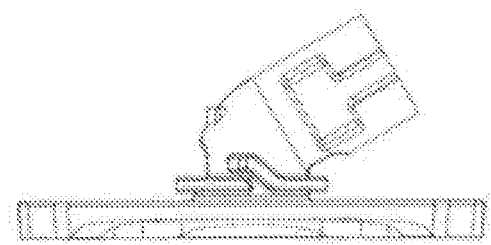
Figure 44A:
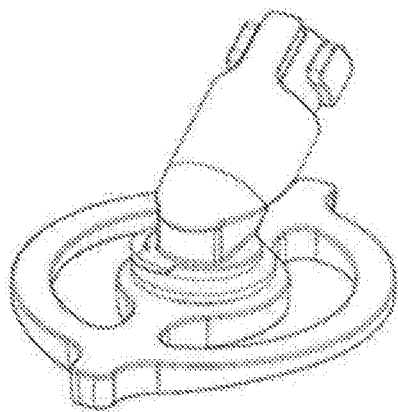
Figure 44B:
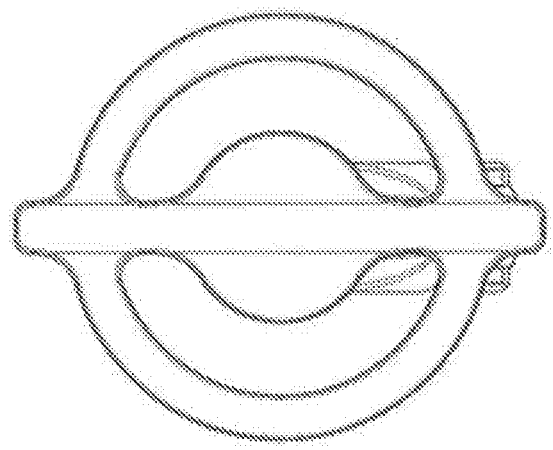
Figure 44C:
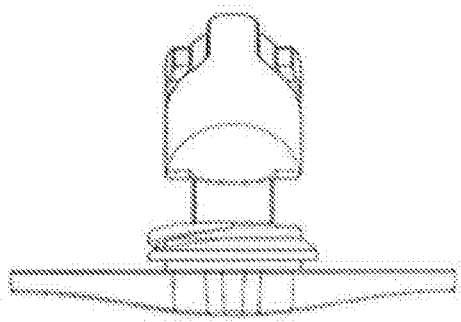
Figure 44D:
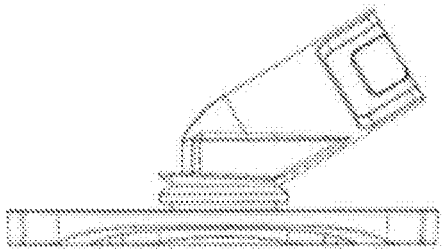
Figure 45A:
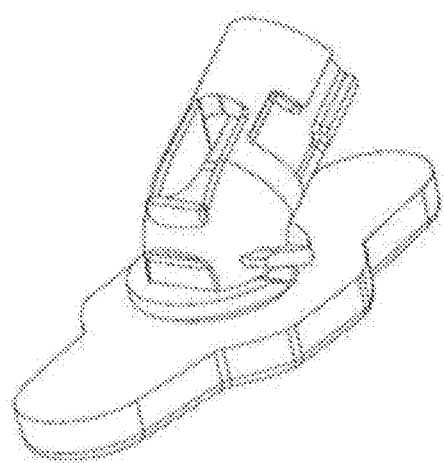
Figure 45B:
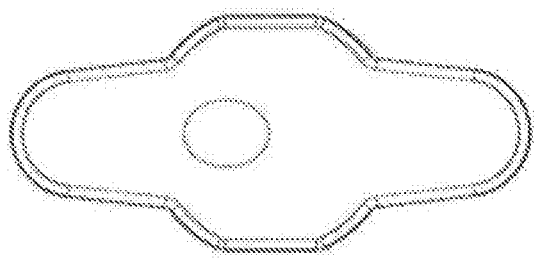
Figure 45C:
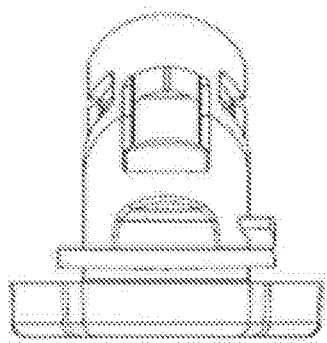
Figure 45D:
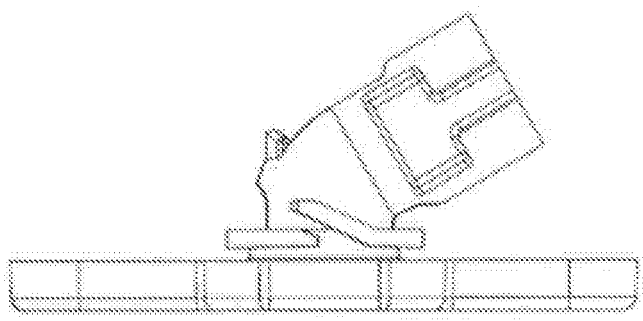
Figure 46A:
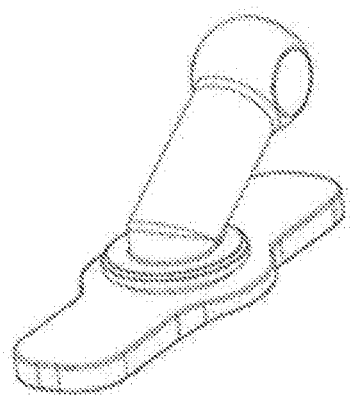
Figure 46B:
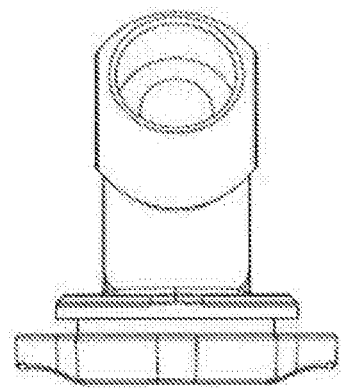
Figure 46C:
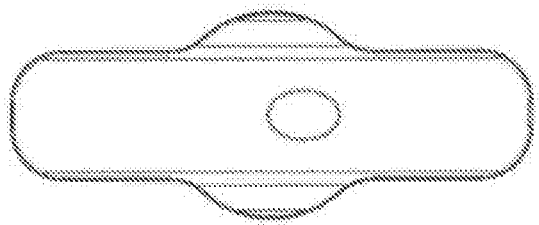
Figure 46D:
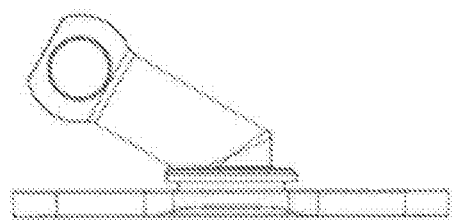
Figure 47A:
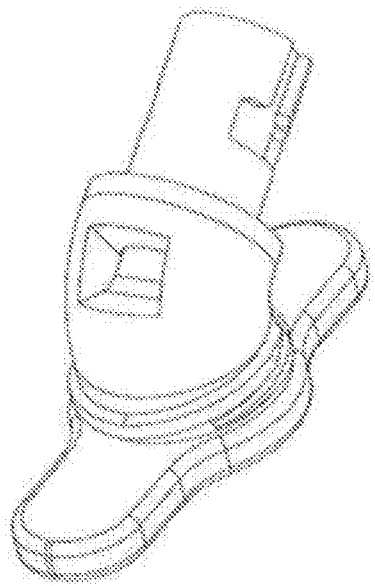
Figure 47B:
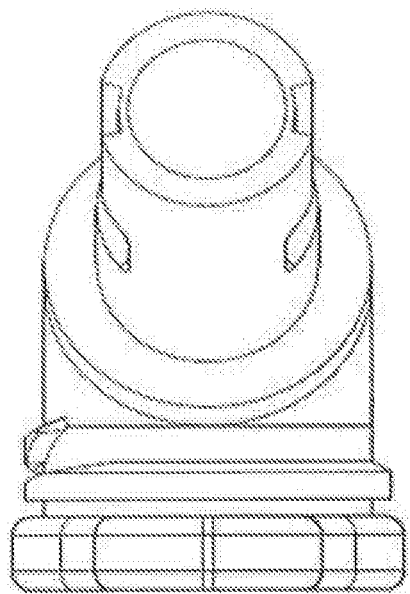
Figure 47C:
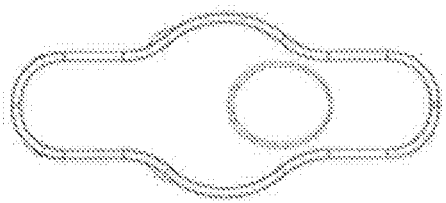
Figure 47D:
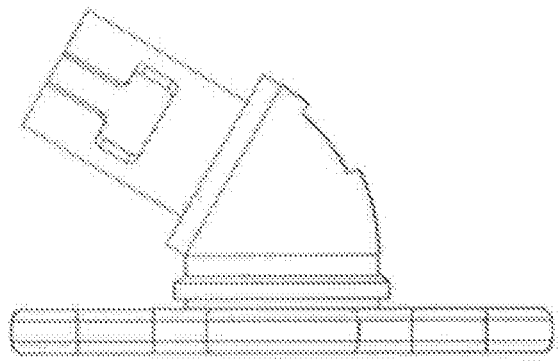
Figure 48A:
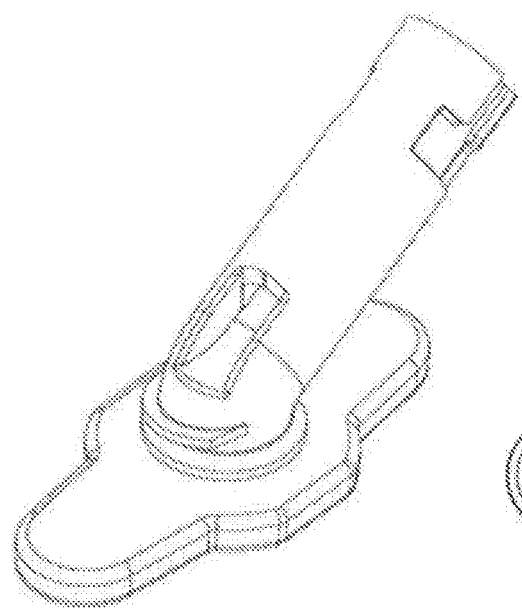
Figure 48B:
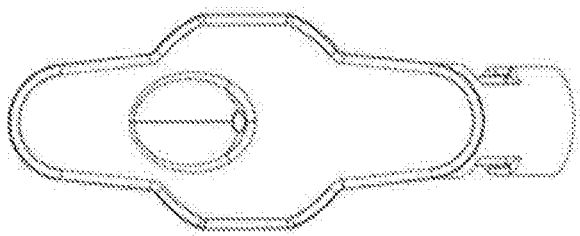
Figure 48C:
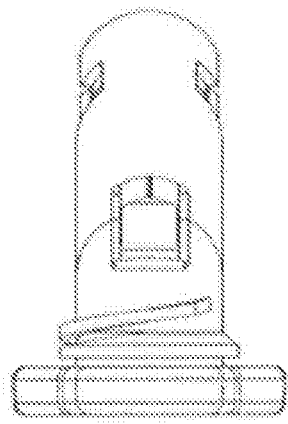
Figure 48D:
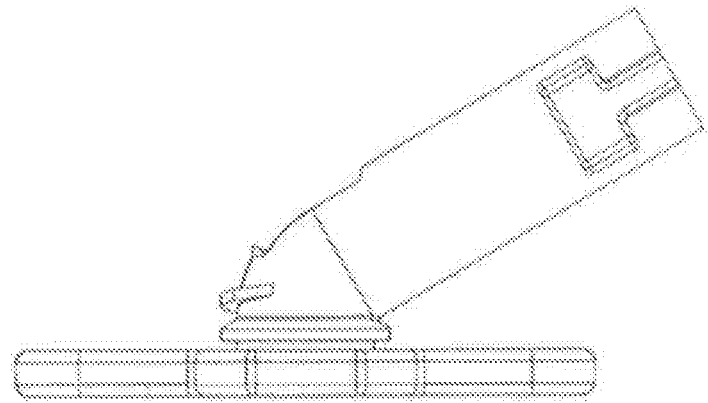
Figure 49A:
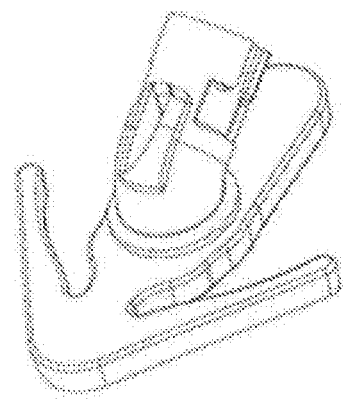
Figure 49B:
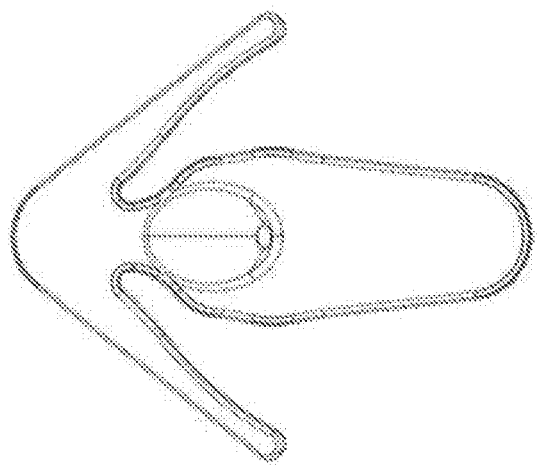
Figure 49C:
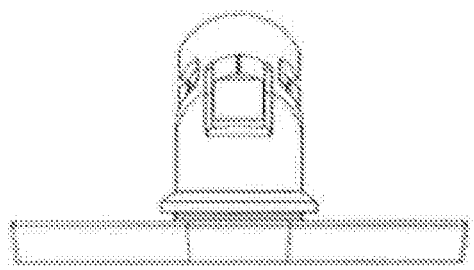
Figure 49D:
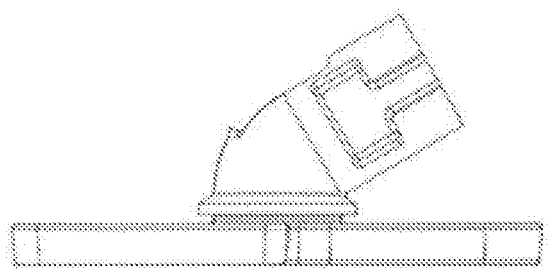
Figure 50A:
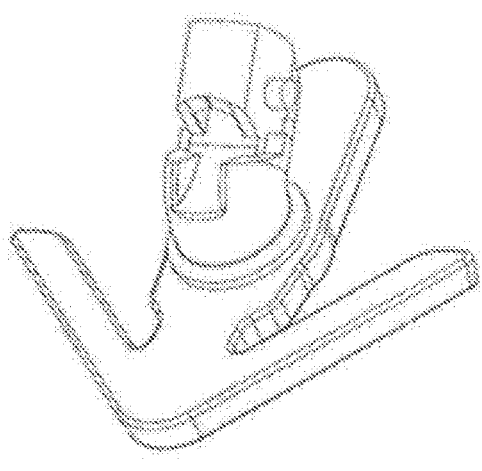
Figure 50B:
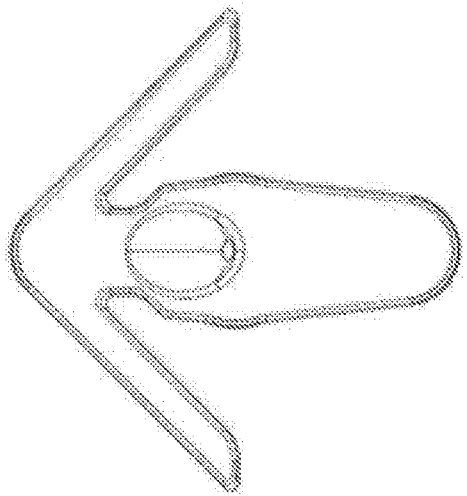
Figure 50C:
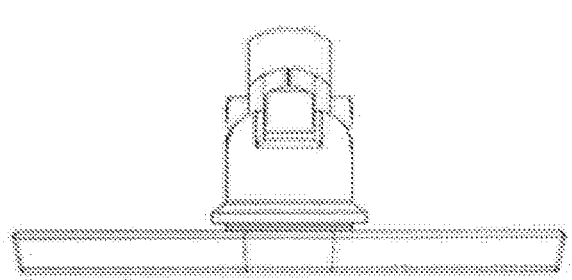
Figure 50D:
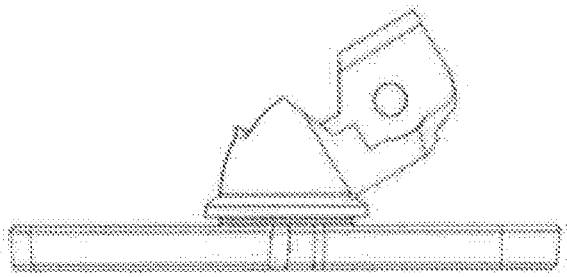
Figure 51A:
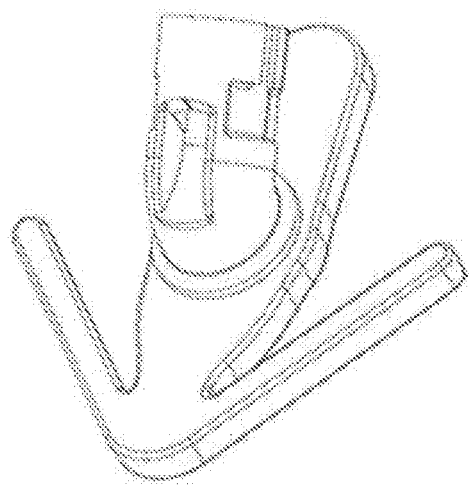
Figure 51B:
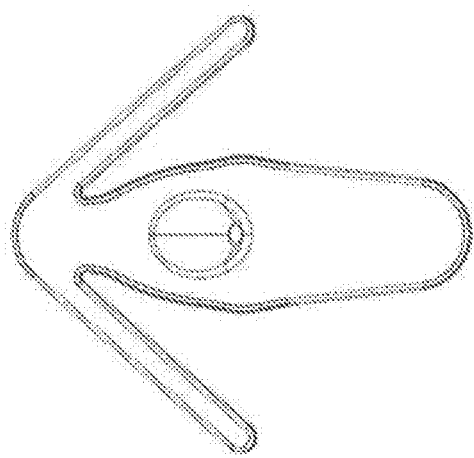
Figure 51C:
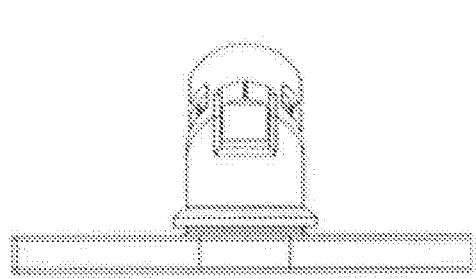
Figure 51D:
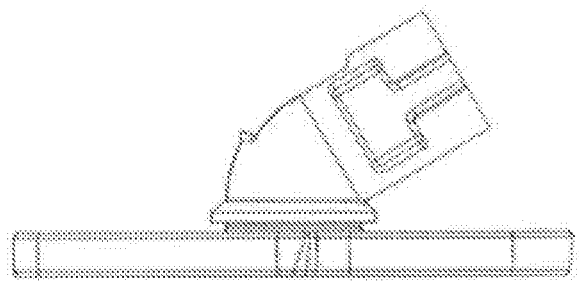
Figure 52A:
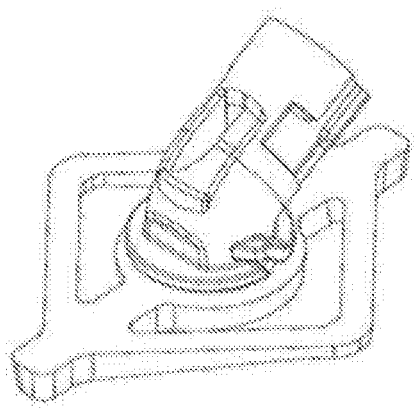
Figure 52B:
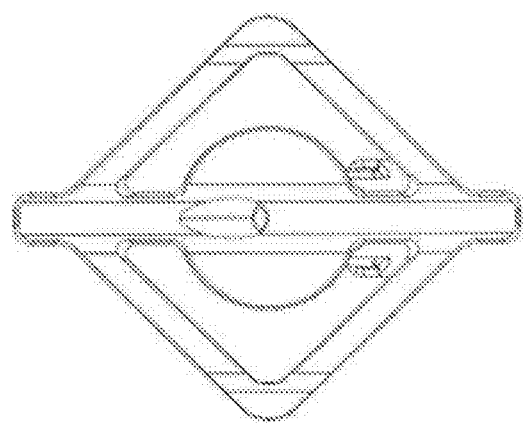
Figure 52C:
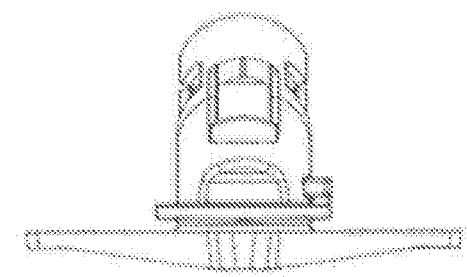
Figure 52D:
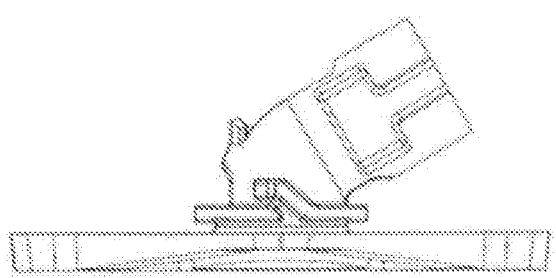
Figure 53A:
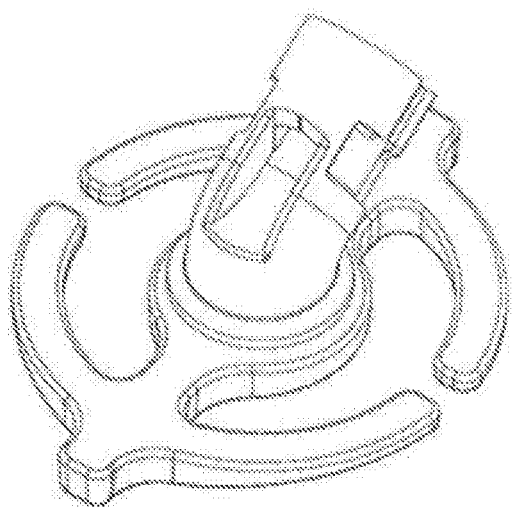
Figure 53B:
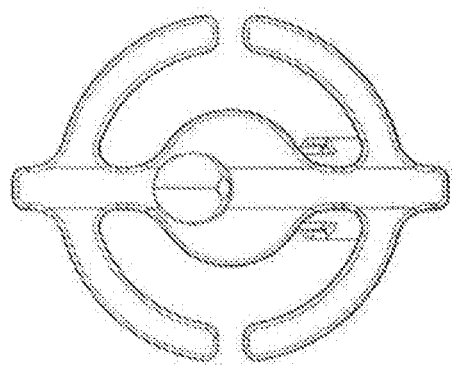
Figure 53C:
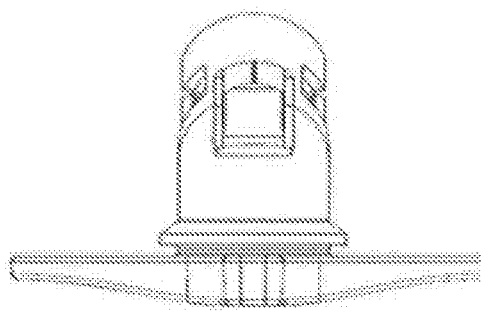
Figure 53D:
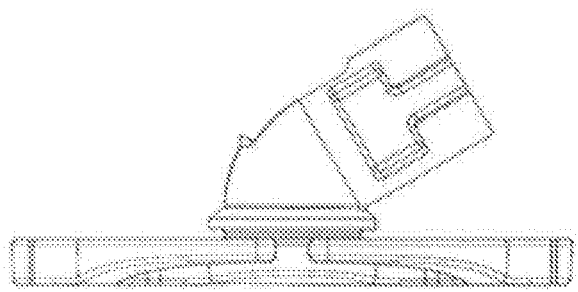
Figure 54A:
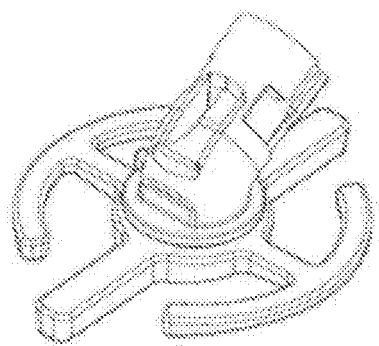
Figure 54B:
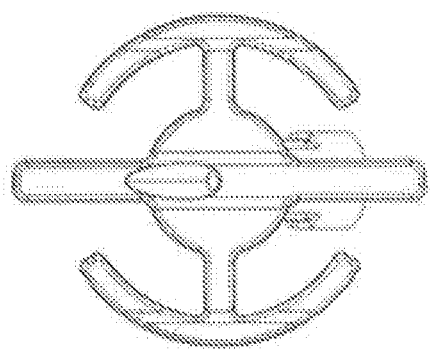
Figure 54C:
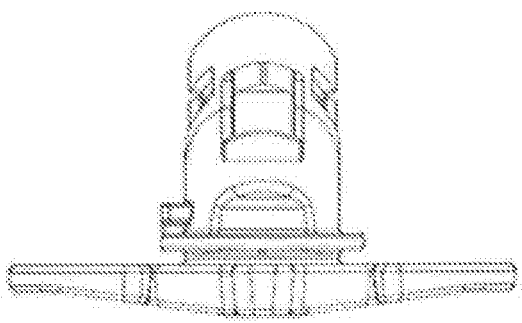
Figure 54D:
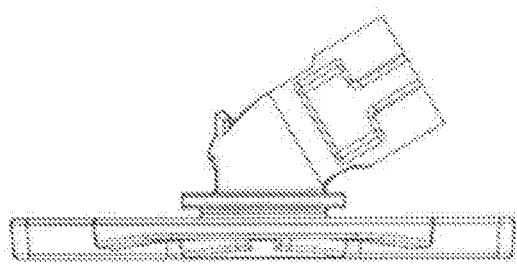
Figure 55A:
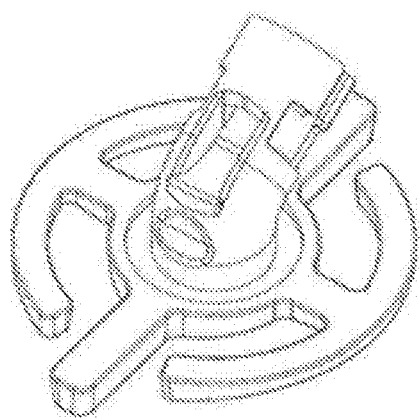
Figure 55B:
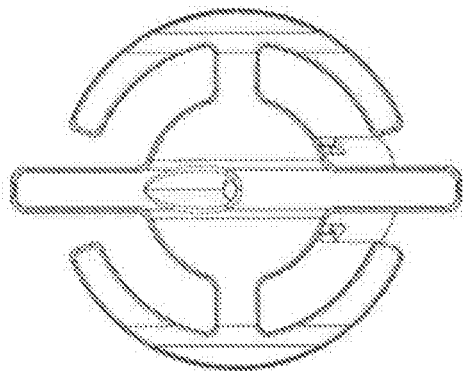
Figure 55C:
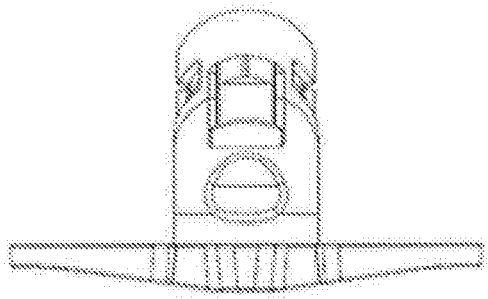
Figure 55D:
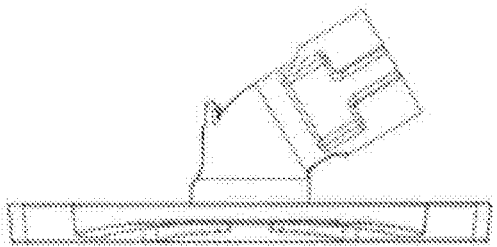
Figure 56A:
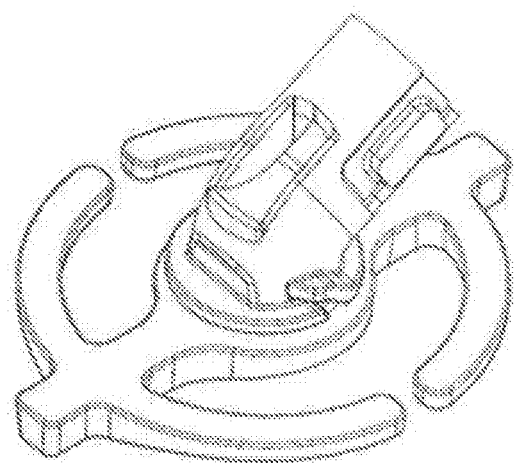
Figure 56B:
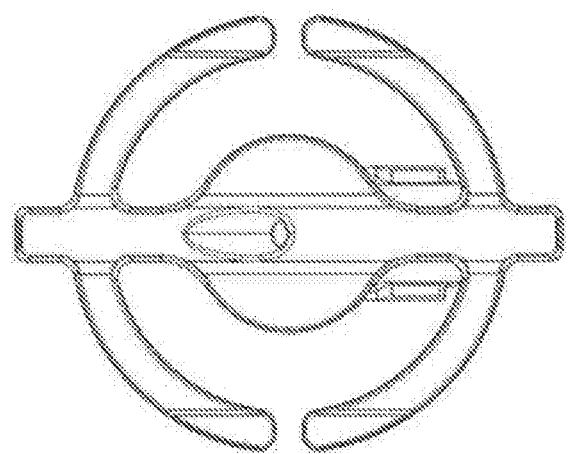
Figure 56C:
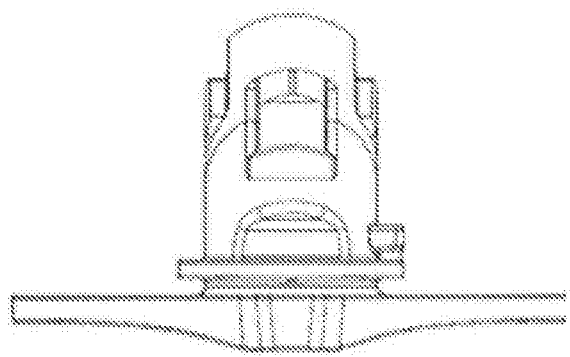
Figure 56D:
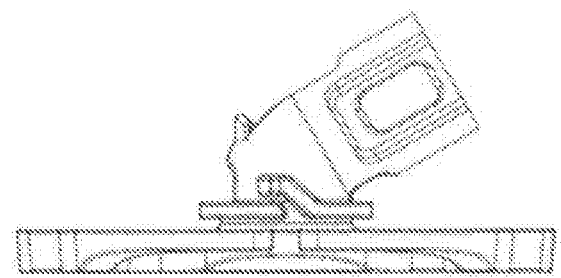
Figure 57A:
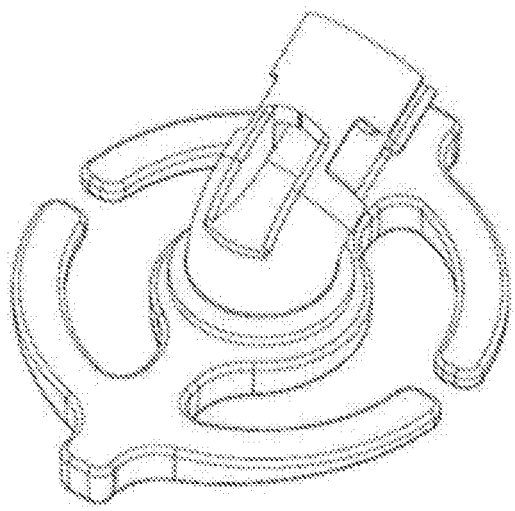
Figure 57B:
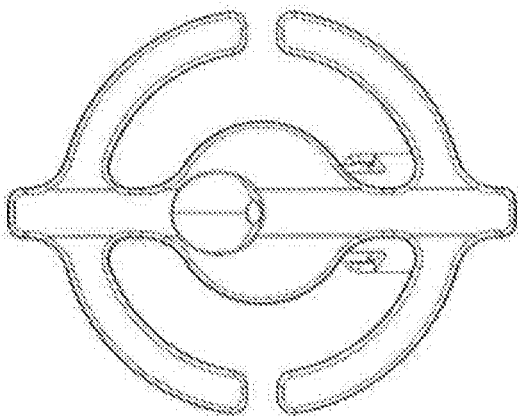
Figure 57C:
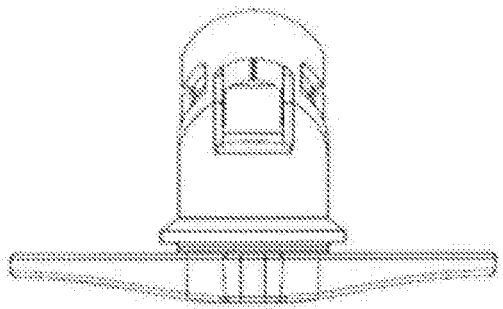
Figure 57D:
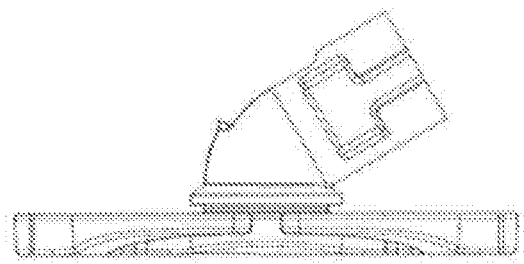
Figure 58A:
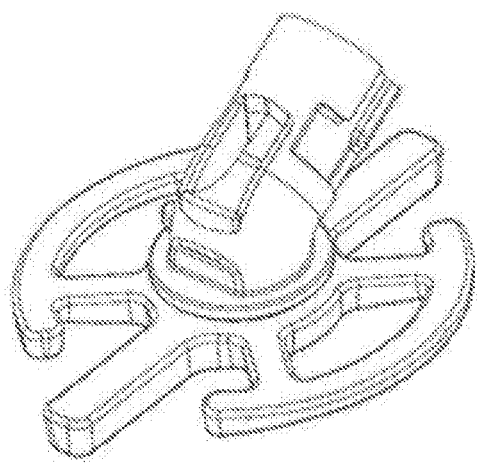
Figure 58B:
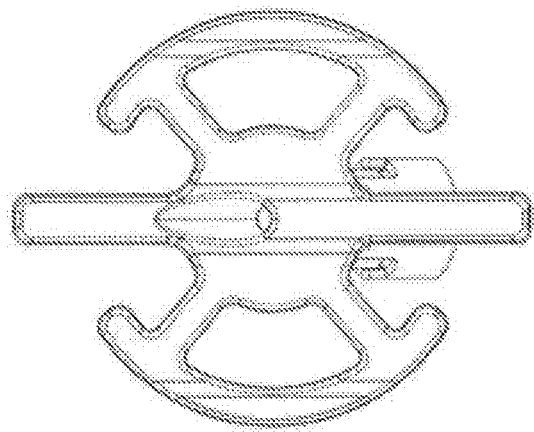
Figure 58C:
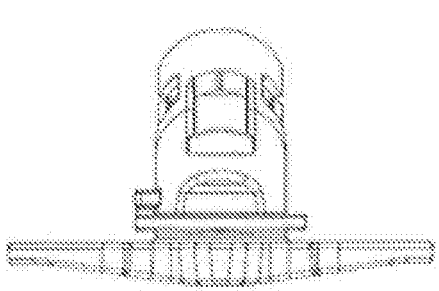
Figure 58D:
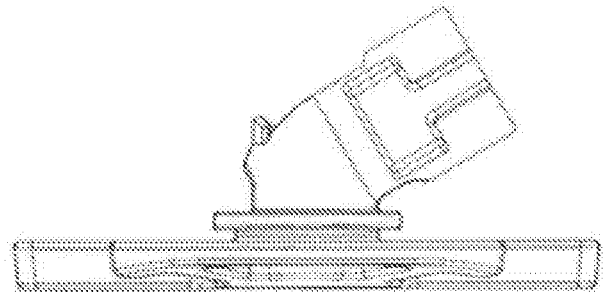
Figure 59A:
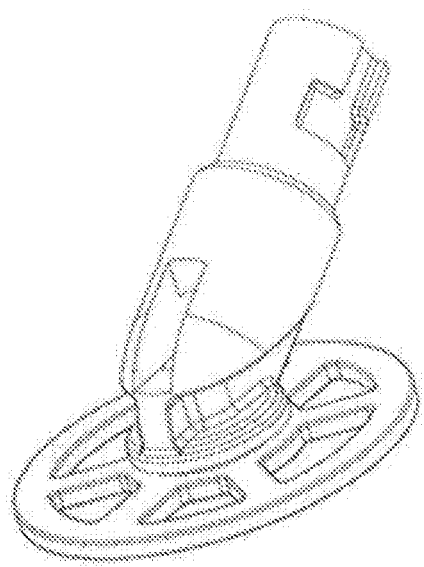
Figure 59B:
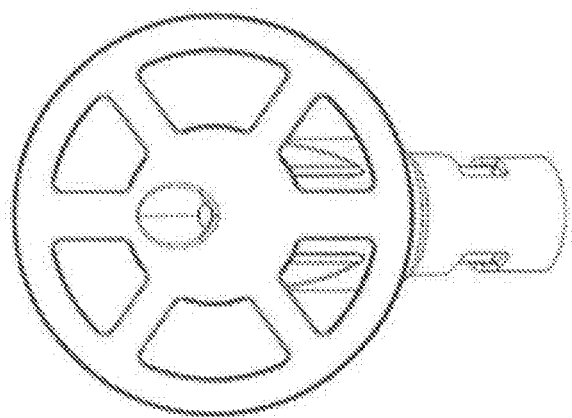
Figure 59C:
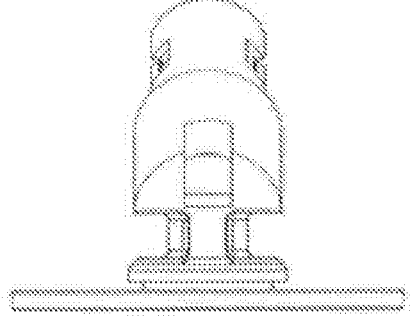
Figure 59D:
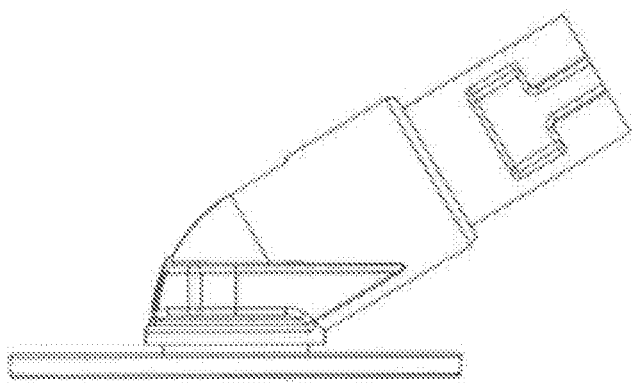
Figure 60A:
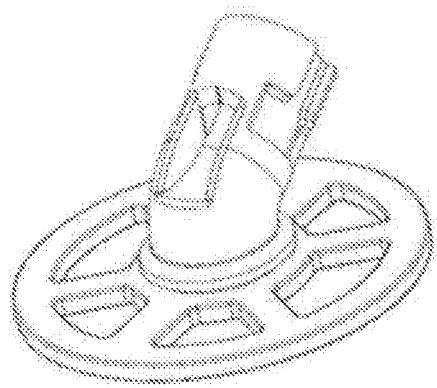
Figure 60B:
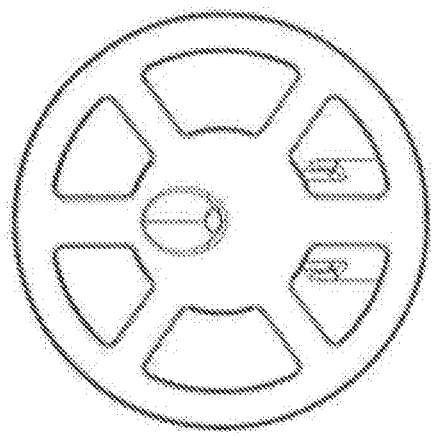
Figure 60C:
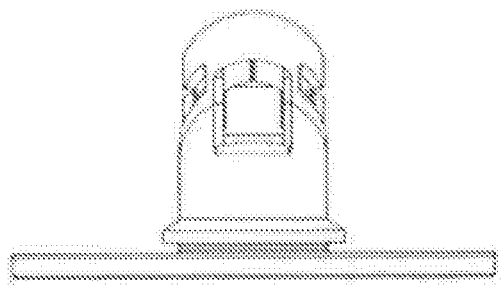
Figure 60D:
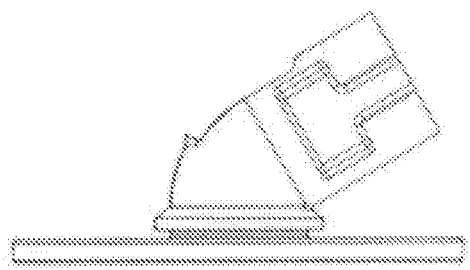
Figure 61A:
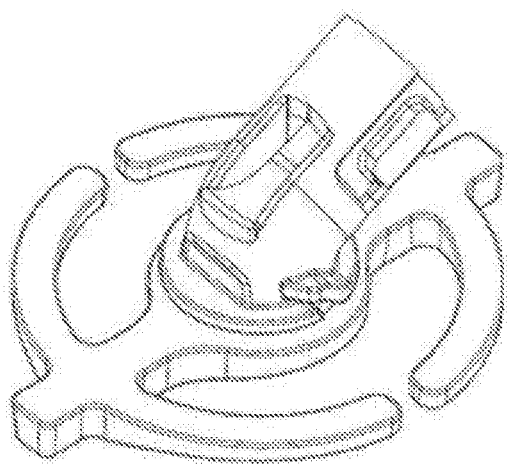
Figure 61B:
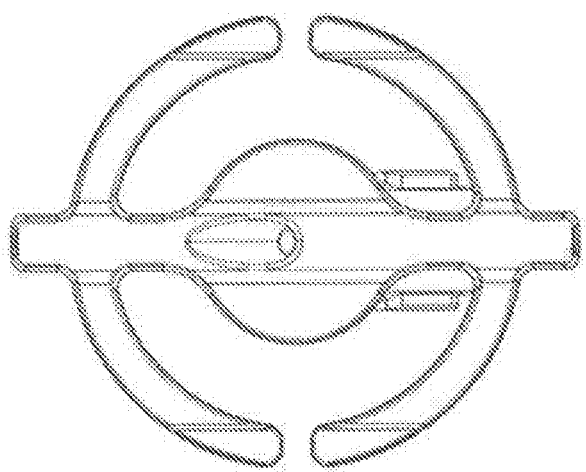
Figure 61C:
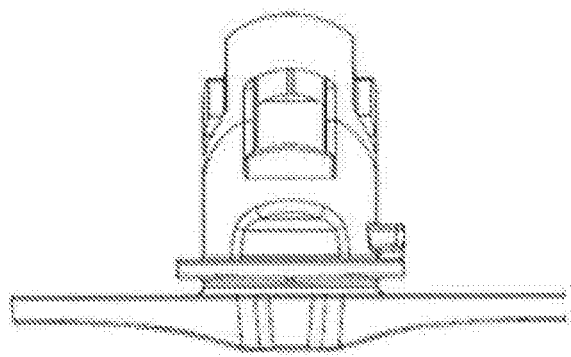
Figure 61D:
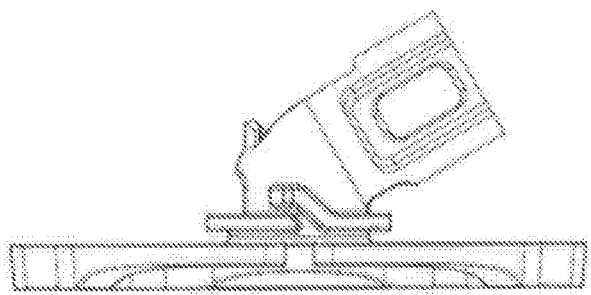
Figure 62A:
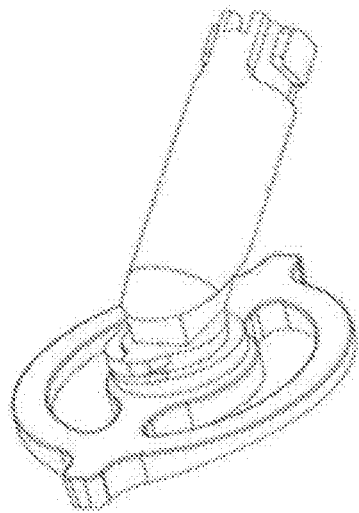
Figure 62B:
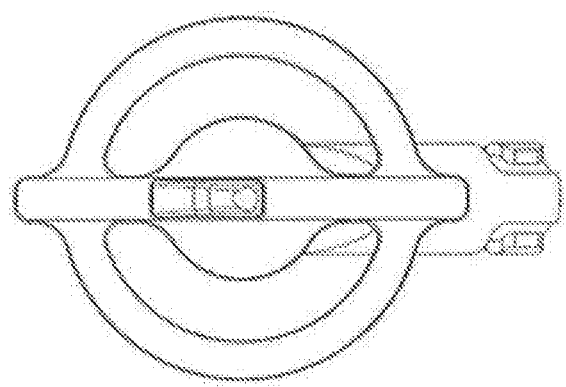
Figure 62C:
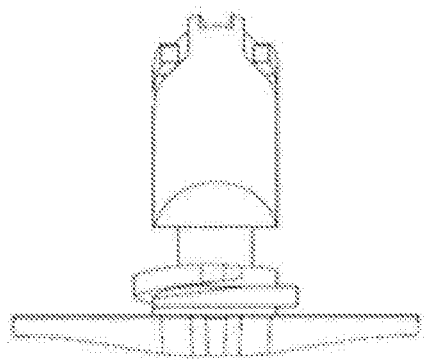
Figure 62D:
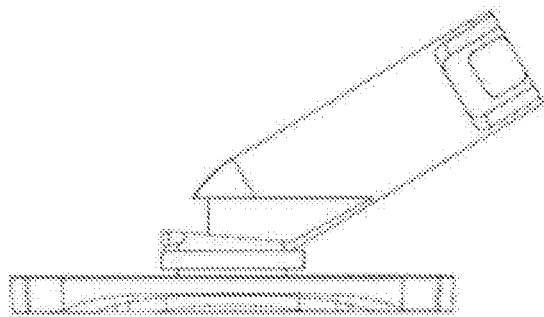
Figure 63A:
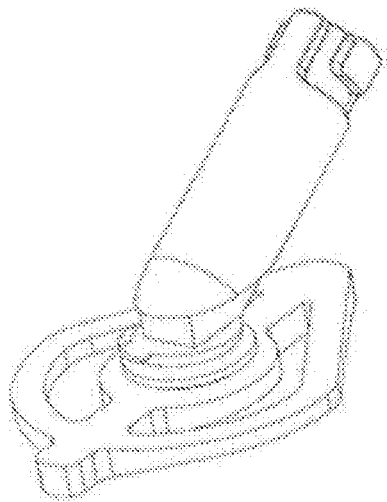
Figure 63B:
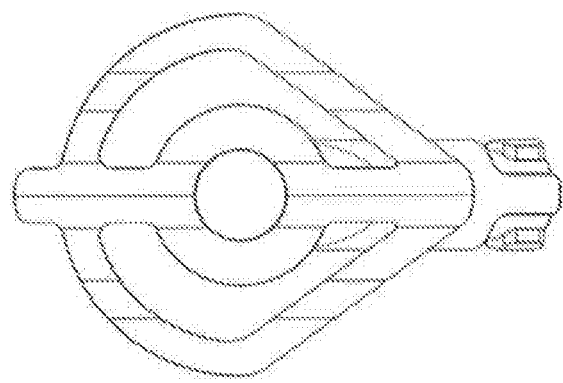
Figure 63C:
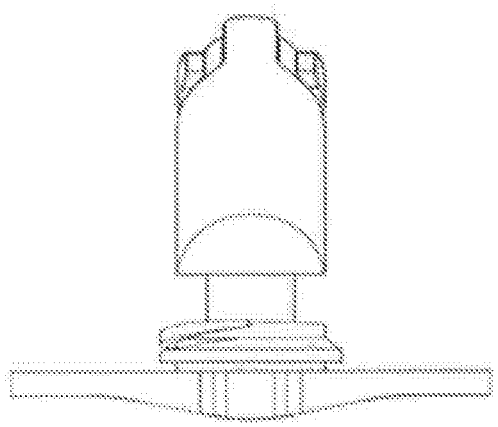
Figure 63D:
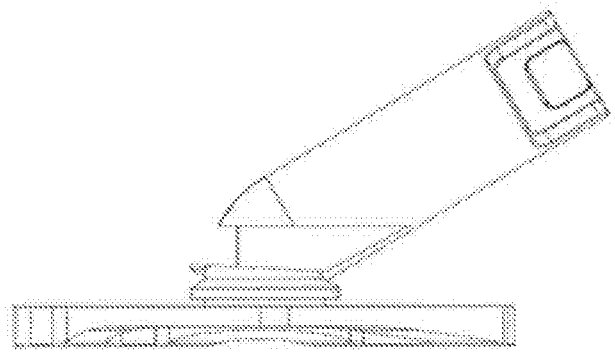
Figure 64A:
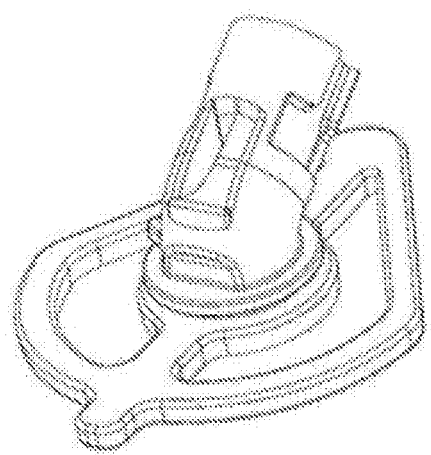
Figure 64B:
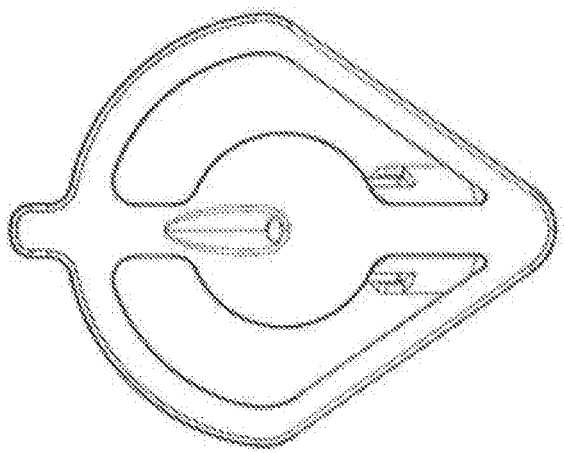
Figure 64C:
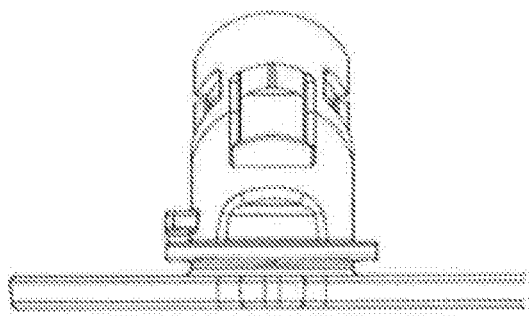
Figure 64D:
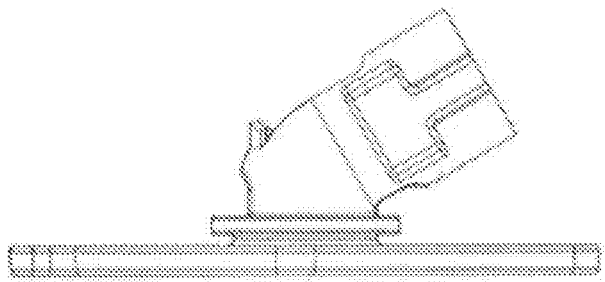
Figure 65A:
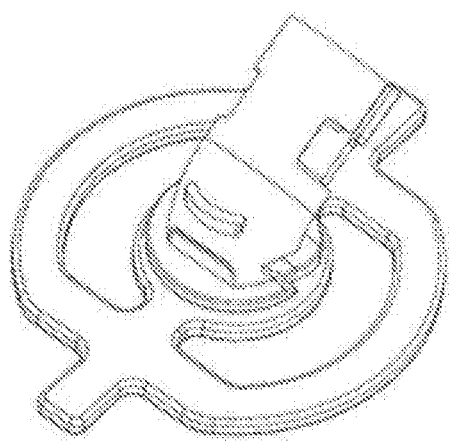
Figure 65B:
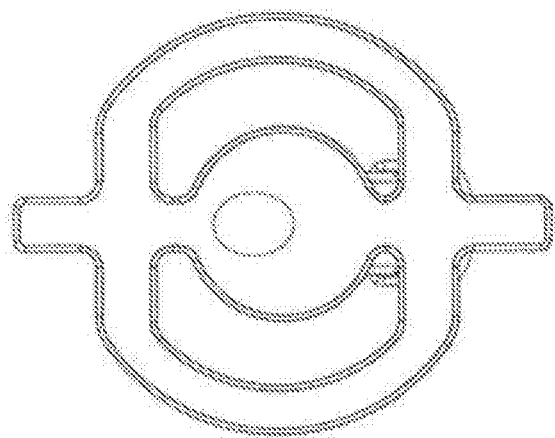
Figure 65C:
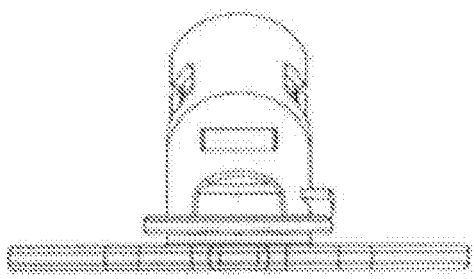
Figure 65D:
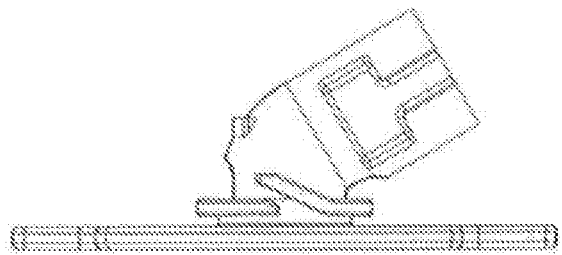
Figure 66A:
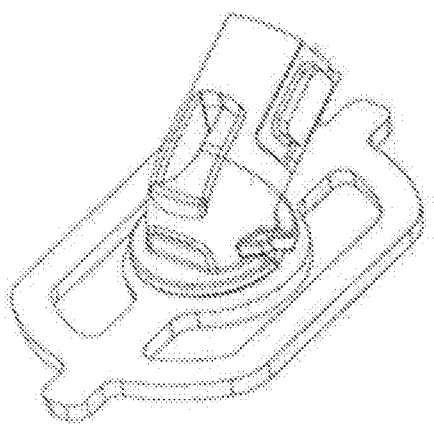
Figure 66B:
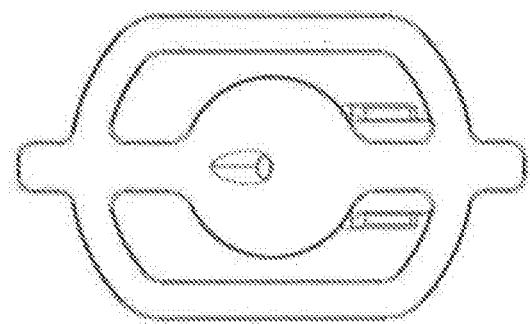
Figure 66C:
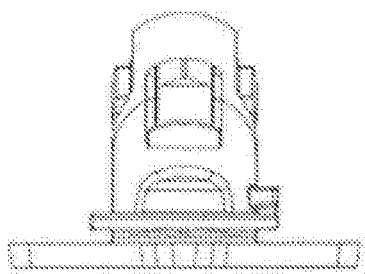
Figure 66D:
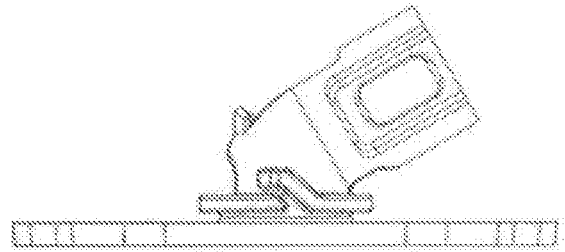
Figure 67A:
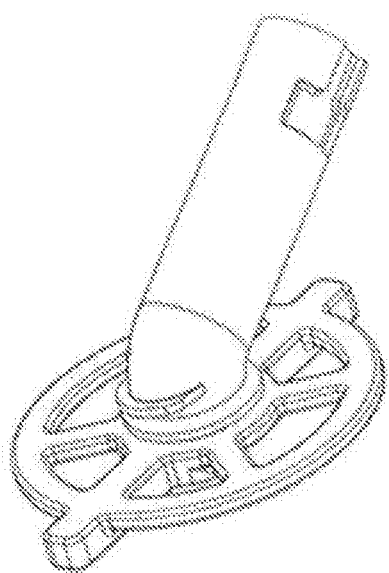
Figure 67B:
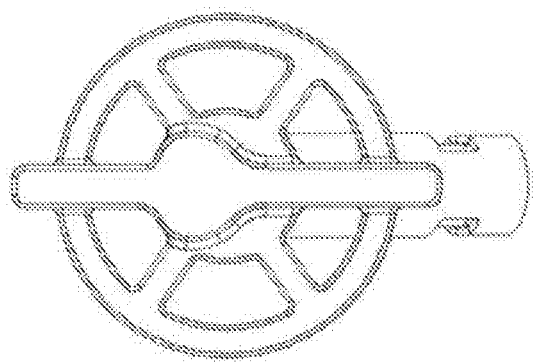
Figure 67C:
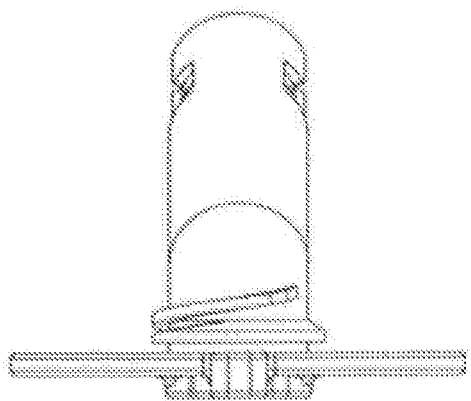
Figure 67D:
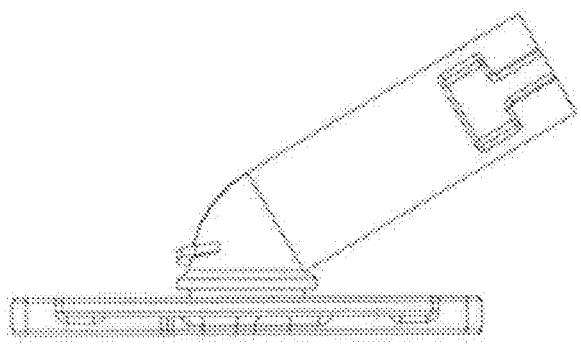
Figure 69A:
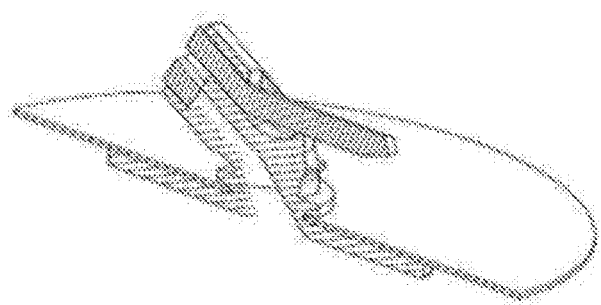
Figure 69B:
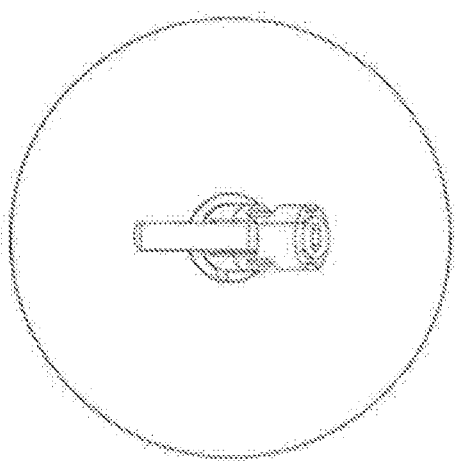
Figure 69C:
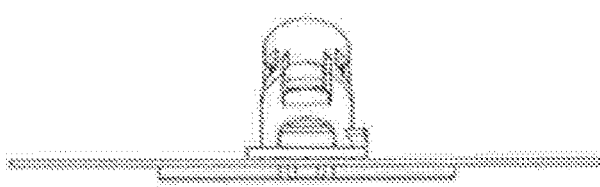
Figure 69D:
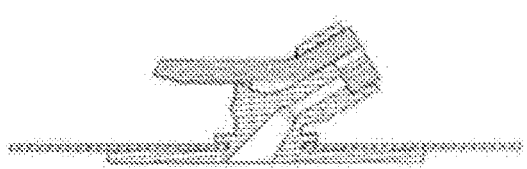
Figure 70A:
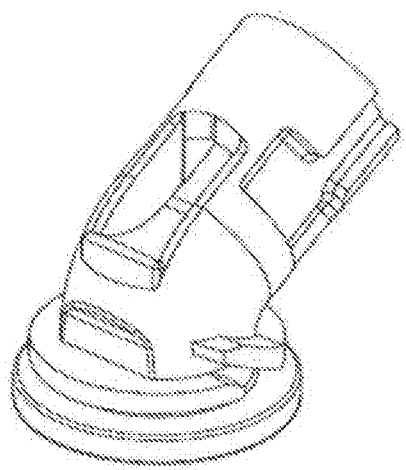
Figure 70B:
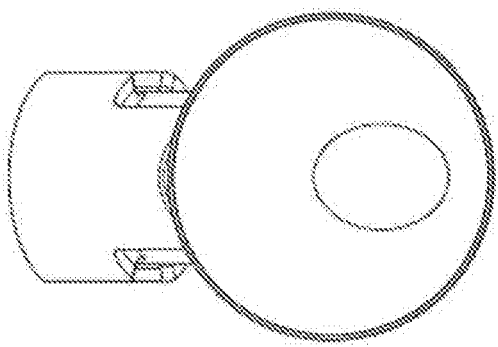
Figure 70C:
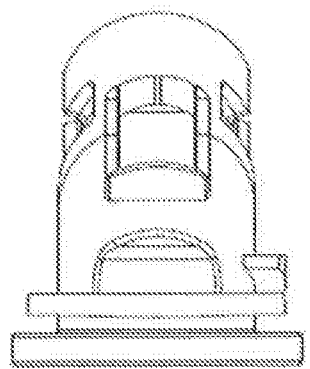
Figure 70D:
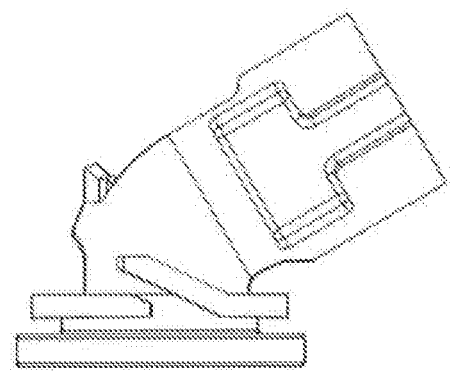
Figure 71A:
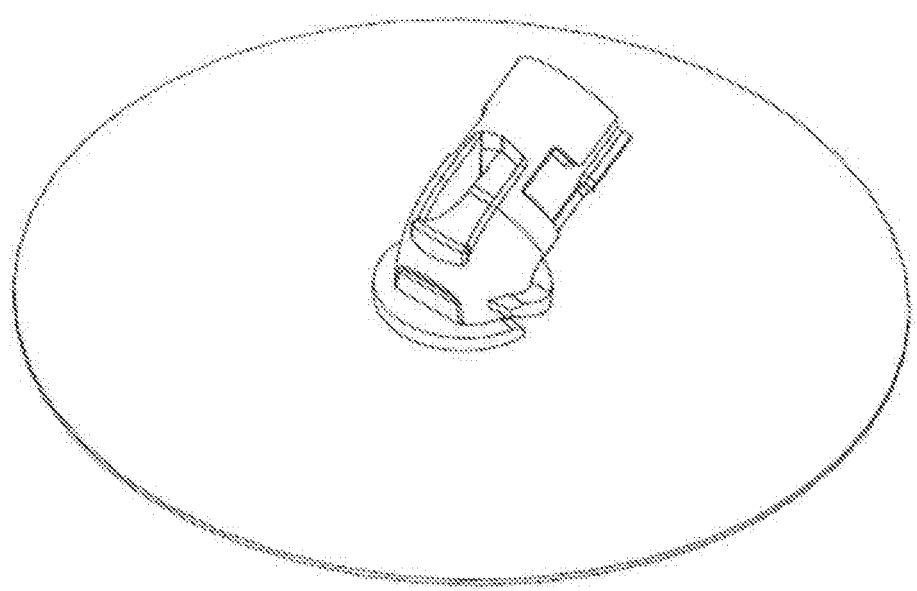
Figure 71B:
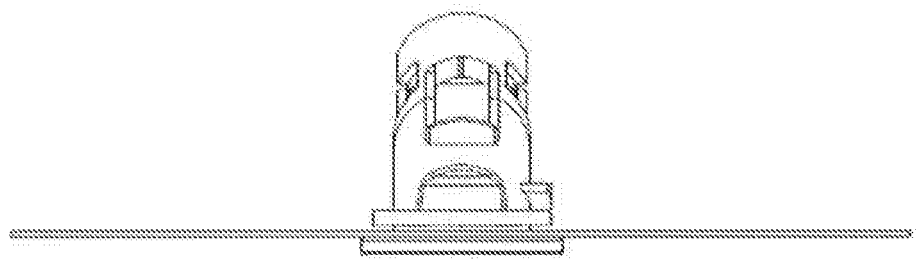
Figure 71C:
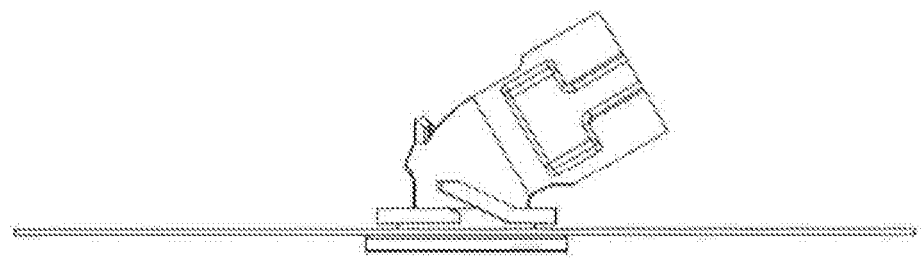
Figure 72A:
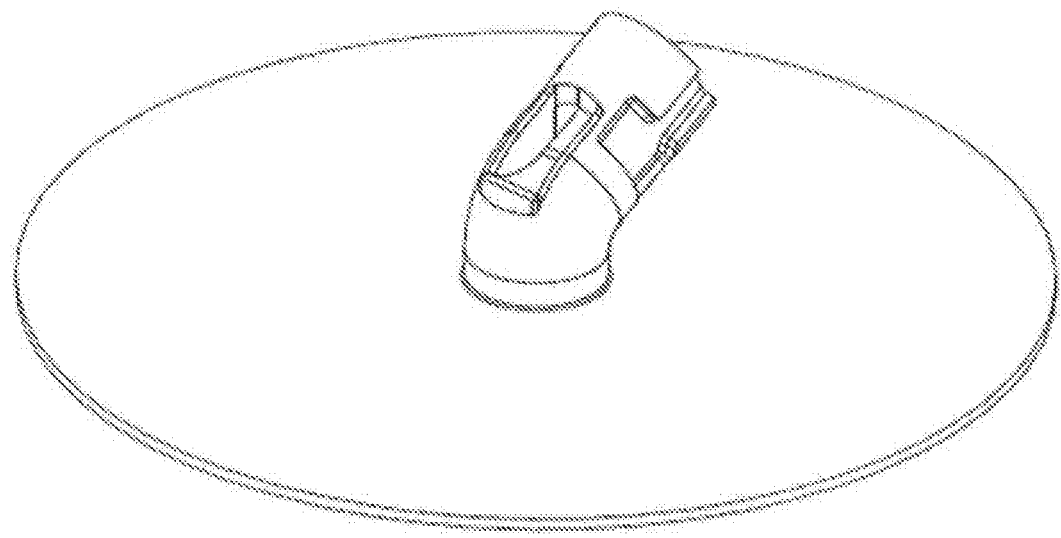
Figure 72B:
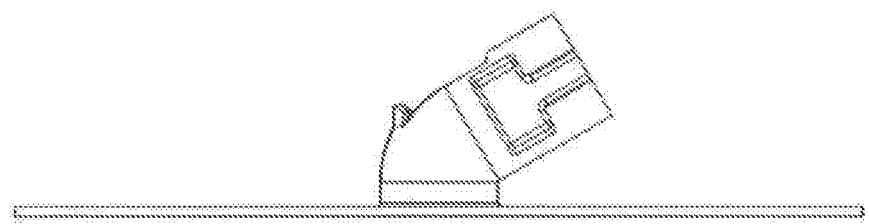
Figure 72C:
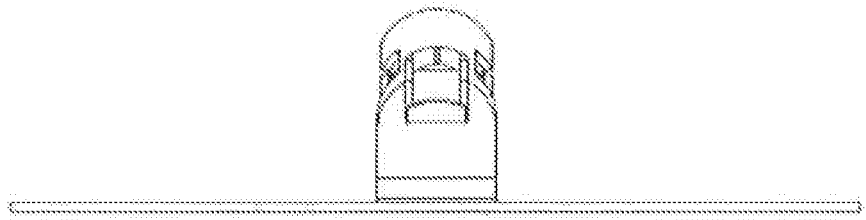

FIG. 21C shows the sealable member 106 and the support member 118 in their folded state. The folded implant is prepared for direct insertion into a body lumen, e.g., an artery. The loading funnel 2104 is then detached from the delivery cannula 2202. FIG. 22 is a diagram of the sealing member and support member in the delivery configuration in the delivery cannula 2202. Further examples of the loading funnel and delivery cannula is described in U.S. Patent Application Publication No. US 2014/0345109, filed Mar. 13, 2014, titled "Loading Devices and Methods for Percutaneous Perforation Closure Systems," the content of which is incorporated by reference herein in its entirety.

Figure 17A:
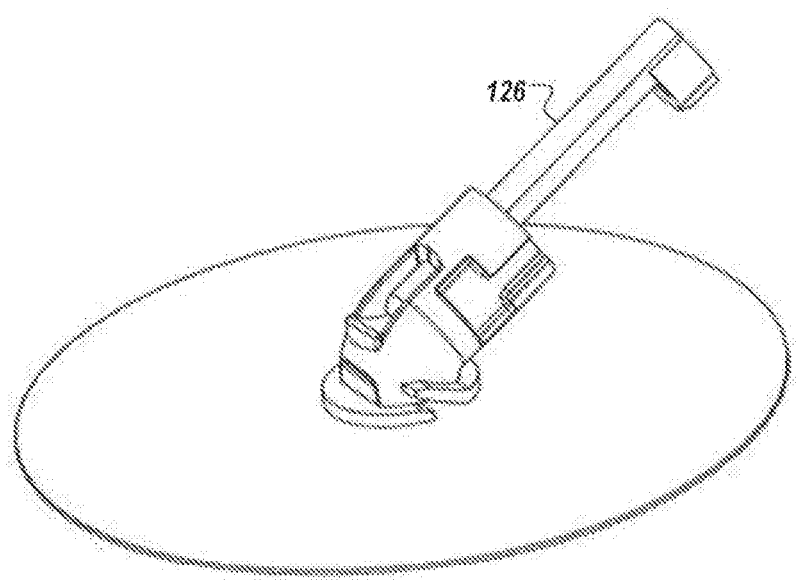
FIGS. 17A, 18A and 18B are diagrams showing a perspective view and a cross-sectional view of an assembled closure device.
Figure 17B:
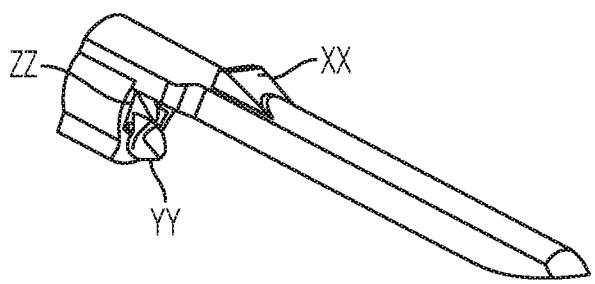
FIG. 17B is diagram showing a perspective view of a locking feature.
Figure 18A:
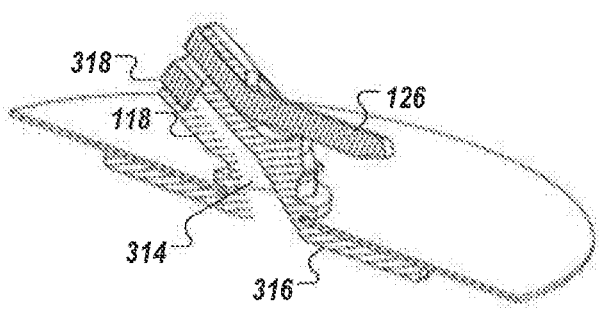
Figure 18B:
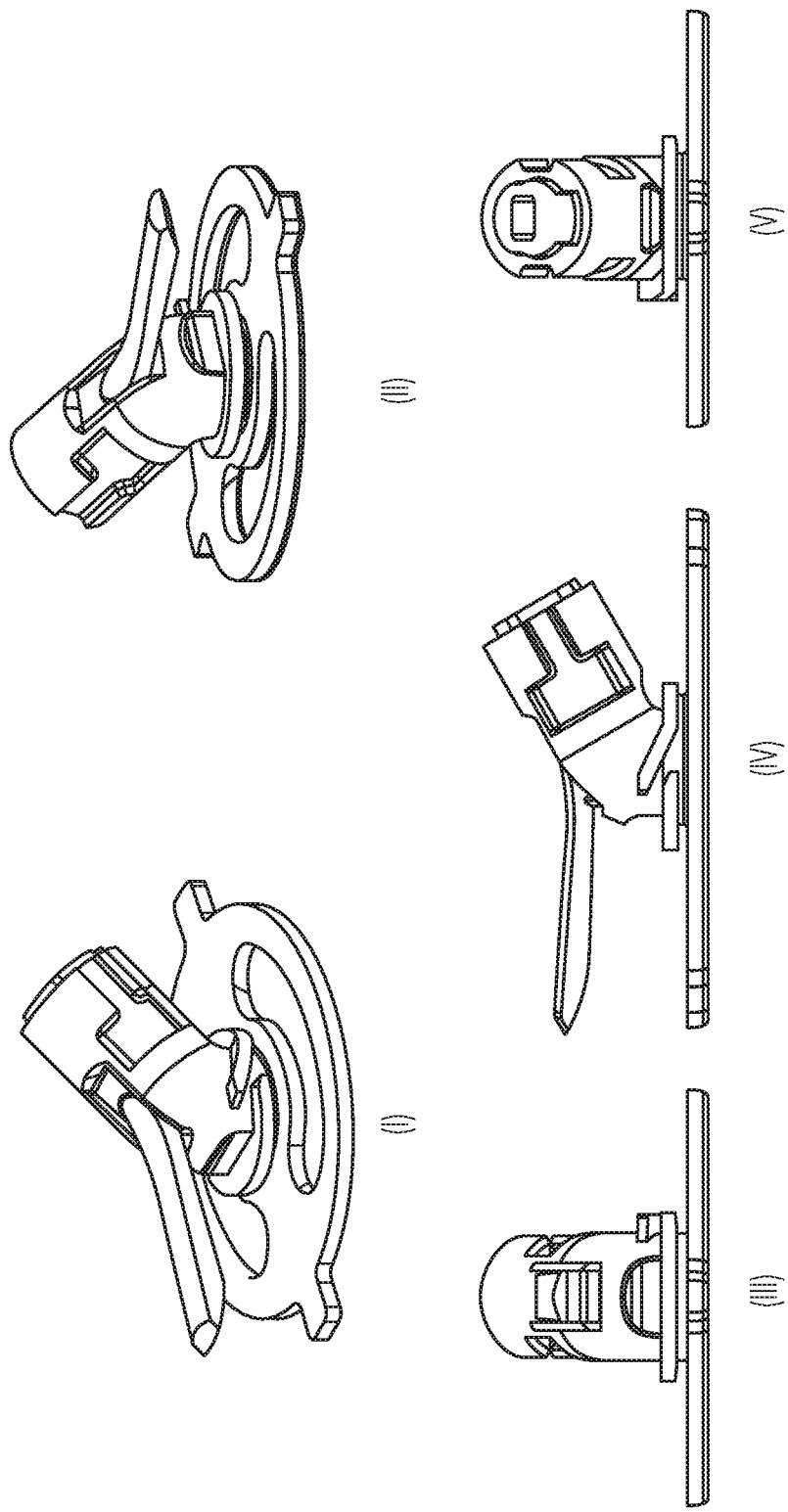

Referring back to FIG. 3B, the support member 118 has a channel 314 for guiding the guide wire 202 (see FIG. 2). In some embodiments, the channel 314 runs through the support member 118 between a bottom surface 316 of the base 120 and a top surface 318 of the column 122 (see FIG. 18A). Referring to FIGS. 17A, 17B, 18A and 18B, in certain embodiments, the channel 314 runs from the bottom of the center of the support member 118 to the top of the column 122 for guide wire access. FIG. 17A shows the closure device 100 and the guard member 126, prior to the deployment of the guard member 126. FIG. 17B shows an embodiment of guard member containing a locking feature (xx) to lock the guard member into position. A wedge feature (yy) which closes guide wire access channel 314 reduces blood loss through this avenue. The guard member contains a guide wire lumen (22) which can accommodate up to a 0.018" guide wire. FIG. 18A is a cross-sectional perspective view of diagram of the guard member 126 in the deployed state. FIG. 18B is view of a diagram of the guard member (FIG. 17B) in the deployed state in support member (FIG. 4C)

Threaded Portion on the Support Member

Figure 19A:
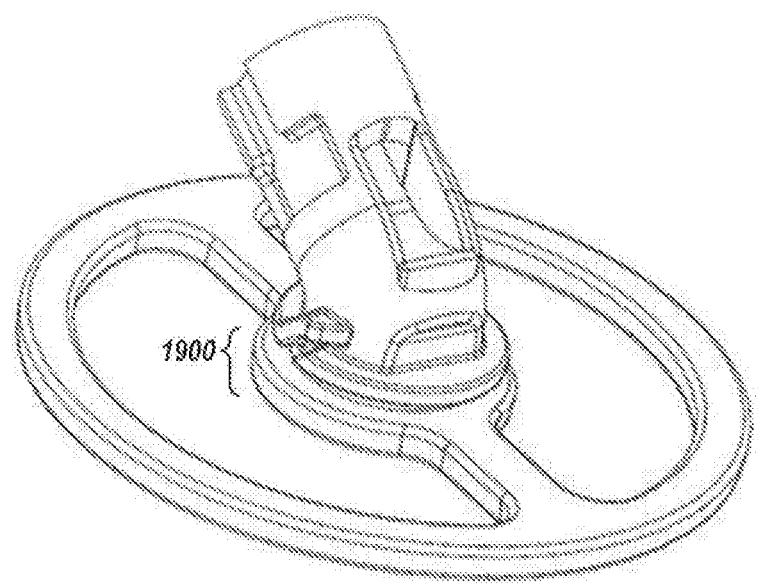
FIGS. 19A, 19B, and 19C are diagrams of a perspective view, a side view, and a front view of a closure device with a threaded portion to allow assembly of the sealable member to the support member without distortion and/or deformation of the sealable member.
Figure 19B:
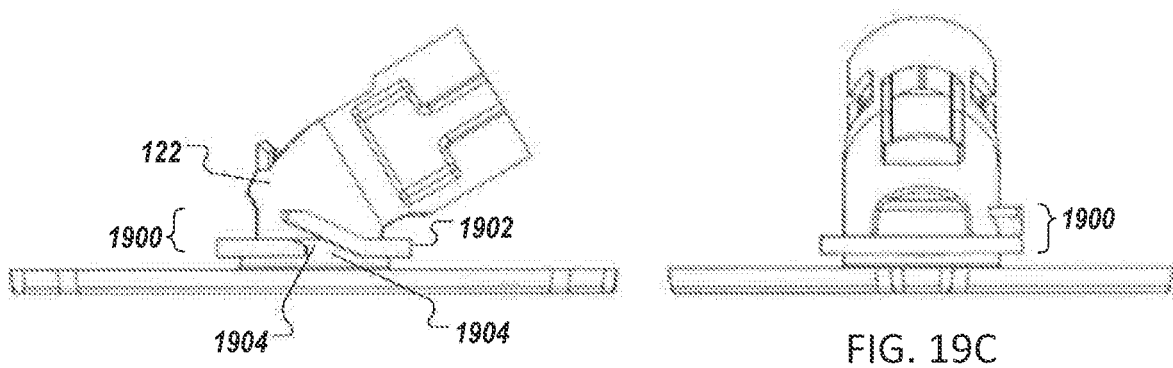
Figure 19C:
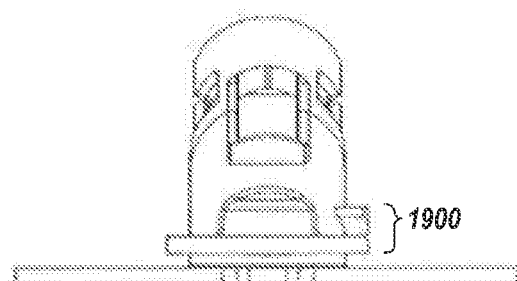

FIGS. 19A, 19B, and 19C are diagrams of a perspective view, a side view, and a front view of a closure device with a threaded portion 1900 to allow assembly of the sealable member 106 to the support member 118 without distortion or deformation of the sealable member 106. The threaded portion 1900 provides a region for the sealable member 106 to load onto the support member 118. Without having to distort and/or deform the sealable member 106 during assembly of the sealable member 106 onto the support member 118, the risk of damage to the sealable member 106 during manufacturing is reduced. The threaded portion may include a protrusion 1902 that encircles the body 1904 of the column 122. The protrusion 1902 includes a gap 1904. The protrusion 1902 has a greater diameter, in some embodiments, than that of the column 122.

The threaded portion may be employed with a support member having a rigid foot core. Further examples of rigid foot cores are described in U.S. Patent Application Publication No. US 2013/0274795, titled "Devices and Methods for Delivering Implants for Percutaneous Perforation Closure," the contents of which is incorporated herein in its entirety. Examples of rigid foot core with threaded portions are provided in FIGS. 23A-72C.

In some embodiments, the threaded portion is employed in conjunction with a "button" foot core design. The button foot core, in some embodiments, is round. The profile of the "button" foot core is such that the base diameter is only slightly wider than the hole in the center of the wing. The wing can, thus, be threaded onto the column of the button foot core. An example of the "button" foot core design is provided in FIGS. 70A-71C.

In some embodiments, the "button" foot core design is employed for smaller sized apertures (e.g., between 6 and 18 (F) French), e.g., for usage in smaller-sized blood vessels/lumens.

Figure 20A:
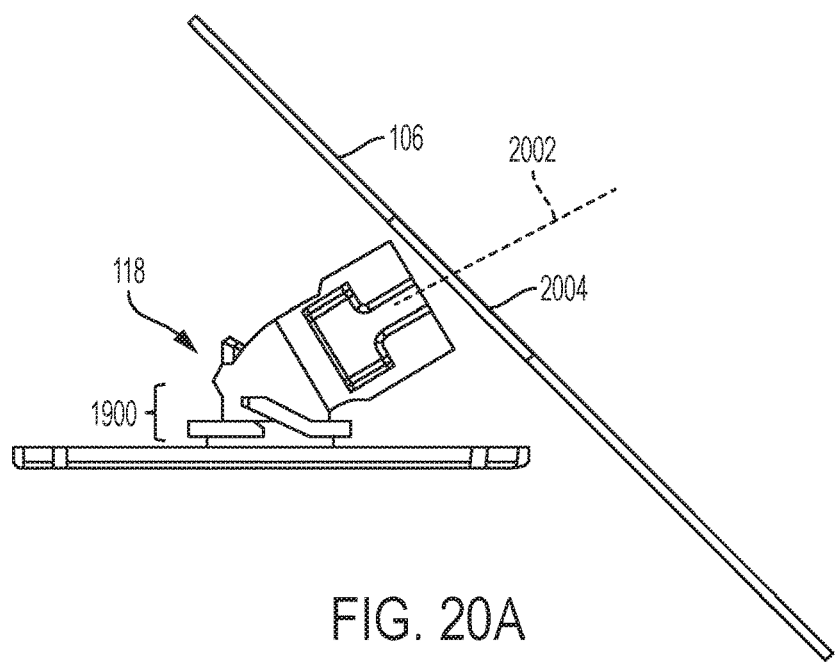
FIGS. 20A, 20B, 20C, and 20D are diagrams showing a sequence for assembling the sealing member to a support member configured with a threaded portion.

FIGS. 20A, 20B, 20C, and 20D are diagrams showing a sequence for assembling the sealing member to a support member configured with a threaded portion. In certain embodiments, the axis of the sealable member 106 is oriented along the longitudinal axis 2002 of the column 122. FIG. 20A is a diagram of a sealable member 106 oriented with respect to the sealable member 118 according to an embodiment.

The sealable member 106 comprises a hole 2004 that has a profile so as to translate along the axis 2002 without contacting the column 122 of the sealable member 118. Alternatively, the sealable member 106 is oriented along a plane parallel to the base 120 during assembly of the sealable member 106 and the support member 118 (not shown).

Figure 20B:
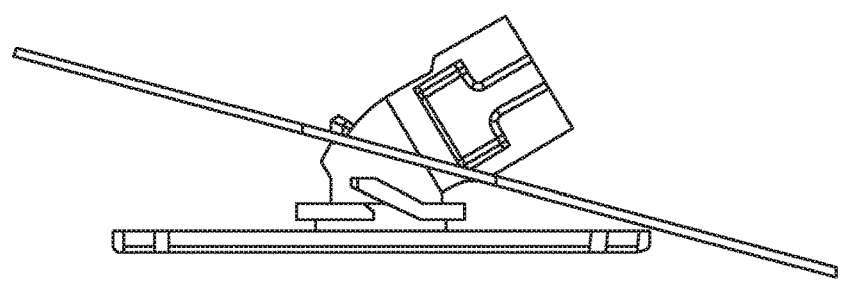

FIG. 20B is a diagram of the sealable member 106 disposed around the column 122.

Figure 20C:
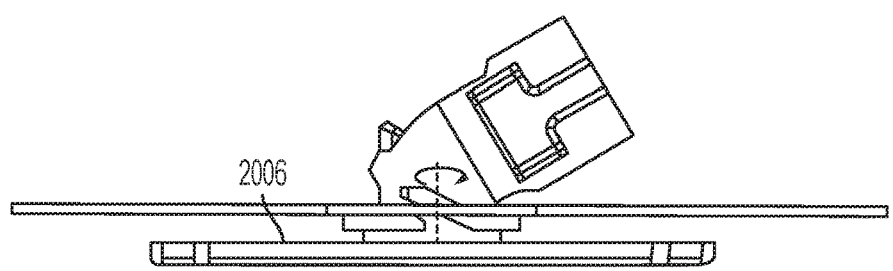

FIG. 20C is a diagram of the sealable member 106 being rotatably translated onto a contact surface 2006 of the base 120 of the support member 118.

Figure 20D:
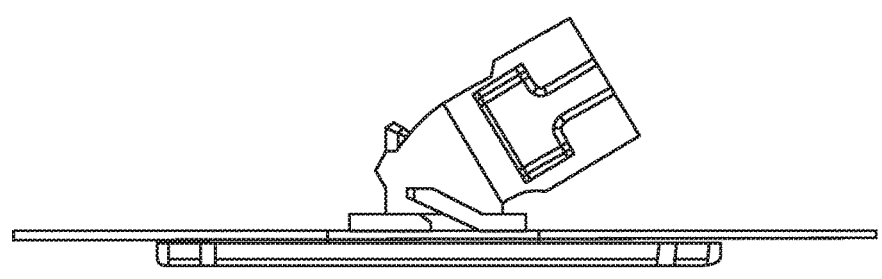

FIG. 20D is a diagram of the sealable member 106 resting on the contact surface 2306 of the base 120.

In certain embodiments, during the assembly, the support member 118 is stationary with respect to the sealable member 106, while the sealable member 106 is moved along the column 122 to the treaded section 1900. In other embodiments, the sealable member 106 is stationary with respect of the support member 118, while the support member 118 is moved through the hole 2004 of the sealable member 106. In yet other embodiments, both the sealable member 106 and the support member 118 move with respect to each other.

Example: Implant for Closing a Hollow Vessel

In some embodiments, the disclosed technology is an implant capable of closing holes in hollow vessels. The implant consists of three distinct parts: a flexible sealing member (e.g., wing), a pin, and a rigid support member (e.g., foot core). This implant may be attached to and packaged with a delivery system. A design is now described below, though other variants, as described herein, may be employed as viable designs to accomplish the same outcomes.

In an example embodiment, the foot core is designed to support the wing during assembly, delivery, and final deployment in the hollow vessel to provide a fast and secure closure of the access site hole. It comprises a flat base with an O-ring shape, two tabs in parallel axis to the foot core column, which protrude out from the perimeter of the O-ring, a threaded section, and recessed sections and through holes.

In some embodiments, the foot core is an integral part of the implant. It includes a hole from the bottom of the center of the O-ring section to the top of the column for guide wire access. It further includes a hole in the foot core column to hold the pin. It includes two recesses on the proximal tip of the column for engaging with the delivery system.

In some embodiments, the shapes of the two spokes in the O-ring are different. This serves the purpose of the larger rear spoke providing extra support (see, for example, FIGS.

4A and 4B) that helps to push the wing against the vessel luminal surface, thereby providing an improved seal. This rear spoke also provides additional security to the user, so that the implant is less likely to be accidently withdrawn fully out of the artery due to folding and/or deformation of the rear spoke. This in turn, provides enhanced tactile feedback to the user during deployment.

In some embodiments, the surface of a vessel lumen can be uneven and is not always uniformly smooth. The ability of the wings to form an effective seal against a vessels wall can be adversely affected if it has a very uneven topography. The rear spoke member, in some embodiments, pushes the wing against the vessel wall forcing the artery to conform to the wing. This creates a seal between the wing and the vessel surface in a variety of vessel surface topographies.

In some embodiments, the base of the O-Ring is flat, at rest, while the artery has a curvature. When the O-Ring implant is deployed into the artery, the flat foot core base adapts to the curvature of the artery and, in some embodiments, pushes the wing against the artery wall to form a contact between the flexible wing and artery inner luminal wall. This may directly enhance the effectiveness of the seal at the tamponade stage of the deployment as it does not rely on the user having to hold the device in a precise location.

In some embodiments, although the O-Ring foot core is constructed of a plastic material, its profile is thin enough to facilitate the "compression/folding" of the transverse sections and not damage itself or the flexible wing during pass through of the implant in the funnel into the loading cannula. The geometry of the foot core base allows the supporting members to fold down under the foot core as it is withdrawn through the loading funnel. The extra support member also keeps the wing in contact with the funnel internal surface during loading giving more consistent loading.

The O-ring foot core design and its variants provides, in some embodiments, support for the flexible wing portion of the implant throughout the life cycle of the implant from initial manufacturing when the implant is assembled through transportation and storage and ultimately during all stages of implant deployment into the hole in the hollow vessel for which it is intended to seal. The O-ring foot core provides, in some embodiments, structural support for the flexible wing when the device is fully assembled in its storage tray. During deployment to close a hole in a hollow vessel, the implant is loaded into a cannula through a loading funnel which reduces the cross-sectional area of the implant (O-ring and flexible wing) to make it possible to deliver the implant through an introducer catheter into a hollow vessel (such as an artery or a vein) within which there had been made an access hole to perform a minimally invasive procedure. During this delivery and deployment of the implant, in certain embodiments, the O-ring foot core supports the wing.

Uses can include closing access site holes in hollow vessels; closing access site holes in blood vessels; closing holes in arteries; closing small and large holes up to 30 F in hollow vessels; closing access site holes in the abdominal post endoscopic procedures; and closing access site holes in the femoral artery, subclavian artery, ascending aorta, axillary and brachial arteries.

Although certain figures and embodiments relate to use of systems and devices for closure of a perforation associated with vascular surgery, one of ordinary skill in the art will appreciate that components of a provided device are not size dependent (i.e., are scalable) and are therefore useful for closure of any perforation in a lumen of a mammal.

Although certain figures and embodiments relate to use of systems and devices for closure of a perforation associated with vascular surgery, one of ordinary skill in the art will appreciate that components of a provided device are not size dependent (i.e., are scalable) and are therefore useful for closure of any perforation in a lumen of a mammal.

Some embodiments of the present invention are directed to a closure system, device, and method of percutaneous closure of an arteriotomy following endovascular/intra S arterial procedures.

Although the present invention has been described with reference to particular examples and exemplary embodiments, it should be understood that the foregoing description is in no manner limiting. Moreover, the features described herein may be used in any combination.

In certain embodiments, the invention is used for closing access site holes in blood vessels or arteries, for example, but not limited to, the femoral artery, subclavian artery, ascending aorta, axillary and brachial arteries.

In certain embodiments, the invention is used for closing access site holes in the abdominal post endoscopic procedures.

In certain embodiments, the invention is used for closing access site holes in hollow vessels. The size of the site holes may be up to 30 French (F) in certain embodiments.

Experimental Data

The provided technologies were tested in vitro and in vivo. For the in vitro test, the sealable member was tested on a test bench using either a flexible tube or a bovine artery to simulate the body lumen. The bovine artery has an inner diameter between 7.8 mm and 9 mm and a wall thickness between 1.4 and 1.9 mm. The flexible tube has an inner diameter of 7.1 mm and a wall thickness of 0.55 mm. In each of the flexible tube and the bovine artery, an aperture was created with a diameter of 6 and 8 mm respectively. A deployment sheath (e.g., the delivery cannula), used in the procedure, has an inner/outer diameter of 20 F/24 F.

The test was performed with water flowing through each of the respective bovine artery and flexible tube, under physiological conditions with a pulse of approximately 60 hertz, a systolic pressure of about 120 mm-Hg, and a diastolic pressure of about 80 mm-Hg. Ten data samples were collected for each test. The amount of water leaked within 5 minutes from the time of deployment is measured and provided in Table 4 and Table 5 below.

TABLE 4

Bovine artery: in vitro test comparison of devices, including (i) a baseline closure device having a rigid base core and a flexible sealable member (see "Current Device R#1") and (ii) a closure device configured with a flexible support base and a flexible sealable member (e.g., comprising a mesh layer and substrate) (see "New Device R#2").

| Total leak in 5 ml (ml) | Current Device R#1 | New Device R#2 |
| --- | --- | --- |
| Mean | 5.2 | 0.9 |
| SD | 4.2 | 0.7 |
| Min | 0.8 | 0.0 |
| Max | 12 | 2.0 |

TABLE 5

Flexible tube: in vitro test comparison of devices, including
(i) the same baseline closure device having a rigid base core
and a flexible sealable member (see "Current Device R#1") and
(ii) the same closure device configured with a flexible support
base and a flexible sealable member (e.g., comprising a mesh
layer and substrate) (see "New Device R#2").

| Total leak in 5 ml (ml) | Current Device R#1 | New Device R#2 |
|---|---|---|
| Mean | 13.6 | 1.8 |
| SD | 12.0 | 1.2 |
| Min | 0 | 0.6 |
| Max | 16 | 4.1 |

The test illustrates a 5× improvement of the closure device, configured with a flexible support member and a flexible sealable member (e.g., comprising the mesh layer and substrate), in reducing the amount of fluid leakage over the design employing a sealable with no mesh layer (and having a rigid core). In addition to the seal formed from the R #2 closure device having improved leakage performance, as shown in the plots of the histograms and the standard deviation values of the tables, a more consistent closure is also provided.

For the in vivo test, the sealable member was tested in animal subjects. A similar 6 mm puncture was made in a pig aorta. The deployment sheath, used in the procedure, also has an inner/outer diameter of 20 F/24 F. Six data samples were collected for each test using the R #1 design and the R #2 design. The total deployment time, tamponade time, time to hemostasis, and total procedure time are provided in Table 6 below.

TABLE 6

Pig Aorta: in vivo study comparison of devices, including (i) the
same baseline closure device having a rigid base core and a flexible
sealable member (see "R#1") and (ii) the same closure
device configured with a flexible support base and a flexible sealable
member (e.g., comprising the mesh layer and substrate) (see "R#2").

| n = 6 | Deployment Time (mm:ss) (Inc TT) | Tamponade Time (TT) (mm:ss) | Time to Hemostasis (TTH) (mm:ss) | Total Procedure Time (mm:ss) | ACT (sec) |
|---|---|---|---|---|---|
| R#1 in vivo study |||||||
| Average | 07:01 | 04:08 | 05:49 | 12:50 | 190 |
| Max | 07:45 | 04:30 | 30:15 | 37:38 | 217 |
| Min | 06:24 | 04:00 | 00:00 | 07:00 | 165 |
| R#2 in vivo study |||||||
| Average | 02:50 | 00:57 | 00:38 | 03:29 | 294 |
| Max | 03:07 | 01:37 | 01:30 | 04:30 | 404 |
| Min | 02:15 | 00:20 | 00:00 | 02:15 | 194 |

As shown in Table 6, the R #2 design improves the total deployment time by 2.5× over the R #1 design. The total deployment time, used in the observations, includes the time for the device to be positioned and deployed in the pig aorta and for the leakage to stop.

In addition, the R #2 design improves the time to hemostasis by 9× over the R #1 design. The time to hemostasis (TTH), used in the observations, refers to the time from which a seal is created and the time for leakage to stop. Less variability in the time to hemostasis is also observed.

In addition, the R #2 design reduces the overall closure procedure time by 3.7× over the R #1 design. The activated clotting time (ACT time) was longer by over 100 seconds. The activated clotting time refers to the time for whole blood to clot upon exposure to an activator.

Although the present invention has been described with reference to particular examples and exemplary embodiments, it should be understood that the foregoing description is in no manner limiting. Moreover, the features described herein may be used in any combination.

What is claimed is:

1. A closure system for sealing an aperture in a tissue, the closure system comprising:
   a loading funnel comprising a narrowing section comprising a first offset surface and a second offset surface;
   a delivery device; and
   a closure device,
   wherein the delivery device has an attachment to releasably attach the closure device for delivery to the aperture in the tissue wherein the delivery device is structured to move the closure device (i) from a stowed configuration to a delivery configuration and (ii) from the delivery configuration to a deployed configuration, and
   wherein the closure device comprises:
      a sealable member positionable against an interior surface of the tissue adjacent the aperture in the tissue when the closure device is in a sealing position so as to form a tamponade at the aperture; and
      a support member comprising a flexible base and a column,
         wherein the column is configured to be disposed in and through the aperture, and the flexible base is configured to be disposed in a body lumen to retain the sealable member against the interior surface of the tissue of the body lumen when the closure device is in the sealing position,
      wherein the flexible base comprises:
         a central portion having a support surface to engage the sealable member against the interior surface of the tissue when the closure device is in the sealing position; and
         one or more lateral support portions extended from the central portion such that the one or more lateral support portions provide additional support surfaces to engage peripheral portions of the sealable member against the interior surface of the tissue when the closure device is in the sealing position,
   wherein, when the closure device is the stowed configuration or the delivery configuration, the sealable member is rolled in the delivery device using the loading funnel, which reduces the cross-sectional area of the sealable member, and
   wherein the first offset surface and the second offset surface initiate folding of a first side of the sealable member and a second side of the sealable member at different locations ensuring the first side of the sealable member and the second side of the sealable member fold in an overlapping manner.

2. The closure system of claim 1, wherein the loading funnel further comprises a third offset surface disposed at a location within the loading funnel with a smaller cross-sectional area than locations of the respective first and second offset surfaces.

3. The closure system of claim 1, wherein the flexible base is pre-loaded to bias the sealable member when in a resting state.

* * * * *